(12) United States Patent
Qin et al.

(10) Patent No.: US 8,399,201 B2
(45) Date of Patent: Mar. 19, 2013

(54) POLYPEPTIDE COMPLEX OF TRPM8 AND CALMODULIN AND ITS USES THEREOF

(75) Inventors: Ning Qin, Blue Bell, PA (US); Christopher M. Flores, Lansdale, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 988 days.

(21) Appl. No.: 11/590,503

(22) Filed: Oct. 31, 2006

(65) Prior Publication Data

US 2007/0105155 A1     May 10, 2007

Related U.S. Application Data

(60) Provisional application No. 60/731,818, filed on Oct. 31, 2005.

(51) Int. Cl.
   *G01N 33/53*      (2006.01)
   *A61K 38/00*      (2006.01)
(52) U.S. Cl. .......................................... 435/7.1; 514/1.1
(58) Field of Classification Search .................. None
See application file for complete search history.

(56) References Cited

U.S. PATENT DOCUMENTS

| | | | |
|---|---|---|---|
| 4,215,051 A | 7/1980 | Schroeder et al. | |
| 4,376,110 A | 3/1983 | David et al. | |
| 4,486,530 A | 12/1984 | David et al. | |
| 5,182,262 A * | 1/1993 | Leto | 514/13 |
| 5,223,409 A | 6/1993 | Ladner et al. | |
| 5,283,173 A | 2/1994 | Fields et al. | |
| 5,525,490 A | 6/1996 | Erickson et al. | |
| 5,571,698 A | 11/1996 | Ladner et al. | |
| 5,622,852 A | 4/1997 | Korsmeyer | |
| 5,695,941 A | 12/1997 | Brent et al. | |
| 5,741,713 A | 4/1998 | Brown et al. | |
| 5,773,218 A | 6/1998 | Gallatin et al. | |
| 5,776,689 A | 7/1998 | Karin et al. | |
| 5,798,247 A | 8/1998 | Albrecht et al. | |
| 5,800,998 A | 9/1998 | Glucksmann | |
| 5,885,779 A | 3/1999 | Sadowski et al. | |
| 5,891,628 A | 4/1999 | Reeders et al. | |
| 5,905,025 A | 5/1999 | Marsolier et al. | |
| 6,037,136 A | 3/2000 | Beach et al. | |
| 6,057,101 A | 5/2000 | Nandabalan et al. | |
| 6,114,111 A | 9/2000 | Luo et al. | |
| 2003/0171275 A1 * | 9/2003 | Baughn et al. | 514/12 |

FOREIGN PATENT DOCUMENTS

| | | |
|---|---|---|
| EP | 1359158 A | 11/2003 |
| WO | 9419478 A1 | 9/1994 |
| WO | 9727296 A1 | 7/1997 |
| WO | 9965939 A1 | 12/1999 |
| WO | WO 01/46258 A | 6/2001 |
| WO | WO 02/10382 A2 | 2/2002 |
| WO | WO 03/087158 A | 10/2003 |
| WO | 2005100386 A2 | 10/2005 |
| WO | WO 2005/094569 A1 | 10/2005 |

OTHER PUBLICATIONS

Rudinger. In: Peptide Hormones, JA Parsons, Ed. (1976) 1-7.*
SIGMA. Designing Custom Peptides. http://www.sigma-genosys.com/peptide_design.asp (Accessed Dec. 16, 2004), 2 pages.*
Stedman et al. Cytoplasmic localization of calcium/calmodulin-dependent protein kinase I-alpha depends on a nuclear export signal in its regulatory domain. FEBS. 2004. 566, pp. 275-280.*
Numazaki et al. Structural determinant of TRPV1 desensitization interacts with calmodulin. PNAS. 2003. vol. 100. No. 13, pp. 8002-8006.*
Proudfoot, et al.: "Analgesia Mediated by the TRPM8 Cold Receptor in Chronic Neuropathic Pain" Current Biology, Current Science, GB, vol. 16, No. 16, Aug. 22, 2006 pp. 1591-1605 XP005606961.
Michael Xi Zhu: "Multiple Roles of Calmodulin and Other Ca2+-binding Proteins in the Functional Regulation of TRP Channels" Pflugers Archiv—European Journal of Physiology; Springer-Verlag, BE, vol. 451, No. 1, Oct. 1, 2005, pp. 105-115, XP019344059.
Tong Qin et al. "Regulation of the Transient Receptor Potential Channel TRPM2 by the Ca2(+) Sensor Calmodulin" Journal of Biological Chemistry, vol. 281, No. 14, Apr. 2006, pp. 9076-9085 XP009081149.
Gordon Reid: "ThermoTRP Channels and Cold Sensing: What are they really up to?" Pflugers Archiv—European Journal of Physiology; Springer-Verlag, BE, vol. 451, No. 1, Oct. 1, 2005, pp. 250-263, XP019344066.
Aley, et al., 1996, Vincristine Hyperalgesia in the Rat: A Model of Painful Vincristine Neuropathy in Humans, Neuroscience, vol. 73, No. 1, pp. 259-265.
Bass, et al., 1991, A Systematic Mutational Analysis of Hormone-Binding Determinants in the Human Growth Hormone Receptor, Procedure National Academy of Science, vol. 88, pp. 4498-4502.
Bennett, et al., 1988, A Peripheral Mononeuropathy in Rat that Produces Disorders of Pain Sensation Like Those Seen in Man, Pain, vol. 33, pp. 87-107.
Bennett, et al., 1991, High Resolution Analysis of Functional Determinants on Human Tissue-Type Plasminogen Activator, The Journal of Biological Chemistry, vol. 266, No. 8, pp. 5191-5201.
Borchardt, et al., 1994, Synthetic Receptor Binding Elucidated with an Encoded Combinatorial Library, Journal of American Chemical Society, vol. 116, pp. 373-374.
Brennan, et al., 1996, Characterization of a Rat Model of Incisional Pain, Pain, vol. 64, pp. 493-501.
Calcutt, et al., 1997, Spinal Pharmacology of Tactile Allodynia in Diabetic Rats, British Journal of Pharmacology, vol. 122, pp. 1478-1482.
Cavaletti, et al., 1995, Experimental Peripheral Neuropathy Induced in Adult rats by Repeated Intraperitoneal Administration of Taxol, Experimental Neurology, vol. 133, pp. 64-72.
Chacur, et al., 2001, A New Model of Sciatic Inflammatory Neuritis (SIN): Induction of Unilateral and Bilateral Mechanical Allodynia Following Acute Unilateral Peri-Sciatic Immune Activation in Rats, Pain, vol. 94, pp. 231-244.

(Continued)

*Primary Examiner* — Marcela M Cordero Garcia
(74) *Attorney, Agent, or Firm* — Andrea Jo Kamage

(57) ABSTRACT

The present invention discovered that a mammalian TRPM8 binds to calmodulin. The present invention provides a polypeptide complex comprising a cold-menthol receptor (TRPM8) or an active fragment or derivative of TRPM8 and a calmodulin or an active fragment or derivative of calmodulin, and the uses of the polypeptide complex.

32 Claims, 2 Drawing Sheets

OTHER PUBLICATIONS

Chen, et al., 1994, Identification of the Target of a Transcription Activator Protein by Protein-Protein Photocrosslinking, Science, vol. 265, pp. 90-92.

Chen, et al., 1996, Nonequilibrium Gating and Voltage Dependence of the CIC-0 C1-Channel, Journal of General Physiology, vol. 108, pp. 237-250.

Choate, et al., 1996, Transglutaminase 1 Delivery to Lamellar Ichthyosis Keratinocytes, Human Gene Therapy, vol. 7, pp. 2247-2253.

Cone, et al., 1984, High-Efficiency Gene Transfer into Mammalian Cells: Generation of Helper-Free Recombinant Retrovirus with Broad Mammalian Host Range, Proc. Natl. Acad. Sci., vol. 81, pp. 6349-6353.

Cubitt, et al., 1995, Understanding, Improving and Using Green Fluorescent Proteins, Trends in Biochemical Sciences, vol. 20, pp. 448-455.

Cull, et al., 1992, Screening for Receptor Ligands Using Large Libraries of Peptides Linked to the C Terminus of the las Repressor, Proc. Natl. Acad. Sci., vol. 89, pp. 1865-1869.

D'Amour, et al., Jan. 27, 1941, A Method for Determining Loss of Pain Sensation, Loss of Pain Sensation, vol. 72, pp. 74-79.

Decosterd, 2000, Spared Nerve Inuury: An Animal Model of Persistent Peripheral Neuropathic Pain, Pain, vol. 87, pp. 149-158.

Denny, et al., 1984, I-labeled Crosslinking Reagent that is Hydrophilic Photoactivatable, and Cleavable Through an aso Linkage, Proc. Natl. Acad. Sci., vol. 81, pp. 5286-5290.

Diamond, et al., 1994, Clustered Charged-to-Alanine Mutagenesis of Poliovirus RNA-Dependent RNA Polymerase Yields Multiple Temperature-Sensitive Mutants Defective in RNA Synthesis, Journal of Virology, vol. 68, No. 2, pp. 863-876.

Ecker, et al., 1995, Combinatorial Drug Discovery: Which Methods will Produce the Greatest Value?, . Biotechnology, vol. 13, pp. 351-360.

Eddy, et al., 1949, Synthetic Analgesics-I. Methadone Isomers and Derivatives, Journal of Pharmacological Exp. Ther., vol. 98, pp. 121-137.

Ferentz, et al., 2000, NMR Spectroscopy: A Multifaceted Approach to Macromolecular Structure, Quarterly Reviews of Biophysics, vol. 33, Issue 1, pp. 29-65.

Fleetwood-Walker, et al., 1999, Behavioural Changes in the Rat Following Infection with Varicella-Zoster Virus, Journal of General Virology, vol. 80, pp. 2433-2436.

Gabe, et al., 1989, The Yeast Gene ERG6 is Required for Normal Membrane Function but is Not Essential for Biosynthesis of the Cell-Cycle-Sparking Sterol, Molecular and Cellular Biology, vol. 9, No. 8, pp. 3447-3456.

Gallop, et al., Apr. 29, 1994, Applications of Combinatorial Technologies to Drug Discovery. 1. Background and Peptide Combinatorial Libraries, Journal of Medicinal Chemistry, vol. 37, No. 9, pp. 1233-1251.

Gilbert, et al., 1971, Interacting Systems of the Type A+B=C, The Journal of Biological Chemistry, vol. 216, No. 19, pp. 6079-6086.

Gill, et al., 1991, *Escherichia Coli* o70 and NusA Proteins I. Binding Interactions with Core RNA Polymerase in Solution and Within the Transcription Complex, Journal Molecular Biology, vol. 220, pp. 307-324.

Gossen, et al., 1992, Tight Control of Gene Expression in Mammalian Cells by Tetrasycline-Responsive Promoters, Pro. Natl. Acad. Sci., vol. 89, pp. 5547-5551.

Graversen, et al., 2000, Mutational Analysis of Affinity and Selectivity of Kringle-Tetranectin Interaction, The Journal of Biological Chemistry, vol. 275, No. 48, pp. 37390-37396.

Hargreaves, et al., 1988, A New and Sensitive Method for Measuring Thermal Nociception in Cutaneous Hyperalgesia, Pain, vol. 32, pp. 77-88.

Hawley, et al., 1994, Versatile Retroviral Vectors for Potential Use in Gene Therapy, Gene Therapy, vol. 1, pp. 136-138.

High, et al., 1993, Site-Specific Photocross-Linking Reveals the Sec61p and TRAM Contact Different Regions of a Membrane-Inserted Signal Sequence, The Journal of Biological Chemistry, vol. 268, No. 35, pp. 28745-28751.

Hofmann, et al., 1996, Rapid Retroviral Delivery of Tetracycline-Inducible Genes in a Single Autoregulatory Cassette, Proc. Natl. Acad. Sci., vol. 93, pp. 5185-5190.

Huber, et al., 1994, Protein-Protein Interactions as Therapeutic Targets for Cancer, Current Medicinal Chemistry, vol. 1, pp. 13-34.

Hummel, et al., 1962, Measurement of Protein-Binding Phenomena by Gel Filtration, Biochim. Biophys. Acta, vol. 63, pp. 530-532.

Hunskaar, et al., 1985, Formalin Test in Mice, a Useful Technique for Evaluating Mild Analgesics, Journal of Neuroscience Methods, vol. 14, pp. 69-76.

Jameson, et al., 1995, Fluorescence Anisotropy Applied to Biomolecular Interactions, Methods in Enzymology, vol. 246, pp. 283-300.

John Hodgson, 1991, Data-Directed Drug Design, Bio Technology, vol. 9, pp. 19-21.

Jordt, et al., 2003, Lessons from Peppers and Peppermint: The Molecular Logic of Thermosensation, Current Opinion in Neurobiology, vol. 13, No. 4, pp. 487-492.

Kao, et al., 1989, Photochemically Generated Cytosolic Calcium Pulses and Their Detection by Fluo-3*, The Journal of Biological Chemistry, vol. 264, vol. 14, pp. 8179-8184.

Kenan, et al., 1994, Exploring Molecular Diversity with Combinatorial Shape Libraries, Trends Biochem. Sc., vol. 19, pp. 57-64.

Kim, et al., 1992, An Experimental Model for Peripheral Neuropathy Produced by Segmental Spinal Nerve Ligation in the Rat, Pain, vol. 50, pp. 355-363.

Kinsella, et al., Aug. 1, 1996, Episomal Vectors Rapidly and Stably Produce High-Titer Recombinant Retrovirus, Human Gene Therapy, vol. 7, pp. 1405-1413.

Kit S. Lam, 1997, Application of Combinatorial Library Methods in Cancer Research and Drug Discovery, Anti-Cancer Drug Design, vol. 12, pp. 145-167.

Kitamura, et al., 1995, Efficient Screening of Retroviral cDNA Expression Libraries, Proc. Natl. Acad. Sci., vol. 92, pp. 9146-9150.

Kumar, et al., May 23, 1997, Physical Interaction Between Specific E2 and Hect E3 Enzymes Determines Functional Cooperativity, The Journal of Biological Chemistry, vol. 272, No. 21, pp. 13548-13554.

Lam, et al., Nov. 7, 1991, A New Type of Synthetic Peptide Library for Identifying Ligand-Binding Activity, Nature, vol. 354, pp. 82-84.

Lewis, et al., 1989, Automated Site-Directed Drug Design: the Concept of Spacer Skeletons for Primary Structure Generation, Proc. R. Soc. Lond., vol. 236, pp. 125-140.

Logan, et al., 1984, Adenovirus Tripartite Leader Sequence Enhances Translation of mRNAs Late After Infection, Proc. Natl. Acad. Sci. USA, vol. 81, pp. 3655-3659.

Mackett, et al., 1982, Vaccinia Virus: A Selectable Eukaryotic Cloning and Expression Vector, Proc. Natl. Acad. Sci. USA, vol. 79, pp. 7415-7419.

Mackett, et al., 1984, General Method for Production and Selection of Infectious Vaccinia Virus Recombinants Expressing Foreign Genes, Journal of Virology, vol. 49, No. 3, pp. 857-864.

Mann, et al., 1983, Construction of a Retrovirus Packaging Mutant and its Use to Produce Helper-Free Defective Retrovirus, Cell, vol. 33, pp. 153-159.

Margolskee, et al., 1988, Epstein-Barr Virus Shuttle Vector for Stable Episomal Replication of cDNA Expression Libraries in Human Cells, Molecular and Cellular Biology, vol. 8, No. 7, pp. 2837-2847.

McKemy, et al., 2002, Identification of a Cold Receptor Reveals a General Role for TRP Channels in Thermosensation, Nature, vol. 416, pp. 52-58.

McKinaly, et al., 1989, Rational Design of Antiviral Agents, Annu. Rev. Pharmacol. Toxicol., vol. 29, pp. 111-122.

Michael Xi Zhu, 2005, Multiple Roles of Calmodulin and Other $Ca^{2+}$-Binding Proteins In the Functional Regulation of TRP Channesl, Eur. J Physiol, Volujme 451, pp. 105-115.

Milligan, et al., 2000, Thermal Hyperalgesia and Mechanical Allodynia Produced by Intrathecal Administration of the Human Immunodeficiency Virus-1 (HIV-1) Envelope Glycoprotein, gp120, Brain Research, vol. 861, pp. 105-116.

Moran, et al., 1995, Radio Frequency Tag Encoded Combinatorial Library Method for the Discovery of Tripeptide-Substituted Cinnamic Acid Inhibitors of the Protein Tyrosine Phosphatase PTP1B, Journal of American Chemical Society, vol. 117, pp. 10787-10788.

Musch, et al., 1992, Yeast Sec Proteins Interact with Polypeptides Traversing the Endoplasmic Reticulum Membrane, Cell, vol. 69, pp. 343-352.

Nelson, et al., 1991, Solution-Phase Equilibrium Binding Interaction of Human Protein S with C4b-Binding Protein, Biochemistry, vol. 30, pp. 2384-2390.

Nozaki-Taguchi, et al., 2001, Pain, Vincritine-induced Allodynia in the Rat vol. 93, pp. 69-76.

Oakley, et al., 2000, Macromolecular Crystallography as a Tool for Investigating Drug, Enzyme and Receptor Interactions, Clinical and Experimental Pharmacology and Physiology, vol. 27, pp. 145-151.

Otto-Bruc, et al., 1993, Interaction Between the Retinal Cyclic GMP Phosphodiesterase Inhibitor and Transducin. Kinetics and Affinity Studies, Biochemistry, vol. 32, pp. 8636-9645.

Panayotou, et al., 1993, Interaction between SH2 Domains and Tyrosine-Phosphorylated Platelet-Derived Growth Factor B-Receptor Sequences: Analysis of Kinetic Parameters by a Novel Biosensor-Based Approach, Molecular and Cellular Biology, vol. 13, No. 6, pp. 3567-3576.

Panicali, et al., 1982, Construction of Poxviruses as Cloning Vectors: Insertion of the Thymidine Kinase Gene from Herpes Simplex Virus into the DNA of Infection Vaccinia Virus, Proc. Natl. Acad. Sci. USA, vol. 79, pp. 4927-4931.

Pear, et al., 1993, Production of High-Titer Helper-Free Retroviruses by Transient Transfection, Proc. Natl. Acad. Sci. USA, vol. 90, pp. 8392-8396.

Peier, et al., Mar. 8, 2002, A TRP Channel that Senses Cold Stimuli and Menthol, Cell, vol. 108, pp. 705-715.

Perry, et al., 1989, The Use of 3D Modelling Databases for Identifying Structure Activity Relationships, OSAR: Quantitive Structure-Activity Relationships in Drug Design, 3D Databases, pp. 189-193.

Phizicky, et al., 1995, Protein-Protein Interactions: Methods for Detection and Analysis, Microbiological Reviews, vol. 59, No. 1, pp. 94-123.

Randall, et al., 1957, A Method for Measurement of Analgesic Activity on Inflamed Tissue, J. Arch. Int. Pharmacodyn, vol. 111, pp. 409-419.

Reid, et al., 2002, A Cold-and Menthol-Activaed Current in Rat Dorsal Root Ganglion Neurones: Properties and Role in Cold Transduction, Journal of Physiology, vol. 545, No. 2, pp. 595-614.

Rickey P. Hicks, 2001, Recent Advances in NMR: Expanding its Role in Rational Drug Design, Current Medicinal Chemistry, vol. 8, pp. 627-650.

Rivas, et al., 1993, New Delopments in the Study of Biomolecular Associations via Sedimentation Equilibrium, Trends in Biochemistry, vol. 18, pp. 284-287.

Riviere, et al., 1995, Effects of Retroviral Vector Design on Expression of Human Adenosine Deaminase in Murine Bone Marrow Transplant Recipients Engrafted with Genetically Modified Cells, Proc. Natl. Acad. Sci. USA, vol. 92, pp. 6733-6737.

Rodney J. Rothstein, 1999, One-Step Gene Disruption in Yeast, Cloning of Genes into Yeast Cells, vol. 101, pp. 202-211.

Rouvinen, et al., 1988, Computer-Aided Drug Design, Acta Pharmaceutical Fennica, vol. 97, pp. 159-166.

Saimi, et al., 2002, Calmodulin as in Ion Channel Subunit, Annu. Rev. Physiol., vol. 64, pp. 289-311.

Sarver, et al., 1981, Bovine Papilloma Virus Deoxyribonucleic Acid: A Novel Eucaryotic Cloning Vector, Mol. Cell. Biol., vol. 1, No. 6, pp. 486-496.

Shir, et al., 1990, A-fibers Mediate Mechanical Hyperesthesia and Allodyina and C-Fibers Mediate Thermal Hyperalgesia in a New Model of Causalgiform Pain Disorders in Rats, Neuroscience Letters, vol. 115, pp. 62-67.

Siegmund, et al., 1957, A Method for Evaluating Both Non-Narcotic and Narcotic Analgesics, Evaluation Method for Analgesics, vol. 95, pp. 729-731.

Sikela, et al., 1987, Screening an Expression Library with a Ligand Probe: Isolation and Sequence of a cDNA Corresponding to a Brain Calmodulin-Binding Protein, Proc. Natl. Acad. Sci, USA, vol. 84, pp. 3038-3042.

Sikorski, et al., 1991, In Vitro Mutagenesis and Plasmid, Methods in Enzymology, vol. 194, pp. 302-318.

Smyth, et al., 2000, Ray Crystallography, J. Clin. Pathol: Mol Pathol, vol. 53, pp. 8-14.

Sudbery, 1996, The Expression of Recombinant Proteins in Yeasts, Current Opinion Biotech., vol. 7, pp. 517-524.

Sugden, et al., 1985, A Vector That Replicates as a Plasmid and Can Be Efficiently Selected in B-Lymphoblasts Transformed by Epstein-Barr Virus, Molecular and Cellular Biology, vol. 5, No. 2, pp. 410-413.

Tang, et al., 2001, Identification of Common Binding Sites for Calmodulin and Inositol 1,4,5-Trisphosphate Receptors on the Carboxyl Termini of TRP Channesl, The Journal of Biological Chemistry, vol. 276, No. 24, pp. 21303-21310.

Trost, et al., 2001, The Transient Receptor Potential, TRP4, Cation Channel is a Novel Member of the Family of Calmodulin Binding Proteins, Biochem. J., vol. 355, pp. 663-670.

Tsavaler, et al., 2001, Trp-p8, A Novel Prostate-Specific Gene, is Up-Regulated in Prostate Cancer and Other Malignancies and Shares High Homology with Transient Receptor Potential Calcium Channel Proteins, Cancer Res, vol. 61, pp. 3760-3769.

Tsien, et al., 1982, Calcium Homeostasis in Intact Lymphocytes: Cytoplasmic Free Calcium Monitored with a New, Intracellularly Trapped Fluorescent Indicator, The Journal of Cell Biology, vol. 94, pp. 325-334.

Vidal, et al., 1996, Genetic Characterization of a Mammalian Protein-Proteing Interaction Domain by Using a Yeast Reverse Two-Hybrid System, Proc. Natl. Acad. Sci. USA, vol. 93, pp. 10321-10326.

Vidal, et al., 1996, Reverse Two-Hybrid and One-Hyrbid Systems to Detect Dissociation of Protein-Protein and DNA-Protein Interaction, Proc. Natl. Acad. Sci. USA, vol. 93, pp. 10315-10320.

Von Prof. F. Haffner, May 3, 1929, Experimentelle Prufung Schmerzstillender Mittel, Dtsch Med Wochenschr, vol. 55, pp. 731-733.

Wach, et al., 1994, New Heterologous Modules for Classical or PCR-based Gene Disruptions in Saccharomyces Cerevisia, Yeast, vol. 10, pp. 1793-1808.

Baird, et al., 1976, Chemical Cross-Linking Studies of Chloroplast Coupling Factor 1*, The Journal of Biological Chemistry, vol. 251, No. 22, pp. 6953-6962.

Bitter, et al., 1987, Expression and Secretion Vectors for Yeast, Methods in Enzymology, vol. 153, pp. 516-544.

Gordon Reid, 2005, ThermoTRP Channesl and Cold Sensing: What Are They Really Up to?, Eur J. Physiol, vol. 451, pp. 250-263.

Gordon, et al., 1994, Applications of Combinatorial Technologies to Drug Discovery. 2. Combinatorial Organic Synthesis, Library Screening Strategies, and Future Directions, Journal of Medicinal Chemistry, vol. 37, No. 10, pp. 1385-1401.

Grynkiewicz, et al., 1985, A New Generation of Ca2+ Indicators with Greatly Improved Fluorescence Properties*, The Journal of Biological Chemistry, vol. 260, No. 6, pp. 3440-3450.

Houghten, et al., 1992, The Use of Synthetic Peptide Combinatorial Libraries for the Identification of Bioactive Peptides, Biotechniques, vol. 13, No. 3, pp. 412-421.

Roberts, 1999, NMR Spectroscopy in the Structure-Based Drug Design, Current Opinion in Biotechnology, vol. 10, pp. 42-47.

Scott, et al., 1990, Searching for Peptide Ligands with an Epitope Library, Science, vol. 249, pp. 386-390.

Weiel, et al., 1981, Fluorescence Polarization Studies of the Interaction of *Escherichia Coli* Protein Synthesis Initiation Factor 3 with 30S Ribosomal Subunits, Biochemistry, vol. 20, pp. 5859-5865.

Wiedmann, et al., 1989, Photocrosslinking Demonstrates Proximity of a 34 kDa Membrane Protein to Different Portions of Preprolactin During Translocation Through the Endoplasmic Reticulum, Nature, vol. 257, No. 2, pp. 263-268.

Yang, et al., 1995, Protein-Peptide Interactions Analyzed with the Yeast Two-Hybrid System, Nucleic Acids Research, vol. 23, No. 7, pp. 1152-1156.

Zhang, et al., 2001, Activation of Trp3 by Inositol 1,4,5-Trisphophate Receptors Through Displacement of Inhibitory Calmodulin from a Common Binding Domain, Proc. Natl. Acad. Sci. USA, vol. 98, No. 6, pp. 3168-3173.

Zuckermann, et al., 1994, Discovery of Nanomolar Ligands for 7-Transmembrane G-Protein-Coupled Receptors for a Diverse N-(Substituted)Glycine Peptoid Library, J. Med. Chem., vol. 37, pp. 2678-2685.

\* cited by examiner

POLYPEPTIDE COMPLEX OF TRPM8 AND CALMODULIN AND ITS USES THEREOF

CROSS REFERENCE TO RELATED APPLICATIONS

This application claims priority to Application No. 60/731,818 filed on Oct. 31, 2005, the entire contents of which are incorporated by reference herein.

FIELD OF THE INVENTION

The present invention relates to regulation of cold sensation and pain. More particularly, the present invention relates to a polypeptide complex comprising a cold-menthol receptor (TRPM8) or an active fragment or derivative of TRPM8 and a calmodulin or an active fragment or derivative of calmodulin, and the uses of the polypeptide complex.

BACKGROUND OF THE INVENTION

The transient receptor potential (TRP) cation channels are involved in thermosensation of mammals. These channels are located on sensory neurons of the dorsal root ganglion (DRG) or the trigeminal ganglion (TG). They detect and transduce thermal-stimuli into electrical signals, i.e., action potentials. The electrical signals are then propagated from peripheral tissues to the spinal cord and brain, where they are integrated and interpreted to trigger appropriate reflexive and cognitive responses (Jordt et al., *Curr Opin Neurobiol.* 2003, 13(4): 487-92). Distinct TRP channels that are activated by specific temperatures and expressed in specific patterns have been identified. The combinatorial effect of the TRP channels enables a mammal to sense a broad range of thermal stimuli, namely those that are uncomfortable, noxious, hot or cold. Accordingly, these thermal receptors represent highly promising targets for the treatment of various painful conditions or for uses in other conditions in which tissue cooling is desirable.

TRPM8, the transient receptor potential channel, melanostatin subfamily, type 8, also called CMR1, the cold-menthol receptor, is a nonselective cationic channel permeable to $Ca^{2+}$. TRPM8 is expressed in a subpopulation of sensory neurons that is activated both by decreases in temperature and cooling compounds, such as menthol, eucalyptol, icilin (McKemy et al., *Nature*, 2002, 416:52-58). TRPM8 offers interesting insight into the fundamental biology of cold perception. Modulation of TRPM8 can be relevant for therapeutic applications. For example, cold treatment is often used as a method of pain relief. Since the TRPM8 receptor is responsive to cold and compounds, such as menthol and icilin, that mimic a cold-like sensation, it is anticipated that modulation of TRPM8 activity is relevant for therapeutic applications where cold or menthol treatment is used as a method of pain relief or other relief, such as congestive rhinitis, cough or asthmatic bronchitis. Modulation of function or expression of TRPM8 proteins can also be useful for patients having dermal or mucus membrane conditions, such as skin inflammation and dermal burns, including sunburn and razor burn, or sore throat. Modulation of TRPM8 activity can further be relevant in patients suffering from hypersensitivity to cold that causes cold allodynia. In addition, modulation of TRPM8 activity can also be relevant for treating acute pain, for example, toothache (odontalgia) and other trigeminally distributed pains, such as trigeminal neuralgia (tic douleureux) and temperomandibular joint pain. Since human TRPM8 has been identified as a marker that is associated with tumor growth (Tsavaler, L., et al. *Cancer Res.*, 2002, 61:3760-3769), modulation of TRPM8 can also be useful for the diagnosis of various cellular proliferation disorders.

Like many ion channels, TRPM8 is regulated by calcium. For example, lowering extracellular $Ca^{2+}$ concentrations in vivo (by infusion of EDTA) or immersing the channels in isolated perfused preparations strongly increases the activity of the receptor, while raising extracellular $Ca^{2+}$ concentrations antagonizes the actions of menthol on spike frequency and burst firing pattern. In addition, a rise in intracellular $Ca^{2+}$ concentrations, either from cooling or artificial induction, triggers cold adaptation, by shifting the temperature sensitivity of the cold- and menthol-activated current (Reid et al., *J. Physiol.*, 2002, 545:595-614). Transient rises and falls in intracellular $Ca^{2+}$ levels register as local or global $Ca^{2+}$ sparks and control numerous physiological events. However, prolonged high $Ca^{2+}$ presence in the cytoplasm kills the cells.

Calmodulin (CaM) is found to be involved in many signaling pathways to decode intracellular $Ca^{2+}$ concentration levels. A variety of ion channels found in a wide range of species, from *Homo* to *Paramecium*, use calmodulin (CaM) as their constitutive or dissociable $Ca^{2+}$-sensing subunits (Saimi et al., *Annu Rev Physiol.* 2002, 64:289-311). CaM is a small, acidic, and highly conserved soluble calcium binding protein that is ubiquitously expressed. CaM binds $Ca^{2+}$ as a monomer with two pairs of EF hands, which are common calcium binding motifs. Upon binding $Ca^{2+}$, CaM becomes more extended with each pair of its EF hands opening to reveal a hydrophobic patch that is available to bond with a target and "activate it." (Saimi et al, supra). The activated targets include those involved in protein phosphorylation, cyclic nucleotide metabolism, calcium homeostasis, etc.

Some TRP proteins have been found to interact with calmodulin in a $Ca^{2+}$-dependent manner (Tang et al., *J. Biol. Chem.* 2001, 276:21303-21310). For example, CaM-binding occurs at two domains within the cytoplasmic C-terminal region of the TRP4 protein (Trost et al., 2001, *Biochem J.* 355(Pt 3):663-70). The presence of a CaM-binding site in the C terminus of TRP3 has also been reported (Zhang et al., *Proc Natl. Acad Sci USA.* 2001, 98(6):3168-73).

There is a need for systems that can be used to identify and test compounds that potentially increase or decrease the activity of a TRPM8. Identification and testing of such compounds would enable the treatment of various disorders associated with chronic pain and for uses in other conditions in which tissue cooling is desirable.

SUMMARY OF THE INVENTION

It has now been discovered that a mammalian TRPM8 binds to calmodulin.

In one aspect, the invention provides an isolated polypeptide complex comprising 1) a TRPM8 or an active fragment or derivative of TRPM8 interacting with 2) a calmodulin or an active fragment or derivative of calmodulin.

In another aspect, the invention provides a method of producing a polypeptide complex comprising the step of: a) contacting 1) a TRPM8 or an active fragment or derivative of TRPM8 with 2) a calmodulin or an active fragment or derivative of calmodulin under a condition that allows the formation of a polypeptide complex comprising the protein of 1) interacting with the protein of 2), wherein at least one of the proteins of 1) and 2) is in isolated form or is recombinantly expressed; and b) isolating the polypeptide complex.

In yet another aspect, the invention provides a method of identifying a modulator for a TRPM8-calmodulin polypeptide complex, comprising the steps of: a) contacting 1) a TRPM8 or an active fragment or derivative of TRPM8 with 2) a calmodulin or an active fragment or derivative of calmodulin under a condition that allows the formation of a polypeptide complex comprising the protein of 1) interacting with the protein of 2); b) contacting a test compound with at least one of the proteins of 1) and 2); c) determining the amount of the polypeptide complex formed; d) repeating step a) and c); e) comparing the amount of the polypeptide complex formed as determined from step b) with that from step d).

The invention also provides a method of identifying a compound useful for treating pain, comprising the step of identifying a modulator for a TRPM8-calmodulin polypeptide complex.

The invention further provides a method of reducing pain in a subject comprising the step of administering to the subject an effective amount of a compound that is a modulator for a TRPM8-calmodulin polypeptide complex.

Other aspects of the invention include an isolated protein, an isolated nucleic acid molecule, an expression vector, and a recombinant cell related to an active fragment of TRPM8 that binds to a calmodulin.

DETAILED DESCRIPTION

Figure 1:
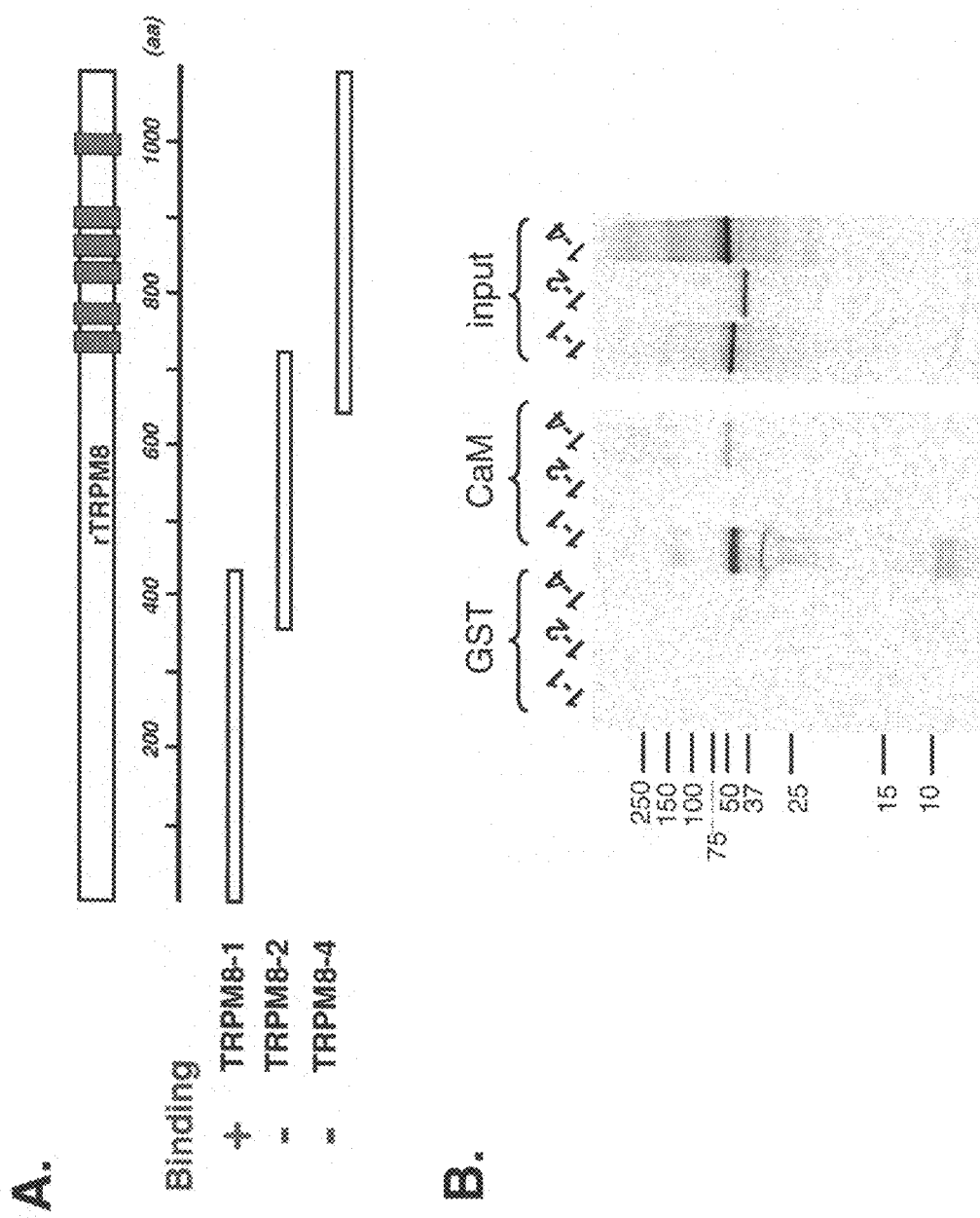
FIG. 1 illustrates the results of a pull-down assay detecting TRPM8 fragments that bound to a GST-CaM fusion protein. (A) A linear diagram representation of the TRPM8 fragments and their binding to CaM: (+) binding was detected; (−) no binding was detected. (B) Pictures of autoradiograph showing the $^{35}$S-methionine-labeled TRPM8 fragment. GST: no TRPM8 fragment was found to interact with the GST; CaM: some TRPM8 fragment was found to interact with the GST-CaM fusion protein; and input: TRPM8 fragments that were tested in the assay.

All publications cited herein are hereby incorporated by reference. Unless defined otherwise, all technical and scientific terms used herein have the same meaning as commonly understood to one of ordinary skill in the art to which this invention pertains.

As used herein, the terms "comprising", "containing", "having" and "including" are used in their open, non-limiting sense.

The following are abbreviations that are at times used in this specification:
bp=base pair
cDNA=complementary DNA
$Ca^{2+}$=calcium
CaM=calmodulin
CMR1=cold- and menthol-sensitive receptor 1;
DRG=dorsal root ganglion
FRET=fluorescence resonance energy transfer
FP=fluorescence polarization
kb=kilobase; 1000 base pairs
PAGE=polyacrylamide gel electrophoresis
PCR=polymerase chain reaction
SDS=sodium dodecyl sulfate
TG=trigeminal ganglion
TRPM8=transient receptor potential channel, melanostatin subfamily, type 8

"Binding activity" refers to the ability of two or more molecular entities to bind or interact with each other.

A "calmodulin" or "CaM" refers to a small, acidic, and highly conserved soluble calcium binding protein that is ubiquitously expressed. Upon binding $Ca^{2+}$, the CaM can also bind to a target polypeptide and thus regulates the biological activity of the target polypeptide. CaM can be identified by its occurrence in the cytosol or on membranes facing the cytosol and by a high affinity for calcium. The functions of calmodulin include roles in growth and the cell cycle as well as in signal transduction and the synthesis and release of neurotransmitters. An exemplary CaM has an amino acid sequence depicted in SEQ ID NO: 1, having 149 amino acids and 4 calcium-binding domains. Exemplary CaM also includes structural and functional polymorphisms of the CaM protein depicted in SEQ ID NO: 1. "Polymorphism" refers to a set of genetic variants at a particular genetic locus among individuals in a population.

An "active fragment or derivative of calmodulin" as used herein refers to that part of a camodulin or a non-CaM polypeptide comprising that part of a calmodulin that maintains its ability to bind to a TRPM8 in a manner analogous to that of the full-length calmodulin, as determined in vivo or in vitro, according to standard techniques for measuring protein-protein interactions. An exemplary active fragment or derivative of calmodulin is a TRPM8 interaction domain of calmodulin.

A "cell" refers to at least one cell or a plurality of cells appropriate for the sensitivity of the detection method. Cells suitable for the present invention may be bacterial, but are preferably eukaryotic, and are most preferably mammalian.

A "cold- and menthol-sensitive receptor", a "CMR1", a "transient receptor potential channel, melanostatin subfamily, type 8", or a "TRPM8", each refers to a protein that is capable of sensing and transducing cold stimuli, such as cold temperatures or compounds that provoke cold sensations including, but not limited to, menthol and icilin. A "TRPM8" can form an excitory ion channel, the TRPM8 channel, which can be activated by low temperature or compounds that provoke cold sensations. An activated TRPM8 channel gates the influx of $Ca^{++}$ ions through the channel, resulting in membrane depolarization. A TRPM8 can have greater than about 80% amino acid sequence identity to a human TRPM8 protein (NP_076985) depicted in SEQ ID NO: 2. The human TRPM8 has previously been identified as a prostate-specific transcript and has also been found to be expressed in various tumor tissue, including prostate, melanoma, colorectal and breast carcinoma (Tsavaler, L., et al. *Cancer Res.* 2002, 61:3760-3769). In some embodiments, a TRPM8 has greater than about 85, 90, or 95 percent amino acid sequence identity to SEQ ID NO: 2. Exemplary TRPM8 includes structural and functional polymorphisms of the human TRPM8 protein depicted in SEQ ID NO: 2. TRPM8 also includes orthologs of the human TRPM8 in other animals including rat, mouse, pig, dog and monkey, for example, the structural and functional polymorphisms of the rat TRPM8 (SEQ ID NO:3, GenBank protein ID: NP_599198, McKemy, D. D., et al. 2002, supra)

or mouse TRPM8 (SEQ ID NO:4, GenBank protein ID: NP_599013, Peier, A. M. et al., 2002, *Cell* 108:705-715).

An "active fragment or derivative of TRPM8" as used herein refers to that part of a TRPM8 or a non-TRPM8 polypeptide comprising that part of a TRPM8 that maintains its ability to bind to CaM in a manner analogous to that of the full-length TRPM8, as determined in vivo or in vitro, according to standard techniques for measuring protein-protein interactions. An active fragment or derivative of TRPM8 can be a calmodulin interaction domain of TRPM8. Exemplary active fragment or derivative of TRPM8 can have the amino acid sequence of SEQ ID NO:5, SEQ ID NO:6, SEQ ID NO:7, SEQ ID NO:8, SEQ ID NO:9, fragments of the rat TRPM8 that was found to interact with calmodulin.

"Nucleotide sequence" refers to the arrangement of either deoxyribonucleotide or ribonucleotide residues in a polymer in either single- or double-stranded form. Nucleic acid sequences can be composed of natural nucleotides of the following bases: thymidine, adenine, cytosine, guanine, and uracil; abbreviated T, A, C, G, and U, respectively, and/or synthetic analogs of the natural nucleotides.

An "isolated" nucleic acid molecule is one that is substantially separated from at least one of the other nucleic acid molecules present in the natural source of the nucleic acid, or is substantially free of at least one of the chemical precursors or other chemicals when the nucleic acid molecule is chemically synthesized. An "isolated" nucleic acid molecule can also be, for example, a nucleic acid molecule that is substantially free of at least one of the nucleotide sequences that naturally flank the nucleic acid molecule at its 5' and 3' ends in the genomic DNA of the organism from which the nucleic acid is derived. A nucleic acid molecule is "substantially separated from" or "substantially free of" other nucleic acid molecule(s) or other chemical(s) in preparations of the nucleic acid molecule when there is less than about 30%, 20%, 10%, or 5% (by dry weight) of the other nucleic acid molecule(s) or the other chemical(s) (also referred to herein as a "contaminating nucleic acid molecule" or a "contaminating chemical").

Isolated nucleic acid molecules include, without limitation, separate nucleic acid molecules (e.g., cDNA or genomic DNA fragments produced by PCR or restriction endonuclease treatment) independent of other sequences, as well as nucleic acid molecules that are incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a nucleic acid molecule that is part of a hybrid or fusion nucleic acid molecule. An isolated nucleic acid molecule can be a nucleic acid sequence that is: (i) amplified in vitro by, for example, polymerase chain reaction (PCR); (ii) synthesized by, for example, chemical synthesis; (iii) recombinantly produced by cloning; or (iv) purified, as by cleavage and electrophoretic or chromatographic separation.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by the codons of genes may also be included in a polypeptide.

An "isolated protein" is one that is substantially separated from at least one of the other proteins present in the natural source of the protein, or is substantially free of at least one of the chemical precursors or other chemicals when the protein is chemically synthesized. A protein is "substantially separated from" or "substantially free of" other protein(s) or other chemical(s) in preparations of the protein when there is less than about 30%, 20%, 10%, or 5% (by dry weight) of the other protein(s) or the other chemical(s) (also referred to herein as a "contaminating protein" or a "contaminating chemical").

Isolated proteins can have several different physical forms. The isolated protein can exist as a full-length nascent or unprocessed polypeptide, or as a partially processed polypeptide or as a combination of processed polypeptides. The full-length nascent polypeptide can be postranslationally modified by specific proteolytic cleavage events that result in the formation of fragments of the full-length nascent polypeptide. A fragment, or physical association of fragments can have the biological activity associated with the full-length polypeptide; however, the degree of biological activity associated with individual fragments can vary.

An isolated polypeptide can be a non-naturally occurring polypeptide. For example, an "isolated polypeptide" can be a "hybrid polypeptide." An "isolated polypeptide" can also be a polypeptide derived from a naturally occurring polypeptide by additions or deletions or substitutions of amino acids. An isolated polypeptide can also be a "purified polypeptide" which is used herein to mean a specified polypeptide in a substantially homogeneous preparation substantially free of other cellular components, other polypeptides, viral materials, or culture medium, or when the polypeptide is chemically synthesized, chemical precursors or by-products associated with the chemical synthesis. A "purified polypeptide" can be obtained from natural or recombinant host cells by standard purification techniques, or by chemical synthesis, as will be apparent to skilled artisans.

The terms "hybrid protein," "hybrid polypeptide," "hybrid peptide," "fusion protein," "fusion polypeptide," and "fusion peptide" are used herein interchangeably to mean a non-naturally-occurring polypeptide or isolated polypeptide having a specified polypeptide molecule covalently linked to one or more other polypeptide molecules that do not link to the specified polypeptide in nature. Thus, a "hybrid protein" can be two naturally occurring proteins or fragments thereof linked together by a covalent linkage. A "hybrid protein" can also be a protein formed by covalently linking two artificial polypeptides together. Typically but not necessarily, the two or more polypeptide molecules are linked or "fused" together by a peptide bond forming a single non-branched polypeptide chain.

As used herein, the term "interacting" or "interaction" means that two protein domains, fragments or complete proteins exhibit sufficient physical affinity to each other so as to bring the two "interacting" protein domains, fragments or proteins physically close to each other. The interaction can be from the formation of one or more chemical bonds that results in continual and stable proximity of the two interacting entities. The interaction can also be based solely on physical affinities, which can be equally effective in co-localizing two proteins. Examples of physical affinities and chemical bonds include but are not limited to, forces caused by electrical charge differences, hydrophobicity, hydrogen bonds, van der Waals force, ionic force, covalent linkages, and combinations thereof. The state of proximity between the interaction domains, fragments, proteins or entities can be transient or permanent, reversible or irreversible. In any event, it is in contrast to and distinguishable from contact caused by natural random movement of two entities. Typically, although not necessarily, an "interaction" is exhibited by the binding between the interaction domains, fragments, proteins, or entities. Examples of interactions include specific interactions between antigen and antibody, ligand and receptor, enzyme and substrate, and the like.

As used herein, the term "protein complex" or "polypeptide complex" means a composite unit that is a combination of two or more proteins formed by interaction between the proteins. Typically but not necessarily, a "protein complex" is formed by the binding of two or more proteins together through specific non-covalent binding affinities. However, covalent bonds may also be present between the interacting partners. For instance, the two interacting partners can be covalently crosslinked so that the protein complex becomes more stable.

The term "isolated protein complex" means a protein complex present in a composition or environment that is different from that found in its native or original cellular or biological environment in nature. An "isolated protein complex" can also be a protein complex that is not found in nature.

The term "protein fragment" as used herein means a polypeptide that represents a portion of a protein. When a protein fragment exhibits interactions with another protein or protein fragment, the two entities are said to interact through interaction domains that are contained within the entities. Interaction domains can be compact structures formed by amino acid residues that are close to one another in the primary sequence of a protein. Alternatively, interaction domains can be comprised of amino acid residues from portions of the polypeptide chain that are not close to one another in the primary sequence, but are brought together by the tertiary fold of the polypeptide chain.

As used herein, the term "domain" means a functional portion, segment or region of a protein, or polypeptide. "Interaction domain" refers specifically to a portion, segment or region of a protein, polypeptide or protein fragment that is responsible for the physical affinity of that protein, protein fragment or isolated domain for another protein, protein fragment or isolated domain.

"Recombinant" refers to a nucleic acid, a protein encoded by a nucleic acid, a cell, or a viral particle, that has been modified using molecular biology techniques to something other than its natural state. For example, recombinant cells can contain nucleotide sequence that is not found within the native (non-recombinant) form of the cell or can express native genes that are otherwise abnormally expressed, underexpressed, or not expressed at all. Recombinant cells can also contain genes found in the native form of the cell wherein the genes are modified and re-introduced into the cell by artificial means. The term also encompasses cells that contain an endogenous nucleic acid that has been modified without removing the nucleic acid from the cell; such modifications include those obtained, for example, by gene replacement, and site-specific mutation.

A "recombinant host cell" is a cell that has had introduced into it a recombinant DNA sequence. Recombinant DNA sequence can be introduced into host cells using any suitable method including, for example, electroporation, calcium phosphate precipitation, microinjection, transformation, biolistics and viral infection. Recombinant DNA may or may not be integrated (covalently linked) into chromosomal DNA making up the genome of the cell. For example, the recombinant DNA can be maintained on an episomal element, such as a plasmid. Alternatively, with respect to a stably transformed or transfected cell, the recombinant DNA has become integrated into the chromosome so that it is inherited by daughter cells through chromosome replication. This stability is demonstrated by the ability of the stably transformed or transfected cell to establish cell lines or clones comprised of a population of daughter cells containing the exogenous DNA. Recombinant host cells may be prokaryotic or eukaryotic, including bacteria such as *E. coli*, fungal cells such as yeast, mammalian cells such as cell lines of human, bovine, porcine, monkey and rodent origin, and insect cells such as *Drosophila* and silkworm-derived cell lines. It is further understood that the term "recombinant host cell" refers not only to the particular subject cell, but also to the progeny or potential progeny of such a cell. Because certain modifications can occur in succeeding generations due to either mutation or environmental influences, such progeny may not, in fact, be identical to the parent cell, but are still included within the scope of the term as used herein.

A "reporter gene" refers to a nucleic acid sequence that encodes a reporter gene product. As is known in the art, reporter gene products are typically easily detectable by standard methods. Exemplary suitable reporter genes include, but are not limited to, genes encoding luciferase (lux), β-galactosidase (lacZ), green fluorescent protein (GFP), chloramphenicol acetyltransferase (CAT), β-glucuronidase, neomycin phosphotransferase, and guanine xanthine phosphoribosyl-transferase proteins.

"Vector" refers to a nucleic acid molecule into which a heterologous nucleic acid can be or is inserted. Some vectors can be introduced into a host cell allowing for replication of the vector or for expression of a protein that is encoded by the vector or construct. Vectors typically have selectable markers, for example, genes that encode proteins allowing for drug resistance, origins of replication sequences, and multiple cloning sites that allow for insertion of a heterologous sequence. Vectors are typically plasmid-based and are designated by a lower case "p" followed by a combination of letters and/or numbers. Starting plasmids disclosed herein are either commercially available, publicly available on an unrestricted basis, or can be constructed from available plasmids by application of procedures known in the art. Many plasmids and other cloning and expression vectors that can be used in accordance with the present invention are well-known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Sequence" means the linear order in which monomers occur in a polymer, for example, the order of amino acids in a polypeptide or the order of nucleotides in a polynucleotide.

In practicing the present invention, many conventional techniques in molecular biology, microbiology and recombinant DNA are used. These techniques are well-known and are explained in, for example, Current Protocols in Molecular Biology, Vols. I, II, and III, F. M. Ausubel, ed. (1997); and Sambrook et al., Molecular Cloning: A Laboratory Manual, Cold Spring Harbor Laboratory Press, Cold Spring Harbor, N.Y. (2001).

In one aspect, the invention provides an isolated polypeptide complex comprising 1) a TRPM8 or an active fragment or derivative of TRPM8 interacting with 2) a calmodulin or an active fragment or derivative of calmodulin.

Accordingly, in one embodiment, the present invention provides isolated protein complexes formed between full-length TRPM8 and calmodulin proteins representing the naturally-occurring complexes found in vivo. It is widely accepted in the field of protein-protein interactions that interactions between fragments of full-length proteins are generally indicative of interactions formed between corresponding full-length proteins containing such fragments. Thus, in view of the disclosure provided herein, an ordinarily skilled person in the art would envisage active fragments or derivatives of TRPM8 and CaM proteins that interact in a manner analogous to that of the full-length proteins. Thus, in another embodiment, the present invention provides numerous other protein complexes comprised of active fragments or derivatives of TRPM8 and CaM proteins that interact in a manner analogous to that of the full-length proteins.

The protein complexes of the invention comprise polypeptides that include the necessary interaction domains required to form the protein complexes. Experimentation, optionally directed by analysis of multiple sequence alignments to identify conserved amino acid residues, and stretches of contiguous amino acid residues, can be used to define the minimal interacting fragments of the CaM or TRPM8 protein. Shorter and shorter fragments of TRPM8 can be tested for their ability to interact with CaM. Such experimentation often involves systematically and progressively shorter portions of one or both of the CaM and TRPM8 proteins. The subsequent testing to determine whether such truncated fragments still interact, will predictably lead to the elucidation of minimal interacting fragments still capable of interacting with the interacting partner.

For example, after detecting the binding between CaM and a large N-terminal fragment of the human TRPM8 (SEQ ID NO:5), smaller human TRPM8 fragments were tested for their ability to bind CaM. It was discovered that within the large N-terminal fragment, a small human TRPM8 fragment (SEQ ID NO:9) consisting 53 amino acid residues was still able to bind to CaM. Sequence comparison showed that this fragment is highly conserved among the animals. The sequences of TRPM8s from human, dog, rat, and mouse, are 100% identical in a region including and surrounding this 53 amino acid stretch. Thus, one exemplary protein complex of the invention comprises TRPM8 protein fragments containing the amino acid residues defined by SEQ ID NO: 9. Other exemplary protein complexes of the invention comprise TRPM8 active fragments or derivatives that have additional amino acid residues at either or both ends of SEQ ID NO:9.

One of skill in the art of molecular biology and protein-protein interactions, using routine experimentation, can introduce amino acid sequence variations in a CaM, TRPM8, or an active fragment or derivative thereof. Optionally directed by analysis of multiple sequence alignments to identify variable amino acid residues, one of skill in the art can use site-directed mutagenesis to introduce specific changes in the amino acid sequence of the interacting partner polypeptides, and thereby produce "synthetic homologues" of the CaM or TRPM8, or any interacting fragments thereof. For example, one of skill in the art could introduce changes in the codons encoding specific amino acid residues found to vary in orthologous proteins. Similarly, one of skill in the art could introduce changes in the codons encoding specific amino acid residues that result in conservative substitutions of those amino acid residues. For example, using such methods, one of skill in the art could introduce a site-specific mutation that changes a "CTT" codon to an "ATT" codon, thereby causing a leucine residue in the native polypeptide to be replaced by an isoleucine residue in the synthetic homologue. To a first approximation, such a conservative substitution in the expressed polypeptide would not be expected to abrogate the ability of the synthetic homologue to interact with its partner protein, and it may, in fact increase the affinity of the interaction (see Graversen et al., *J. Biol. Chem.* 275:37390-37396 (2000)).

In a specific embodiment of the protein complex of the present invention, the CaM and TRPM8 proteins, or the active fragments or derivatives thereof, can be directly fused together, or covalently linked together through a peptide linker, forming a hybrid protein having a single unbranched polypeptide chain. Thus, the protein complex may be formed by "intramolecular" interactions between two portions of the hybrid protein. Again, one or both of the fused or linked interacting partners in this protein complex may be a native protein or a homologue, derivative or fragment of a native protein.

The protein complexes of the present invention can also be in a modified form. For example, an antibody selectively immunoreactive with the protein complex can be bound to the protein complex. In another example, a non-antibody modulator capable of enhancing the interaction between the interacting partners in the protein complex may be included. Alternatively, the protein members in the protein complex can be cross-linked for purposes of stabilization. Various crosslinking methods may be used. For example, a bifunctional reagent in the form of R—S—S—R' may be used in which the R and R' groups can react with certain amino acid side chains in the protein complex forming covalent linkages. See e.g., Traut et al., in Creighton ed., *Protein Function: A Practical Approach*, IRL Press, Oxford, 1989; Baird et al., *J. Biol. Chem.*, 251: 6953-6962 (1976). Other useful crosslinking agents include, e.g., Denny-Jaffee reagent, a heterbifunctional photoactivable moiety cleavable through an azo linkage (see Denny et al., *Proc. Natl. Acad. Sci. USA*, 81:5286-5290 (1984)), and $^{125}$I—{S—[N—(3-iodo-4-azidosalicyl)cysteaminyl]-2-thiopyridine}, a cysteine-specific photocrosslinking reagent (see Chen et al., *Science*, 265:90-92 (1994)).

In some embodiments, the isolated protein complex of the present invention comprises a TRPM8 that is associated with an isolated membrane preparation. The membrane preparation can be isolated from a native host cell, for example, a DRG or TG cell, which expresses TRPM8 on its cell surface. The membrane preparation can also be isolated from a recombinant host cell, for example, a CHO or COS cell, which expresses a TRPM8 recombinantly on its cell surface. The membrane preparation can further be prepared from the biological membranes, such as the tissue membrane, plasma membrane, cell membrane, or internal organelle membrane comprising the TRPM8 channel. Methods are known to those skilled in the art for isolation and preparation of biological membrane preparations. For example, such a method can include the steps of mechanical or enzymic disruption of the tissue or cells, centrifugation to separate the membranes from other components, and resuspending the membrane fragments or vesicles in suitable buffer solution. Alternatively, the membrane-containing preparation can also be derived from artificial membranes. Purified TRPM8 protein can be reconstituted into lipid bilayers to form the artificial membrane vesicles (see Chen et al., 1996, *J. Gen. Physiol.* 108:237-250). Such type of membrane vesicle can be very specific to the channel of interest, avoiding the problem of contamination with other channels. Methods are known to those skilled in the art to prepare artificial membrane vesicles.

In another general aspect, the present invention provides methods of preparing a protein complex of the invention. The protein complex of the present invention can be prepared by a variety of methods. Specifically, a protein complex can be isolated directly from an animal tissue sample, for example a human tissue sample, containing the protein complex. A protein complex can also be isolated from host cells that recombinantly express the members of the protein complex. Alternatively, a protein complex can be constituted in vitro by combining individual members of the protein complex.

In one embodiment, a protein complex of the invention can be prepared from a tissue sample or recombinant host cells by coimmunoprecipation using an antibody immunoreactive with an interacting protein partner, or preferably an antibody selectively immunoreactive with the protein complex as will be discussed in detail below. The antibodies can be monoclonal or polyclonal. Coimmunoprecipation is a commonly used method in the art for isolating or detecting bound proteins. In this procedure, generally a serum sample or tissue or cell lysate is admixed with a suitable antibody. The protein complex bound to the antibody is precipitated and washed. The bound protein complexes are then eluted.

Alternatively, immunoaffinity chromatography and immunoblotting techniques can also be used in isolating the protein complexes from native tissue samples or recombinant host cells using an antibody immunoreactive with an interacting protein partner, or preferably an antibody selectively immunoreactive with the protein complex. For example, in protein immunoaffinity chromatography, the antibody is covalently or non-covalently coupled to a matrix (e.g., Sepharose), which is then packed into a column. Extract from a tissue sample, or lysate from recombinant cells is passed through the column where it contacts the antibodies attached to the matrix. The column is then washed with a low-salt solution to wash away the unbound or loosely (non-specifically) bound components. The protein complexes that are retained in the column can be then eluted from the column using a high-salt solution, a competitive antigen of the antibody, a chaotropic solvent, or sodium dodecyl sulfate (SDS), or the like. In immunoblotting, crude proteins samples from a tissue sample extract or recombinant host cell lysate are fractionated by polyacrylamide gel electrophoresis (PAGE) and then transferred to a membrane, e.g., nitrocellulose. Components of the protein complex can then be located on the membrane and identified by a variety of techniques, e.g., probing with specific antibodies.

In yet another embodiment, the protein complex of the present invention may be prepared from tissue samples or recombinant host cells or other suitable sources by protein affinity chromatography or affinity blotting. That is, one of the interacting protein partners is used to isolate the other interacting protein partner(s) by binding affinity thus forming protein complexes. Thus, an interacting protein partner prepared by purification from tissue samples or by recombinant expression or chemical synthesis may be bound covalently or non-covalently to a matrix, e.g., Sepharose, which is then packed into a chromatography column. The tissue sample extract or cell lysate from the recombinant cells can then be contacted with the bound protein on the matrix. A low-salt solution is used to wash off the unbound or loosely bound components, and a high-salt solution is then employed to elute the bound protein complexes in the column. In affinity blotting, crude protein samples from a tissue sample or recombinant host cell lysate can be fractionated by polyacrylamide gel electrophoresis (PAGE) and then transferred to a membrane, e.g., nitrocellulose. The purified interacting protein member is then bound to its interacting protein partner(s) on the membrane forming protein complexes, which are then isolated from the membrane.

In another embodiment, individual interacting protein partners may be isolated or purified independently from tissue samples or recombinant host cells using similar methods as described above. The individual interacting protein partners can also be synthesized using in vitro polypeptide synthesizing methods known to a person skilled in the art. The individual interacting protein partners are then combined under conditions conducive to their interaction thereby forming a protein complex of the present invention. It is noted that different protein-protein interactions may require different conditions. Several different parameters can be varied, including temperature, pH, salt concentration, reducing agent, and the like. Some minor degree of experimentation may be required to determine the optimum incubation condition, this being well within the capability of one skilled in the art once apprised of the present disclosure.

It will be apparent to skilled artisans that any recombinant expression methods may be used in the present invention for purposes of expressing the protein complexes or individual interacting proteins. Generally, a nucleic acid encoding either one or both CaM and TRPM8 can be introduced into a suitable host cell. Exemplary nucleic acid molecules that can be used in the present invention include cDNA that encodes for the full length CaM, such as SEQ ID NO: 10. And that encodes for the full length TRPM8 from human (SEQ ID:11), mouse (SEQ ID NO:12), or rat (SEQ ID NO:13). Other nucleic acid molecules that can be used in the present invention include cDNAs that encode for the active fragments or derivatives of CaM or TRPM8, such as those that encode for the active rat TRPM8 fragments having the sequence of SEQ ID NO:5, SEQ ID NO:6, SEQ ID NO:7, SEQ ID NO:8, or SEQ ID NO:9.

Typically, the nucleic acids, preferably in the form of DNA, are incorporated into a vector to form expression vectors capable of directing the production of the interacting protein member(s) once introduced into a host cell. Many types of vectors can be used for the present invention. Methods for the construction of an expression vector for purposes of this invention should be apparent to skilled artisans apprised of the present disclosure. (See generally, *Current Protocols in Molecular Biology*, Vol. 2, Ed. Ausubel, et al., Greene Publish. Assoc. & Wiley Interscience, Ch. 13, 1988; Glover, *DNA Cloning*, Vol. II, IRL Press, Wash., D.C., Ch. 3, 1986; Bitter, et al., in *Methods in Enzymology* 153:516-544 (1987); *The Molecular Biology of the Yeast Saccharomyces*, Eds. Strathern et al., Cold Spring Harbor Press, Vols. I and II, 1982; and Sambrook et al., *Molecular Cloning: A Laboratory Manual*, Cold Spring Harbor Press, 1989.)

Generally, the expression vectors include an expression cassette having a promoter operably linked to a DNA encoding an interacting protein member. The promoter can be a native promoter, i.e., the promoter found in naturally occurring cells to be responsible for the expression of the interacting protein member in the cells. Alternatively, the expression cassette can be a chimeric one, i.e., having a heterologous promoter that is not the native promoter responsible for the expression of the interacting protein member in naturally occurring cells. The expression vector may further include an origin of DNA replication for the replication of the vectors in host cells. Preferably, the expression vectors also include a replication origin for the amplification of the vectors in, e.g., *E. coli*, and selection marker(s) for selecting and maintaining only those host cells harboring the expression vectors. Additionally, the expression cassettes preferably also contain inducible elements, which function to control the transcription from the DNA encoding an interacting protein member. Other regulatory sequences such as transcriptional enhancer sequences and translation regulation sequences (e.g., Shine-Dalgarno sequence) can also be operably included in the expression cassettes. Termination sequences such as the polyadenylation signals from bovine growth hormone, SV40, lacZ and AcMNPV polyhedral protein genes may also be operably linked to the DNA encoding an interacting protein member in the expression cassettes. An epitope tag coding sequence for detection and/or purification of the expressed protein can also be operably linked to the DNA encoding an interacting protein member such that a fusion protein is expressed. Examples of useful epitope tags include, but are not limited to, influenza virus hemagglutinin (HA), Simian Virus 5 (V5), polyhistidine (6× His), c-myc, lacZ, GST, and the like. Proteins with polyhistidine tags can be easily detected and/or purified with Ni affinity columns, while specific antibodies immunoreactive with many epitope tags are generally commercially available. The expression vectors may also contain components that direct the expressed protein extracellularly or to a particular intracellular compartment. Signal peptides, nuclear localization sequences, endoplasmic reticulum retention signals, mitochondrial localization sequences, myristoylation signals, palmitoylation signals, and transmembrane sequences are examples of optional vector components that can determine the destination of expressed proteins. When it is desirable to express two or more interacting protein members in a single host cell, the DNA fragments encoding the interacting protein members may be incorporated into a single vector or different vectors.

The thus constructed expression vectors can be introduced into the host cells by any techniques known in the art, e.g., by direct DNA transformation, microinjection, electroporation, viral infection, lipofection, gene gun, and the like. The expression of the interacting protein members may be transient or stable. The expression vectors can be maintained in host cells in an extrachromosomal state, i.e., as self-replicating plasmids or viruses. Alternatively, the expression vectors can be integrated into chromosomes of the host cells by conventional techniques such as selection of stable cell lines or site-specific recombination. In stable cell lines, at least the expression cassette portion of the expression vector is integrated into a chromosome of the host cells.

The vector construct can be designed to be suitable for expression in various host cells, including but not limited to bacteria, yeast cells, plant cells, insect cells, and mammalian and human cells. Methods for preparing expression vectors for expression in different host cells should be apparent to a skilled artisan.

Homologues and fragments of the native interacting protein members can also be easily expressed using the recombinant methods described above. For example, to express a protein fragment, the DNA fragment incorporated into the expression vector can be selected such that it only encodes the protein fragment. Likewise, a specific hybrid protein can be expressed using a recombinant DNA encoding the hybrid protein. Similarly, a homologue protein may be expressed from a DNA sequence encoding the homologue protein. A homologue-encoding DNA sequence may be obtained by manipulating the native protein-encoding sequence using recombinant DNA techniques. For this purpose, random or site-directed mutagenesis can be conducted using techniques generally known in the art. To make protein derivatives, for example, the amino acid sequence of a native interacting protein member may be changed in predetermined manners by site-directed DNA mutagenesis to create or remove consensus sequences for, e.g., phosphorylation by protein kinases, glycosylation, ribosylation, myristolation, palmytoylation, ubiquitination, and the like. Alternatively, non-natural amino acids can be incorporated into an interacting protein member during the synthesis of the protein in recombinant host cells. For example, photoreactive lysine derivatives can be incorporated into an interacting protein member during translation by using a modified lysyl-tRNA. (See, e.g., Wiedmann et al., Nature, 328:830-833 (1989); Musch et al., Cell, 69:343-352 (1992). Other photoreactive amino acid derivatives can also be incorporated in a similar manner. See, e.g., High et al., J. Biol. Chem., 368:28745-28751 (1993)). Indeed, the photoreactive amino acid derivatives thus incorporated into an interacting protein member can function to cross-link the protein to its interacting protein partner in a protein complex under predetermined conditions.

In addition, derivatives of the native interacting protein members of the present invention can also be prepared by chemically linking certain moieties to amino acid side chains of the native proteins.

If desired, the homologues and derivatives thus generated can be tested to determine whether they are capable of interacting with their intended partners to form protein complexes. Testing can be conducted by e.g., the yeast two-hybrid system or other methods known in the art for detecting protein-protein interaction.

A hybrid protein as described above having any interacting pair of the protein complex of the invention, or a homologue, derivative, or fragment thereof covalently linked together by a peptide bond or a peptide linker can be expressed recombinantly from a chimeric nucleic acid, e.g., a DNA or mRNA fragment encoding the fusion protein. Accordingly, the present invention also provides a nucleic acid encoding the hybrid protein of the present invention. In addition, an expression vector having incorporated therein a nucleic acid encoding the hybrid protein of the present invention is also provided. The methods for making such chimeric nucleic acids and expression vectors containing them will be apparent to skilled artisans apprised of the present disclosure.

Purification of the expressed protein is achieved by conventional biochemical and immunochemical methods well known to those skilled in the art. Transfected eukaryotic cells or biological tissue samples can be homogenized and fractionated in appropriate conditions that will separate the different cellular components. Typically, cell lysates are run on sucrose gradients, or other materials that will separate cellular components based on size and density. Subcellular fractions are analyzed for the presence of proteins of interest with appropriate antibodies, using methods well known to those skilled in the art, such as immunoblotting or immunoprecipitation methods.

The purified protein is then used for affinity chromatography studies: it is immobilized on a matrix and loaded on a column. Extracts from cultured cells or homogenized tissue samples are then loaded on the column in appropriate buffer, and non-binding proteins are eluted. After extensive washing, binding proteins or protein complexes are eluted using various methods such as a gradient of pH or a gradient of salt concentration. Eluted proteins can then be separated by two-dimensional gel electrophoresis, eluted from the gel, and identified by micro-sequencing. All of these methods are well known to those skilled in the art.

Purified proteins of interest, individually or a complex, can also be used to generate antibodies in rabbit, mouse, rat, chicken, goat, sheep, pig, guinea pig, bovine, and horse. The methods used for antibody generation and characterization are well known to those skilled in the art. Monoclonal antibodies are also generated by conventional techniques. Single chain antibodies IG are further produced by conventional techniques.

Another aspect of the present invention relates to methods for measuring or detecting the protein complex of the present invention, in a patient sample or in a compound screening assay described infra.

In one embodiment, the concentration of a protein complex of the present invention is determined in cells, tissue, or an organ of a patient. For example, the protein complex can be isolated or purified from a patient sample obtained from cells, tissue, or an organ of the patient and the amount thereof is determined. As described above, the protein complex can be prepared from cells, tissue or organ samples by coimmunoprecipitation using an antibody immunoreactive with an interacting protein member, a bifunctional antibody that is immunoreactive with two or more interacting protein members of the protein complex, or preferably an antibody selectively immunoreactive with the protein complex. When bifunctional antibodies or antibodies immunoreactive with only free interacting protein members are used, individual interacting protein members not complexed with other proteins may also be isolated along with the protein complex containing such individual proteins. However, they can be readily separated from the protein complex using methods known in the art, e.g., size-based separation methods such as gel filtration, or by subtracting the protein complex from the mixture using an antibody specific against another individual interacting protein member. Additionally, proteins in a sample can be separated in a gel such as polyacrylamide gel and subsequently immunoblotted using an antibody immunoreactive with the protein complex.

Alternatively, the concentration of the protein complex can be determined in a sample without separation, isolation or purification. For this purpose, it is preferred that an antibody selectively immunoreactive with the specific protein complex is used in an immunoassay. For example, immunocytochemical methods can be used. Other well known antibody-based techniques can also be used including, e. g., enzyme-linked immunosorbent assay (ELISA), radioimmunoassay (RIA), immunoradiometric assays (IRMA), fluorescent immunoassays, protein A immunoassays, and immunoenzymatic assays (EMA). See e.g., U.S. Pat. Nos. 4,376,110 and 4,486,530, both of which are incorporated herein by reference.

In addition, the concentration of an individual interacting protein member of a specific protein complex can be determined in a patient sample, which can then be used as a reasonably accurate indicator of the concentration of the protein complex in the sample. For this purpose, antibodies against an individual interacting protein member of a specific complex can be used in any one of the methods described above. In a preferred embodiment, the concentration of each of the interacting protein members of a protein complex is determined in a patient sample and the relative concentration of the protein complex is then deduced.

In addition, the relative protein complex concentration in a patient can also be determined by determining the concentration of the mRNA encoding an interacting protein member of the protein complex. Preferably, each interacting protein member's mRNA concentration in a patient sample is determined. For this purpose, methods for determining mRNA concentration generally known in the art may all be used. Examples of such methods include, e.g., Northern blot assay, dot blot assay, PCR assay (preferably quantitative PCR assay), in situ hybridization assay, and the like.

The discovery of the CaM and TRPM8 protein complex of the present invention suggests that the CaM-TRPM8 protein complex can be involved in biological processes and disease pathways. Thus, aberrations in the protein complex or the individual proteins of the complex and the degree of the aberration may be indicators for the diseases or disorders. These aberrations may be used as parameters for classifying and/or staging one of the diseases or disorders. In addition, these aberrations may also be indicators for patients' response to a drug therapy.

Association between a physiological state (e.g., physiological disorder, predisposition to the disorder, a disease state, response to a drug therapy, or other physiological phenomena or phenotypes) and a specific aberration in a protein complex of the present invention or an individual interacting member thereof can be readily determined by comparative analysis of the protein complex and/or the interacting members thereof in a normal population and an abnormal or affected population. Thus, for example, one can study the concentration, localization and distribution of the CaM CMR1 protein complex, mutations in the interacting protein members of the protein complex, and/or the binding affinity between the interacting protein members in both a normal population and a population affected with a particular physiological disorder. The study results can be compared and analyzed by statistical means. Any detected statistically significant difference in the two populations would indicate an association. For example, if the concentration of the protein complex is statistically significantly higher in the affected population than in the normal population, then it can be reasonably concluded that higher concentration of the protein complex is associated with the physiological disorder.

Once an association is established between a particular type of aberration in the protein complex of the present invention or in an interacting protein member thereof and a physiological disorder or disease or predisposition to the physiological disorder or disease, the particular physiological disorder or disease or predisposition to the physiological disorder or disease can be diagnosed or detected by determining whether a patient has the particular aberration.

Accordingly, the present invention also provides a method for diagnosing in a patient a disease or physiological disorder, or a predisposition to the disease or disorder by determining whether there is any aberration in the patient with respect to the CaM-TRPM8 protein complex according to the present invention. The same protein complex is analyzed in a normal individual and is compared with the results obtained in the patient. In this manner, any protein complex aberration in the patient can be detected.

As used herein, the term "aberration" when used in the context of protein complex of the present invention means any alterations of a protein complex including increased or decreased concentration of the protein complex in a particular cell or tissue or organ or the total body, altered localization of the protein complex in cellular compartments or in locations of a tissue or organ, changes in binding affinity of an interacting protein member of the protein complex, mutations in an interacting protein member or the gene encoding the protein, and the like. As will be apparent to a skilled artisan, the term "aberration" is used in a relative sense. That is, an aberration is relative to a normal condition.

As used herein, the term "diagnosis" means detecting a disease or disorder or determining the stage or degree of a disease or disorder. The term "diagnosis" also encompasses detecting a predisposition to a disease or disorder, determining the therapeutic effect of a drug therapy, or predicting the pattern of response to a drug therapy or xenobiotics. The diagnosis methods of the present invention may be used independently, or in combination with other diagnosing and/or staging methods known in the medical art for a particular disease or disorder.

Thus, in one embodiment, the method of diagnosis is conducted by detecting, in a patient, the concentration of the CaM-TRPM8 protein complex using any one of the methods described above, and determining whether the patient has an aberrant concentration of the protein complex.

The diagnosis may also be based on the determination of the concentrations of one or more interacting protein members (at the protein, cDNA or mRNA level) of a protein complex of the present invention. An aberrant concentration of an interacting protein member may indicate a physiological disorder or a predisposition to a physiological disorder.

In another embodiment, the method of diagnosis comprises determining, in a patient, the cellular localization, or tissue or organ distribution of a protein complex of the present invention and determining whether the patient has an aberrant localization or distribution of the protein complex. For example, immunocytochemical or immunohistochemical assays can be performed on a cell, tissue or organ sample from a patient using an antibody selectively immunoreactive with a protein complex of the present invention. Antibodies immunoreactive with both an individual interacting protein member and a protein complex containing the protein member may also be used, in which case it is preferred that antibodies immunoreactive with other interacting protein members are also used in the assay. In addition, nucleic acid probes may also be used in in situ hybridization assays to detect the localization or distribution of the mRNAs encoding the interacting protein members of a protein complex. Preferably, the mRNA encoding each interacting protein member of a protein complex is detected concurrently.

In yet another embodiment, the method of diagnosis of the present invention comprises detecting any mutations in one or more interacting protein members of a protein complex of the present invention. In particular, it is desirable to determine whether the interacting protein members have any mutations that will lead to, or are associated with, changes in the functional activity of the proteins or changes in their binding affinity to other interacting protein members in forming a protein complex of the present invention. Examples of such mutations include but are not limited to, e.g., deletions, insertions and rearrangements in the genes encoding the protein members, and nucleotide or amino acid substitutions and the like. In a preferred embodiment, the domains of the interacting protein members that are responsible for the protein-protein interactions, and lead to protein complex formation, are screened to detect any mutations therein. For example, genomic DNA or cDNA encoding an interacting protein member can be prepared from a patient sample, and sequenced. The thus obtained sequence may be compared with known wild-type sequences to identify any mutations. Alternatively, an interacting protein member may be purified from a patient sample and analyzed by protein sequencing or mass spectrometry to detect any amino acid sequence changes. Any methods known in the art for detecting mutations may be used, as will be apparent to skilled artisans apprised of the present disclosure.

In another embodiment, the method of diagnosis includes determining the binding constant of the interacting protein members of one or more protein complexes. For example, the interacting protein members can be obtained from a patient by direct purification or by recombinant expression from genomic DNAs or cDNAs prepared from a patient sample encoding the interacting protein members. Binding constants represent the strength of the protein-protein interaction between the interacting protein members in a protein complex. Thus, by measuring binding constants, subtle aberrations in binding affinity may be detected.

A number of methods known in the art for estimating and determining binding constants in protein-protein interactions are reviewed in (Phizicky and Fields, et al., *Microbiol. Rev.,* 59:94-123 (1995)), which is incorporated herein by reference. For example, protein affinity chromatography may be used. First, columns are prepared with different concentrations of an interacting protein member, which is covalently bound to the columns. Then a preparation of an interacting protein partner is run through the column and washed with buffer. The interacting protein partner bound to the interacting protein member linked to the column is then eluted. A binding constant is then estimated based on the concentrations of the bound protein and the eluted protein. Alternatively, the method of sedimentation through gradients monitors the rate of sedimentation of a mixture of proteins through gradients of glycerol or sucrose. At concentrations above the binding constant, proteins can sediment as a protein complex. Thus, binding constant can be calculated based on the concentrations. Other suitable methods known in the art for estimating binding constant include but are not limited to gel filtration column such as nonequilibrium "small-zone" gel filtration columns (See e.g., Gill et al., *J. Mol. Biol.,* 220:307-324 (1991)), the Hummel-Dreyer method of equilibrium gel filtration (See e.g., Hummel and Dreyer, *Biochim. Biophys. Acta,* 63:530-532 (1962)) and large-zone equilibrium gel filtration (See e.g., Gilbert and Kellett, *J. Biol. Chem.,* 246: 6079-6086 (1971)), sedimentation equilibrium (See e.g., Rivas and Minton, *Trends Biochem.,* 18:284-287 (1993)), fluorescence methods such as fluorescence spectrum (See e.g., Otto-Bruc et al., *Biochemistry,* 32:8632-8645 (1993)) and fluorescence polarization or anisotropy with tagged molecules (See e.g., Weiel and Hershey, *Biochemistry,* 20:5859-5865 (1981)), solution equilibrium measured with immobilized binding protein (See e.g., Nelson and Long, *Biochemistry,* 30:2384-2390 (1991)), and surface plasmon resonance (See e.g., Panayotou et al., *Mol. Cell. Biol.,* 13:3567-3576 (1993)).

In another embodiment, the diagnosis method of the present invention comprises detecting protein-protein interactions in functional assay systems such as the yeast two-hybrid system. Accordingly, to determine the protein-protein interaction between two interacting protein members that normally form a protein complex in normal individuals, cDNAs encoding the interacting protein members can be isolated from a patient to be diagnosed. The thus cloned cDNAs or fragments thereof can be subcloned into vectors for use in yeast two-hybrid systems. Preferably a reverse yeast two-hybrid system is used such that failure of interaction between the proteins may be positively detected. The use of yeast two-hybrid systems or other systems for detecting protein-protein interactions is known in the art and is described infra.

A kit may be used for conducting the diagnosis methods of the present invention. Typically, the kit should contain, in a carrier or compartmentalized container, reagents useful in any of the above-described embodiments of the diagnosis method. The carrier can be a container or support, in the form of, e.g., bag, box, tube, rack, and is optionally compartmentalized. The carrier may define an enclosed confinement for safety purposes during shipment and storage. In one embodiment, the kit includes an antibody selectively immunoreactive with a protein complex of the present invention. In addition, antibodies against individual interacting protein members of the protein complexes may also be included. The antibodies may be labeled with a detectable marker such as radioactive isotopes, or enzymatic or fluorescence markers. Alternatively secondary antibodies such as labeled anti-IgG and the like may be included for detection purposes. Optionally, the kit can include one or more of the protein complexes of the present invention prepared or purified from a normal individual or an individual afflicted with a physiological disorder associated with an aberration in the protein complexes or an interacting protein member thereof. In addition, the kit may further include one or more of the interacting protein members of the protein complexes of the present invention prepared or purified from a normal individual or an individual afflicted with a physiological disorder associated with an aberration in the protein complexes or an interacting protein member thereof. Suitable oligonucleotide primers useful in the amplification of the genes or cDNAs for the interacting protein members may also be provided in the kit. In particular, in a preferred embodiment, the kit includes a first oligonucleotide selectively hybridizable to the mRNA or cDNA encoding one member of an interacting pair of proteins and a second oligonucleotide selectively hybridizable to the mRNA or cDNA encoding the other of the interacting pair. Additional oligonucleotides hybridizing to a region of the genes encoding an interacting pair of proteins may also be included. Such oligonucleotides may be used as PCR primers for, e.g., quantitative PCR amplification of mRNAs encoding the interacting proteins, or as hybridizing probes for detecting the mRNAs. The oligonucleotides may have a length of from about 8 nucleotides to about 100 nucleotides, preferably from about 12 to about 50 nucleotides, and more preferably from about 15 to about 30 nucleotides. In addition, the kit may also contain oligonucleotides that can be used as hybridization probes for detecting the cDNAs or mRNAs encoding the interacting protein members. Preferably, instructions for using the kit or reagents contained therein are also included in the kit.

The discovery of the CaM and TRPM8 protein complex of the present invention allows the design of novel methods to identify compounds that increase or decrease the biological activity of TRPM8, a nociceptor that can serve as a therapeutic target for the identification of drugs useful in treating pain, inflammation and skin disorders. The present discovery allows screening assays to be setup that does not utilize the measurements of the TRPM8 channel conductivity, which can be cumbersome. Consequently, one additional general aspect of the present invention relates to methods for identifying a modulator for the CaM-TRPM8 protein complex, which in turn increases or decreases the biological activity of TRPM8.

The term "modulator" encompasses any compounds that can cause any form of alteration of the biological activities or functions of the CaM-TRPM8 protein complex, including, e.g., enhancing or reducing their biological activities, increasing or decreasing their stability, altering their affinity or specificity to certain other biological molecules, etc. For example, a modulator can be an "interaction antagonist" or an "interaction agonist". As used herein, the term "interaction antagonist" means a compound that interferes with, blocks, disrupts or destabilizes a protein-protein interaction; blocks or interferes with the formation of a protein complex; or destabilizes, disrupts or dissociates an existing protein complex. The term "interaction agonist" as used herein means a compound that triggers, initiates, propagates, nucleates, or otherwise enhances the formation of a protein-protein interaction; triggers, initiates, propagates, nucleates, or otherwise enhances the formation of a protein complex; or stabilizes an existing protein complex.

The compound identification methods can be performed using conventional laboratory formats or in assays adapted for high throughput. The term "high throughput" refers to an assay design that allows easy screening of multiple samples simultaneously and/or in rapid succession, and can include the capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, greater numbers of samples can be processed using the design of the present invention.

Any test compounds may be screened in the screening assays of the present invention to select modulators of the protein complex of the invention. By the term "selecting" or "select" compounds it is intended to encompass both (a) choosing compounds from a group previously unknown to be modulators of a protein complex or interacting protein members thereof; and (b) testing compounds that are known to be capable of binding, or modulating the functions and activities of, a protein complex or interacting protein members thereof. Both types of compounds are generally referred to herein as "test compounds" or "candidate compound". The candidate compounds encompass numerous chemical classes, including but not limited to, small organic or inorganic compounds, natural or synthetic molecules, such as antibodies, proteins or fragments thereof, antisense nucleotides, interfering RNA (iRNA) and ribozymes, and derivatives, mimetics and analogs thereof. Preferably, they are small organic compounds, i.e., those having a molecular weight of no greater than 10,000 daltons, more preferably less than 5,000 daltons. Preferably, the test compounds are provided in library formats known in the art, e.g., in chemically synthesized libraries (See generally, Gordan et al. *J. Med. Chem.*, 37:1385-1401 (1994)), recombinantly expressed libraries (e.g., phage display libraries), and in vitro translation-based libraries (e.g., ribosome display libraries).

Candidate compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound typically is a DNA or RNA molecule, although modified nucleic acids having non-natural bonds or subunits are also contemplated.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including biological libraries; spatially addressable parallel solid phase or solution phase libraries: synthetic library methods requiring deconvolution; the "one-bead one-compound" library method; and synthetic library methods using affinity chromatography selection (Lam (1997) *Anticancer Drug Des.* 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents can be subjected to directed or random chemical modifications such as acylation, alkylation, esterification, amidation, etc. to produce structural analogs of the agents. Candidate compounds can be selected randomly or can be based on existing compounds that bind to and/or modulate the function of TRPM8 activity. Therefore, a source of candidate agents is one or more than one library of molecules based on one or more than one known compound that increases or decreases TRPM8 channel conductivity in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing compounds.

A variety of other reagents also can be included in the mixture. These include reagents such as salts, buffers, neutral proteins (e.g., albumin), detergents, etc. that can be used to facilitate optimal protein-protein and/or protein-nucleic acid binding. Such a reagent can also reduce non-specific or background interactions of the reaction components. Other reagents that improve the efficiency of the assay such as nuclease inhibitors, antimicrobial agents, and the like can also be used.

Examples of methods for the synthesis of molecular libraries can be found in the art, for example in: Zuckermann et al. (1994). *J Med. Chem.* 37:2678. Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. No. 5,571,698), plasmids (Cull et al. (1992) *Proc. Natl. Acad. Sci. USA* 89:1865-1869) or phage (see e.g., Scott and Smith (1990) *Science* 249:3 86-390).

The selected compounds can be tested for their ability to modulate (i.e., interfere with or strengthen) the interaction between the TRPM8 and CaM of the protein complex of present invention. The compounds can be further tested for their ability to increase or decrease the channel conductivity of the TRPM8. In addition, the compounds can be tested in an animal model for pain, inflammation, or skin disorder, etc.

An "interaction" between two protein domains, fragments or complete proteins can be determined by a number of methods. For example, an interaction is detectable by any commonly accepted approaches, including functional assays such as the yeast two-hybrid systems. Protein-protein interactions can also be determined by various biophysical and biochemical approaches based on the affinity binding between the two interacting partners. Such methods generally known in the art include, but are not limited to, protein affinity chromatography, affinity blotting, co-immunoprecipitation, subcellular fractionation and isolation of large molecular complexes, and the like. Each of these methods is well characterized and can be readily performed by one skilled in the art. See, e.g., U.S. Pat. Nos. 5,622,852 and 5,773,218, and PCT published applications No. WO 97/27296 and WO 99/65939, each of which is incorporated herein by reference. The binding constant for two interacting proteins, which reflects the strength or quality of the interaction, can also be determined using methods known in the art, including surface plasmon resonance and isothermal titration calorimetry binding analyses. See Phizicky and Fields, *Microbiol. Rev.,* 59:94-123 (1995).

The test compounds may be screened in an in vitro assay to identify compounds capable of binding the CaM-TRPM8 protein complex of the present invention. For this purpose, a test compound is contacted with a protein complex under conditions and for a time sufficient to allow specific interaction between the test compound and the target components to occur, thereby resulting in the binding of the compound to the target, and the formation of a complex. Subsequently, the binding event is detected.

In one particular embodiment, the protein complex is immobilized on a solid support (such as a protein microchip) or on a cell surface. For example, the protein complex can be immobilized directly onto a microchip substrate such as glass slides or onto multi-well plates using non-neutralizing antibodies, i.e., antibodies capable of binding to the complex but do not substantially affect its biological activities. Test compounds can be contacted with the immobilized protein complex to allow binding to occur under standard binding assay conditions. The test compounds can be labeled with a detectable marker using well-known labeling techniques. For example, U.S. Pat. No. 5,741,713 discloses combinatorial libraries of biochemical compounds labeled with NMR active isotopes. To identify compound binding to the protein complex, one can measure the labeling on the compound. When combinatorial libraries of organic non-peptide non-nucleic acid compounds are screened, it is preferred that labeled or encoded (or "tagged") combinatorial libraries are used to allow rapid decoding of lead structures. This is especially important because, unlike biological libraries, individual compounds found in chemical libraries cannot be amplified by self-amplification. Tagged combinatorial libraries are provided in, e.g., Borchardt and Still, *J. Am. Chem. Soc.,* 116: 373-374 (1994) and Moran et al., *J. Am. Chem. Soc.,* 117: 10787-10788 (1995), both of which are incorporated herein by reference.

In an alternative embodiment, the test compounds can be immobilized on a solid support, e.g., forming a microarray of test compounds. The protein complex is then contacted with the test compounds. The protein complex can be labeled with any suitable detection marker. For example, the complex can be labeled with radioactive isotopes or fluorescence marker before binding reaction occurs. Alternatively, after the binding reactions, antibodies that are immunoreactive with the complex and are labeled with radioactive materials, fluorescence markers, enzymes, or labeled secondary anti-Ig antibodies can be used to detect any bound complex thus identifying the binding compound. One example of this embodiment is the protein probing method. That is, the protein complex provided in accordance with the present invention is used as a probe to screen expression libraries of proteins or random peptides. The expression libraries can be phage display libraries, in vitro translation-based libraries, or ordinary expression cDNA libraries. The libraries may be immobilized on a solid support such as nitrocellulose filters. See e.g., Sikela and Hahn, *Proc. Natl. Acad. Sci. USA,* 84:3038-3042 (1987). The probe may be labeled with a radioactive isotope or a fluorescence marker. Alternatively, the probe can be biotinylated and detected with a streptavidinalkaline phosphatase conjugate. More conveniently, the bound probe may be detected with an antibody.

In vitro assays can also be performed to identify compounds capable of increasing or decreasing the interaction between CaM and TRPM8 in a protein complex of the present invention. The assays can be conducted in a manner similar to the binding assays described above. For example, the level of the CaM-TRPM8 protein complex can be detected by an antibody selectively immunoreactive with the protein complex formed by those two proteins. Thus, after incubation of the CaM-TRPM8 protein complex with a test compound, an immunoprecipitation assay can be conducted with the antibody. If the test compound disrupts the protein complex, then the amount of immunoprecipitated protein complex in this assay will be significantly less than that in a control assay in which the same protein complex is not contacted with the test compound. Similarly two proteins, i.e., CaM and TRPM8 or active fragments or derivatives thereof, can be incubated together with a test compound. A protein complex formed by the two proteins can be detected by the selectively immunoreactive antibody. The amount of protein complex can be compared to that formed in the absence of the test compound. If the test compound enhances the formation of the protein complex, then the amount of immunoprecipitated protein complex in this assay will be significantly more than that in a control assay in which the two proteins are not contacted with the test compound. Various other detection methods are suitable for measuring the level of the CaM-TRPM8 protein complex as described supra.

In a specific embodiment, TRPM8 in an isolated cell membrane and is contacted with test compounds. Calmodulin can be labeled with a detectable marker such as radioactive materials or fluorescence markers using label techniques known in the art. The labeled CaM is allowed to contact the TRPM8. After washing away unbound CaM, levels of TRPM8-CaM protein complex formed are detected by the labeling on the cell membrane. The ability of the test compounds to modulate the interaction between CaM and TRPM8 is determined by comparing the level of TRPM8-CaM complex formed when TRPM8 is contacted with test compounds to the level formed in the absence of test compounds. Alternatively, as will be apparent to skilled artisans, levels of TRPM8-CaM protein complex formed can also be detected with labeled antibody against CaM, or by an antibody specific to a polypeptide that is fused to CaM.

A detectable epitope tag can be fused to CaM, TRPM8, or an active fragment or derivative thereof to facilitate the detection of the protein complex of the invention. Suitable examples of such epitope tags include sequences derived from, e.g., influenza virus hemagglutinin (HA), Simian Virus 5 (V5), polyhistidine (6×His), c-myc, lacZ, GST, and the like.

In another embodiment, fluorescent resonance energy transfer (FRET) is used to screen for modulators of the protein complex of the present invention. FRET assays measure the energy transfer of a fluorescent label to another fluorescent label. Fluorescent labels absorb light preferentially at one wavelength and emit light preferentially at a second wavelength. FRET assays utilize this characteristic by selecting a fluorescent label, called a donor fluorophore, that emits light preferentially at the wavelength a second label, called the acceptor fluorophore, preferentially absorbs light. The proximity of the donor and acceptor fluorophore can be determined by measuring the energy transfer from the donor fluorophore to the acceptor fluorophore. Measuring the energy transfer is performed by shining light on a solution containing acceptor and donor fluorophores at the wavelength the donor fluorophore absorbs light and measuring fluorescence at the wavelength the acceptor fluorophore emits light. The amount of fluorescence of the acceptor fluorophore indicates the proximity of the donor and acceptor fluorophores.

In an illustrative FRET assay, TRPM8 or an active fragment or derivative of TRPM8 is labeled with a donor fluorophore such as $TP^{3+}$, and CaM or an active fragment or derivative of CaM is labeled with an acceptor fluorephore such as BODIPY-TMR. These fluorescently labeled members of the protein complex of the invention are put together in a solution. Light at the wavelength that $TP^{3+}$ preferentially absorbs is shined on the solution and the fluorescence of the solution is measured at the wavelength that BODIPY-TMR preferentially emits. A test compound is then added to the solution. Light at the wavelength that $TP^{3+}$ preferentially absorbs is shined on the solution and the fluorescence of the solution is measured at the wavelength that BODIPY-TMR preferentially emits. If the test compound decreases the fluorescence of the solution compared to that without the test compound, the test compound decreases the interaction between CaM and TRPM8.

In another embodiment, fluorescence polarization (FP) measurements is used to screen for modulators of the protein complex of the present invention. FP measurements have been used to provide information on molecular orientation and mobility and processes that modulate them, including receptor-ligand interactions, proteolysis, protein-DNA interactions, membrane fluidity and muscle contraction. FP measurements have long been a valuable biophysical research tool for investigating processes such as membrane lipid mobility, myosin reorientation and protein-protein interactions at the molecular level (see for example, Jameson et al., *Methods Enzymol*, 1995, 246:283-300). Immunoassays that have been developed and used extensively for clinical diagnostics represent the largest group of bioanalytical applications. The more recent advent of microplate readers equipped with polarizing optics has led to the adoption of fluorescence polarization as a readout mode for high-throughput screening.

In an exemplary FP assay, dye molecules with their absorption transition vectors aligned parallel to the electric vector of linearly polarized light (along the vertical page axis) are selectively excited. For dyes attached to small, rapidly rotating molecules, the initially photoselected orientational distribution becomes randomized prior to emission, resulting in low fluorescence polarization. Conversely, binding of the low molecular weight tracer to a large, slowly rotating molecule results in high fluorescence polarization. Fluorescence polarization therefore provides a direct readout of the extent of tracer binding to proteins, nucleic acids and other biopolymers. Dyes and other reagents for FP Assays are commercially available, from example, from Invitrogen.

In a preferred embodiment, one of the yeast two-hybrid systems or their analogous or derivative forms can be used to identify a modulator for the CaM-TRPM8 protein complex. Examples of suitable two-hybrid systems known in the art include, but are not limited to, those disclosed in U.S. Pat. Nos. 5,283,173; 5,525,490; 5,585, 245; 5, 637,463; 5,695, 941; 5,733,726; 5,776,689; 5,885,779; 5,905,025; 6,037,136; 6,057,101; 6,114,111; and Bartel and Fields, eds., *The Yeast Two-Hybrid System*, Oxford University Press, New York, N.Y., 1997, all of which are incorporated herein by reference.

Typically, in a classic transcription-based two-hybrid assay, two chimeric genes are prepared encoding two fusion proteins: one contains a transcription activation domain fused to an interacting protein member of a protein complex of the present invention or an interaction domain or fragment of the interacting protein member, while the other fusion protein includes a DNA binding domain fused to another interacting protein member of the protein complex or a fragment or interaction domain thereof. For the purpose of convenience, the two interacting protein members, fragments or interaction domains thereof are referred to as "bait fusion protein" and "prey fusion protein," respectively. The chimeric genes encoding the fusion proteins are termed "bait chimeric gene" and "prey chimeric gene," respectively. Typically, a "bait vector" and a "prey vector" are provided for the expression of a bait chimeric gene and a prey chimeric gene, respectively.

Many types of vectors can be used in a transcription-based two-hybrid assay. Methods for the construction of bait vectors and prey vectors should be apparent to skilled artisans in the art apprised of the present disclosure. See generally, *Current Protocols in Molecular Biology*, Vol. 2, Ed. Ausubel, et al., Greene Publish. Assoc. & Wiley Interscience, Ch. 13, 1988; Glover, *DNA Cloning*, Vol. II, IRL Press, Wash., D.C., Ch. 3, 1986; Bitter, et al., in *Methods in Enzymology* 153:516-544 (1987); *The Molecular Biology of the Yeast Saccharomyces*, Eds. Strathern et al., Cold Spring Harbor Press, Vols. I and II, 1982; and Rothstein in *DNA Cloning: A Practical Approach*, Vol. II, Ed. D M Glover, IRL Press, Wash., D.C., 1986.

Generally, the bait and prey vectors include an expression cassette having a promoter operably linked to a chimeric gene for the transcription of the chimeric gene. The vectors may also include an origin of DNA replication for the replication of the vectors in host cells and a replication origin for the amplification of the vectors in, e. g., *E. coli*, and selection marker(s) for selecting and maintaining only those host cells harboring the vectors. Additionally, the expression cassette preferably also contains inducible elements, which function to control the expression of a chimeric gene. Making the expression of the chimeric genes inducible and controllable is especially important in the event that the fusion proteins or components thereof are toxic to the host cells. Other regulatory sequences such as transcriptional enhancer sequences and translation regulation sequences (e.g., Shine-Dalgarno sequence) can also be included in the expression cassette. Termination sequences such as the bovine growth hormone, SV40, lacZ and AcMNPV polyhedral polyadenylation signals may also be operably linked to a chimeric gene in the expression cassette. An epitope tag coding sequence for detection and/or purification of the fusion proteins can also be operably linked to the chimeric gene in the expression cassette. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. The vectors can be introduced into the host cells by any techniques known in the art, e.g., by direct DNA transformation, microinjection, electroporation, viral infection, lipofection, gene gun, and the like. The bait and prey vectors can be maintained in host cells in an extrachromosomal state, i.e., as self-replicating plasmids or viruses. Alternatively, one or both vectors can be integrated into chromosomes of the host cells by conventional techniques such as selection of stable cell lines or site-specific recombination.

Although the two-hybrid assay was originated in yeast, analogous assays have since been developed to be conducted in many different host cells, including but not limited to bacteria, yeast cells, plant cells, insect cells, and mammalian cells. A skilled artisan will recognize that the designs of the vectors can vary with the host cells used.

In one embodiment, the assay is conducted in prokaryotic cells such as *Escherichia coli, Salmonella, Klebsiella, Pseudomonas, Caulobacter,* and *Rhizobium*. Suitable origins of replication for the expression vectors useful in this embodiment of the present invention include, e.g., the ColE1, pSC101, and M13 origins of replication. Examples of suitable promoters include, for example, the T7 promoter, the lacZ promoter, and the like. In addition, inducible promoters are also useful in modulating the expression of the chimeric genes. For example, the lac operon from bacteriophage lambda plac5 is well known in the art and is inducible by the addition of IPTG to the growth medium. Other known inducible promoters useful in a bacteria expression system include pL of bacteriophage λ, the trp promoter, and hybrid promoters such as the tac promoter, and the like.

In addition, selection marker sequences for selecting and maintaining only those prokaryotic cells expressing the desirable fusion proteins should also be incorporated into the expression vectors. Numerous selection markers including auxotrophic markers and antibiotic resistance markers are known in the art and can all be useful for purposes of this invention. For example, the bla gene, which confers ampicillin resistance, is the most commonly used selection marker in prokaryotic expression vectors. Other suitable markers include genes that confer neomycin, kanamycin, or hygromycin resistance to the host cells. In fact, many vectors are commercially available from vendors such as Invitrogen Corp. of Carlsbad, Calif., Clontech Corp. of Palo Alto, Calif., and Stratagene Corp. of La Jolla, Calif., and Promega Corp. of Madison, Wis. These commercially available vectors, e.g., pBR322, pSPORT, pBluescriptIISK, pcDNAI, and pcDNAII all have a multiple cloning site into which the chimeric genes of the present invention can be conveniently inserted using conventional recombinant techniques. The constructed expression vectors can be introduced into host cells by various transformation or transfection techniques generally known in the art.

In another embodiment, mammalian cells are used as host cells for the expression of the fusion proteins and detection of protein-protein interactions. For this purpose, virtually any mammalian cells can be used including normal tissue cells, stable cell lines, and transformed tumor cells. Conveniently, mammalian cell lines such as CHO cells, Jurkat T cells, NIH 3T3 cells, HEK-293 cells, CV-1 cells, COS-1 cells, HeLa cells, VERO cells, MDCK cells, WI38 cells, and the like are used. Mammalian expression vectors are well known in the art and many are commercially available. Examples of suitable promoters for the transcription of the chimeric genes in mammalian cells include viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Inducible promoters can also be used. Suitable inducible promoters include, for example, the tetracycline responsive element (TRE) (See Gossen et al., *Proc. Natl. Acad. Sci. USA,* 89:5547-5551 (1992)), metallothionein IIA promoter, ecdysone-responsive promoter, and heat shock promoters. Suitable origins of replication for the replication and maintenance of the expression vectors in mammalian cells include, e.g., the Epstein Barr origin of replication in the presence of the Epstein Barr nuclear antigen (see Sugden et al., *Mole. Cell. Biol.,* 5:410-413 (1985)) and the SV40 origin of replication in the presence of the SV40 T antigen (which is present in COS-1 and COS-7 cells) (see Margolskee et al.,

*Mole. Cell. Biol.*, 8:2837 (1988)). Suitable selection markers include, but are not limited to, genes conferring resistance to neomycin, hygromycin, zeocin, and the like. Many commercially available mammalian expression vectors may be useful for the present invention, including, e.g., pCEP4, pcDNAI, pIND, pSecTag2, pVAX1, pcDNA3.1, and pBI-EGFP, and pDisplay. The vectors can be introduced into mammalian cells using any known techniques such as calcium phosphate precipitation, lipofection, electroporation, and the like. The bait vector and prey vector can be co-transformed into the same cell or, alternatively, introduced into two different cells which are subsequently fused together by cell fusion or other suitable techniques.

Viral expression vectors, which permit introduction of recombinant genes into cells by viral infection, can also be used for the expression of the fusion proteins. Viral expression vectors generally known in the art include viral vectors based on adenovirus, bovine papilloma virus, murine stem cell virus (MSCV), MFG virus, and retrovirus. See Sarver, et al., *Mol. Cell. Biol.*, 1: 486 (1981); Logan & Shenk, *Proc. Natl. Acad. Sci. USA*, 81:3655-3659 (1984); Mackett, et al., *Proc. Natl. Acad. Sci. USA*, 79:7415-7419 (1982); Mackett, et al., *J. Virol.*, 49:857-864 (1984); Panicali, et al., *Proc. Natl. Acad. Sci. USA*, 79:4927-4931 (1982); Cone & Mulligan, *Proc. Natl. Acad. Sci. USA*, 81:6349-6353 (1984); Mann et al., *Cell*, 33:153-159 (1993); Pear et al., *Proc. Natl. Acad. Sci. USA*, 90:8392-8396 (1993); Kitamura et al., *Proc. Natl. Acad. Sci. USA*, 92:9146-9150 (1995); Kinsella et al., *Human Gene Therapy*, 7:1405-1413 (1996); Hofmann et al., *Proc. Natl. Acad. Sci. USA*, 93:5185-5190 (1996); Choate et al., *Human Gene Therapy*, 7:2247 (1996); WO 94/19478; Hawley et al., *Gene Therapy*, 1:136 (1994) and Rivere et al., *Genetics*, 92:6733 (1995), all of which are incorporated by reference.

Generally, to construct a viral vector, a chimeric gene according to the present invention can be operably linked to a suitable promoter. The promoter-chimeric gene construct is then inserted into a non-essential region of the viral vector, typically a modified viral genome. This results in a viable recombinant virus capable of expressing the fusion protein encoded by the chimeric gene in infected host cells. Once in the host cell, the recombinant virus typically is integrated into the genome of the host cell. However, recombinant bovine papilloma viruses typically replicate and remain as extrachromosomal elements.

In another embodiment, the detection assays of the present invention are conducted in plant cell systems. Methods for expressing exogenous proteins in plant cells are well known in the art. See generally, Weissbach & Weissbach, *Methods for Plant Molecular Biology*, Academic Press, NY, 1988; Grierson & Corey, *Plant Molecular Biology*, 2d Ed., Blackie, London, 1988. Recombinant virus expression vectors based on, e.g., cauliflower mosaic virus (CaMV) or tobacco mosaic virus (TMV) can all be used. Alternatively, recombinant plasmid expression vectors such as Ti plasmid vectors and R1 plasmid vectors are also useful. The chimeric genes encoding the fusion proteins of the present invention can be conveniently cloned into the expression vectors and placed under control of a viral promoter such as the $^{35}$S RNA and 19S RNA promoters of CaMV or the coat protein promoter of TMV, or of a plant promoter, e.g., the promoter of the small subunit of RUBISCO and heat shock promoters (e.g., soybean hsp17.5-E or hsp17.3-B promoters).

In addition, the in vivo assay of the present invention can also be conducted in insect cells, e.g., *Spodoptera frugiperda* cells, using a baculovirus expression system. Expression vectors and host cells useful in this system are well known in the art and are generally available from various commercial vendors. For example, the chimeric genes of the present invention can be conveniently cloned into a non-essential region (e.g., the polyhedrin gene) of an *Autographa californica* nuclear polyhedrosis virus (AcNPV) vector and placed under control of an AcNPV promoter (e.g., the polyhedrin promoter). The non-occluded recombinant viruses thus generated can be used to infect host cells such as *Spodoptera frugiperda* cells in which the chimeric genes are expressed. See U.S. Pat. No. 4,215,051.

In a preferred embodiment of the present invention, the fusion proteins are expressed in a yeast expression system using yeasts such as *Saccharomyces cerevisiae*, *Hansenula polymorpha*, *Pichia pastoris*, and *Schizosaccharomyces pombe* as host cells. The expression of recombinant proteins in yeasts is a well-developed field, and the techniques useful in this respect are disclosed in detail in *The Molecular Biology of the Yeast Saccharomyces*, Eds. Strathem et al., Vols. I and II, Cold Spring Harbor Press, 1982; Ausubel et al., *Current Protocols in Molecular Biology*, New York, Wiley, 1994; and Guthrie and Fink, *Guide to Yeast Genetics and Molecular Biology*, in *Methods in Enzymology*, Vol. 194, 1991, all of which are incorporated herein by reference. Sudbery, *Curr. Opin. Biotech.*, 7:517-524 (1996) reviews the successes in the art of expressing recombinant proteins in various yeast species; the entire content and references cited therein are incorporated herein by reference. In addition, Bartel and Fields, eds., *The Yeast Two-Hybrid System*, Oxford University Press, New York, N.Y., 1997 contains extensive discussions of recombinant expression of fusion proteins in yeasts in the context of various yeast two-hybrid systems, and cites numerous relevant references. These and other methods known in the art can all be used for purposes of the present invention. The application of such methods to the present invention should be apparent to a skilled artisan apprised of the present disclosure.

Generally, each of the two chimeric genes is included in a separate expression vector (bait vector and prey vector). Both vectors can be co-transformed into a single yeast host cell. As will be apparent to a skilled artisan, it is also possible to express both chimeric genes from a single vector. In a preferred embodiment, the bait vector and prey vector are introduced into two haploid yeast cells of opposite mating types, e.g., a-type and α-type, respectively. The two haploid cells can be mated at a desired time to form a diploid cell expressing both chimeric genes.

Generally, the bait and prey vectors for recombinant expression in yeast include a yeast replication origin such as the 2µ origin or the ARSH4 sequence for the replication and maintenance of the vectors in yeast cells. Preferably, the vectors also have a bacteria origin of replication (e.g., ColE1) and a bacteria selection marker (e.g., amp$^R$ marker, i.e., bla gene). Optionally, the CEN6 centromeric sequence is included to control the replication of the vectors in yeast cells. Any constitutive or inducible promoters capable of driving gene transcription in yeast cells may be employed to control the expression of the chimeric genes. Such promoters are operably linked to the chimeric genes. Examples of suitable constitutive promoters include but are not limited to the yeast ADH1, PGK1, TEF2, GPD1, HIS3, and CYC1 promoters. Examples of suitable inducible promoters include but are not limited to the yeast GAL1 (inducible by galactose), CUP1 (inducible by Cu$^{++}$), and FUS1 (inducible by pheromone) promoters; the AOX/MOX promoter from *H. polymorpha* and *P. pastoris* (repressed by glucose or ethanol and induced by methanol); chimeric promoters such as those that contain LexA operators (inducible by LexA-containing transcription factors); and the like. Inducible promoters are preferred when the fusion proteins encoded by the chimeric genes are toxic to the host cells. If it is desirable, certain transcription repressing sequences such as the upstream repressing sequence (URS) from SPO13 promoter can be operably linked to the promoter sequence, e.g., to the 5' end of the promoter region. Such upstream repressing sequences function to fine-tune the expression level of the chimeric genes.

Preferably, a transcriptional termination signal is operably linked to the chimeric genes in the vectors. Generally, transcriptional termination signal sequences derived from, e.g., the CYC1 and ADH1 genes can be used.

Additionally, it is preferred that the bait vector and prey vector contain one or more selectable markers for the selection and maintenance of only those yeast cells that harbor one or both chimeric genes. Any selectable markers known in the art can be used for purposes of this invention so long as yeast cells expressing the chimeric gene(s) can be positively identified or negatively selected. Examples of markers that can be positively identified are those based on color assays, including the lacZ gene (which encodes β-galactosidase), the firefly luciferase gene, secreted alkaline phosphatase, horseradish peroxidase, the blue fluorescent protein (BFP), and the green fluorescent protein (GFP) gene (see Cubitt et al., *Trends Biochem. Sci.*, 20:448-455 (1995)). Other markers allowing detection by fluorescence, chemiluminescence, UV absorption, infrared radiation, and the like can also be used. Among the markers that can be selected are auxotrophic markers including, but not limited to, URA3, HIS3, TRP1, LEU2, LYS2, ADE2, and the like. Typically, for purposes of auxotrophic selection, the yeast host cells transformed with bait vector and/or prey vector are cultured in a medium lacking a particular nutrient. Other selectable markers are not based on auxotrophies, but rather on resistance or sensitivity to an antibiotic or other xenobiotic. Examples of such markers include but are not limited to chloramphenicol acetyl transferase (CAT) gene, which confers resistance to chloramphenicol; CAN1 gene, which encodes an arginine permease and thereby renders cells sensitive to canavanine (see Sikorski et al., *Meth. Enzymol.*, 194:302-318 (1991)); the bacterial kanamycin resistance gene ($kan^R$), which renders eukaryotic cells resistant to the aminoglycoside G418 (see Wach et al., *Yeast*, 10: 1793-1808 (1994)); and CYH2 gene, which confers sensitivity to cycloheximide (see Sikorski et al., *Meth. Enzymol.*, 194:302-318 (1991)). In addition, the CUP1 gene, which encodes metallothionein and thereby confers resistance to copper, is also a suitable selection marker. Each of the above selection markers may be used alone or in combination. One or more selection markers can be included in a particular bait or prey vector. The bait vector and prey vector may have the same or different selection markers. In addition, the selection pressure can be placed on the transformed host cells either before or after mating the haploid yeast cells.

As will be apparent, the selection markers used should complement the host strains in which the bait and/or prey vectors are expressed. In other words, when a gene is used as a selection marker gene, a yeast strain lacking the selection marker gene (or having mutation in the corresponding gene) should be used as host cells. Numerous yeast strains or derivative strains corresponding to various selection markers are known in the art. Many of them have been developed specifically for certain yeast two-hybrid systems. The application and optional modification of such strains with respect to the present invention will be apparent to a skilled artisan apprised of the present disclosure. Methods for genetically manipulating yeast strains using genetic crossing or recombinant mutagenesis are well known in the art. See e.g., Rothstein, *Meth. Enzymol.*, 101:202-211 (1983). By way of example, the following yeast strains are well known in the art, and can be used in the present invention upon necessary modifications and adjustment:

L40 strain which has the genotype MATa his3Δ 200 trp1-901 leu2-3,112 ade2 LYS2::(lexAop)4-HIS3 URA3::(lexAop)8-lacZ;

EGY48 strain which has the genotype MATαtrp1 his3 ura3 6ops-LEU2; and

MaV103 strain which has the genotype MATαura3-52 leu2-3,112 trp1-901 his3Δ200 ade2-101 gal4Δ gal80Δ SPAL10::URA3 GAL1::HIS3::lys2 (see Kumar et al., *J. Biol. Chem.* 272:13548-13554 (1997); Vidal et al., *Proc. Natl. Acad. Sci. USA*, 93:10315-10320 (1996)). Such strains are generally available in the research community, and can also be obtained by simple yeast genetic manipulation. See, e.g., The Yeast Two-Hybrid System, Bartel and Fields, eds., pages 173-182, Oxford University Press, New York, N.Y., 1997.

In addition, the following yeast strains are commercially available:

Y190 strain which is available from Clontech, Palo Alto, Calif. and has the genotype MATa gal4 gal80 his3Δ200 trp1-901 ade2-101 ura3-52 leu2-3, 112 URA3::GAL1-lacZ LYS2::GAL1-HIS3 cyh$^r$; and YRG-2 Strain which is available from Stratagene, La Jolla, Calif. and has the genotype MATαura3-52 his3-200 ade2-101 lys2-801 trp1-901 leu2-3, 112 gal4-542 gal80-538LYS2::GAL1-HIS3 URA3::GAL1/CYC1-lacZ.

In fact, different versions of vectors and host strains specially designed for yeast two-hybrid system analysis are available in kits from commercial vendors such as Clontech, Palo Alto, Calif. and Stratagene, La Jolla, Calif., all of which can be modified for use in the present invention.

In a screening assay for an interaction antagonist, CaM or an active fragment or derivative thereof and TRPM8 or an active fragment or derivative thereof, are used as test proteins expressed in the form of fusion proteins as described above for purposes of a two-hybrid assay. The fusion proteins are expressed in a host cell and allowed to interact with each other in the presence of one or more test compounds.

In a preferred embodiment, a counterselectable marker is used as a reporter such that a detectable signal (e.g., appearance of color or fluorescence, or cell survival) is present only when the test compound is capable of interfering with the interaction between the two test proteins. In this respect, the reporters used in various "reverse two-hybrid systems" known in the art may be employed. Reverse two-hybrid systems are disclosed in, e.g., U.S. Pat. Nos. 5,525,490; 5,733, 726; 5,885,779; Vidal et al., *Proc. Natl. Acad. Sci. USA*, 93:10315-10320 (1996); and Vidal et al., *Proc. Natl. Acad. Sci. USA*, 93:10321-10326 (1996), all of which are incorporated herein by reference.

Examples of suitable counterselectable reporters useful in a yeast system include the URA3 gene (encoding orotidine-5'-decarboxylase, which converts 5-fluroorotic acid (5-FOA) to the toxic metabolite 5-fluorouracil), the CAN1 gene (encoding arginine permease, which transports the toxic arginine analog canavanine into yeast cells), the GAL1 gene (encoding galactokinase, which catalyzes the conversion of 2-deoxygalactose to toxic 2-deoxygalactose-1-phosphate), the LYS2 gene (encoding α-aminoadipate reductase, which renders yeast cells unable to grow on a medium containing α-aminoadipate as the sole nitrogen source), the MET15 gene (encoding O-acetylhomoserine sulfhydrylase, which confers on yeast cells sensitivity to methyl mercury), and the CYH2 gene (encoding L29 ribosomal protein, which confers sensitivity to cycloheximide). In addition, any known cytotoxic agents including cytotoxic proteins such as the diphtheria toxin (DTA) catalytic domain can also be used as counterselectable reporters. See U.S. Pat. No. 5,733,726. DTA causes the ADP-ribosylation of elongation factor-2 and thus inhibits protein synthesis and causes cell death. Other examples of cytotoxic agents include ricin, Shiga toxin, and exotoxin A of *Pseudomonas aeruginosa*.

For example, when the URA3 gene is used as a counterselectable reporter gene, yeast cells containing a mutant URA3 gene can be used as host cells (Ura$^-$Foa$^R$ phenotype) for the in vivo assay. Such cells lack URA3-encoded functional orotidine-5'-phosphate decarboxylase, an enzyme required for the biosynthesis of uracil. As a result, the cells are unable to grow on media lacking uracil. However, because of the absence of a wild-type orotidine-5'-phosphate decarboxylase, the yeast cells cannot convert non-toxic 5-fluoroorotic acid (5-FOA) to a toxic product, 5-fluorouracil. Thus, such yeast cells are resistant to 5-FOA and can grow on a medium containing 5-FOA. Therefore, for example, to screen for a compound capable of disrupting interactions between APOA1 (or a homologue, fragment or derivative thereof), or a mutant form of APOA1 (or a homologue, fragment or derivative thereof), and PRA1 (or a homologue, fragment or derivative thereof), or a mutant form of PRA1 (or a homologue, fragment or derivative thereof), APOA1 (or a homologue, fragment or derivative thereof) is expressed as a fusion protein with a DNA-binding domain of a suitable transcription activator while PRA1 (or a homologue, fragment or derivative thereof) is expressed as a fusion protein with a transcription activation domain of a suitable transcription activator. In the host strain, the reporter URA3 gene may be operably linked to a promoter specifically responsive to the association of the transcription activation domain and the DNA-binding domain. After the fusion proteins are expressed in the Ura$^-$Foa$^R$ yeast cells, an in vivo screening assay can be conducted in the presence of a test compound with the yeast cells being cultured on a medium containing uracil and 5-FOA. If the test compound does not disrupt the interaction between APOA1 and PRA1, active URA3 gene product, i.e., orotidine-5'-decarboxylase, which converts 5-FOA to toxic 5-fluorouracil, is expressed. As a result, the yeast cells cannot grow. On the other hand, when the test compound disrupts the interaction between APOA1 and PRA1, no active orotidine-5'-decarboxylase is produced in the host yeast cells. Consequently, the yeast cells will survive and grow on the 5-FOA-containing medium. Therefore, compounds capable of interfering with or dissociating the interaction between APOA1 and PRA1 can thus be identified based on colony formation.

As will be apparent, the screening assay of the present invention can be applied in a format appropriate for large-scale screening. For example, combinatorial technologies can be employed to construct combinatorial libraries of small organic molecules or small peptides. See generally, e.g., Kenan et al., *Trends Biochem. Sc.*, 19:57-64 (1994); Gallop et al., *J. Med. Chem.*, 37:1233-1251 (1994); Gordon et al., *J. Med. Chem.*, 37:1385-1401 (1994); Ecker al., *Biotechnology*, 13:351-360 (1995). Such combinatorial libraries of compounds can be applied to the screening assay of the present invention to isolate specific modulators of particular protein-protein interactions. In the case of random peptide libraries, the random peptides can be co-expressed with the fusion proteins of the present invention in host cells and assayed in vivo. See e.g., Yang et al., *Nucl. Acids Res.*, 23:1152-1156 (1995). Alternatively, they can be added to the culture medium for uptake by the host cells.

Conveniently, yeast mating is used in an in vivo screening assay. For example, haploid cells of a-mating type expressing one fusion protein as described above are mated with haploid cells of α-mating type expressing the other fusion protein. Upon mating, the diploid cells are spread on a suitable medium to form a lawn. Drops of test compounds can be deposited onto different areas of the lawn. After culturing the lawn for an appropriate period of time, drops containing a compound capable of modulating the interaction between the particular test proteins in the fusion proteins can be identified by stimulation or inhibition of growth in the vicinity of the drops.

The screening assays of the present invention for identifying compounds capable of modulating protein-protein interactions can also be fine-tuned by various techniques to adjust the thresholds or sensitivity of the positive and negative selections. Mutations can be introduced into the reporter proteins to adjust their activities. The uptake of test compounds by the host cells can also be adjusted. For example, yeast high uptake mutants such as the erg6 mutant strains can facilitate yeast uptake of the test compounds. See Gaber et al., *Mol. Cell. Biol.*, 9:3447-3456 (1989). Likewise, the uptake of the selection compounds such as 5-FOA, 2-deoxygalactose, cycloheximide, α-aminoadipate, and the like can also be fine-tuned.

Generally, a control assay is performed in which the above screening assay is conducted in the absence of the test compound. The result of this assay is then compared with that obtained in the presence of the test compound.

In a screening assay for an interaction agonist, the assay can be performed in the same manner as described above for an interaction antagonist, except that a positively selectable marker is used. CaM or an active fragment or derivative thereof and TRPM8 or an active fragment or derivative thereof, are used as test proteins expressed in the form of fusion proteins as described above for purposes of a two-hybrid assay. The fusion proteins are expressed in a host cell and allowed to interact with each other in the presence of one or more test compounds.

A gene encoding a positively selectable marker such as β-galatosidase may be used as a reporter gene such that when a test compound enables, enhances or strengthens the interaction between a first protein, (or a homologue, fragment, or derivative thereof), or a mutant form of the first protein (or a homologue, fragment, or derivative thereof), and a second protein (or a homologue, fragment, or derivative thereof), or a mutant form of the second (or a homologue, fragment, or derivative thereof), β-galatosidase is expressed. As a result, the compound may be identified based on the appearance of a blue color when the host cells are cultured in a medium containing X-Gal.

Generally, a control assay is performed in which the above screening assay is conducted in the absence of the test compound. The result of this assay is then compared with that obtained in the presence of the test compound.

Once a test compound is selected that is capable of modulating the interaction between CaM and TRPM8 in a protein complex, the test compound can be tested in a secondary assay to confirm its specificity and effect. Exemplary secondary assays are cell-based assays or animal based assays.

In one embodiment, the test compound can be further evaluated for its ability to increase or decrease the ion conductivity of a TRPM8 channel. Known to those skilled in the are methods for measuring a TRPM8 channel conductivity, for example, via the stimulation of cellular depolarization or an increase in intracellular calcium ion levels. The level of intracellular calcium can be assessed using a calcium ion-sensitive fluorescent indicator, such as a calcium ion-sensitive fluorescent dye. Suitable calcium ion-sensitive fluorescent dyes include, for example, quin-2 (see, e.g., Tsien et al., J Cell BioL, 94:325, 1982), fura-2 (see, e.g., Grynkiewicz et al., J BioL Chem., 260:3440, 1985), fluo-3 (see, e.g., Kao et al., J BioL—43 Chem., 264:8179, 1989) and rhod-2 (see, e.g., Tsien et al., J Biol. Chem., Abstract 89a, 1987). Suitable calcium ion-sensitive fluorescent dyes are commercially available from, for example, Molecular Probes (Eugene, Oreg.). Cellular fluorescence can also be monitored using a fluorometer or a flow cytometer having a fluorescence lamp and detector.

The TRPM8 cation channels function to transport not only divalent cations, for example, $Ca^{++}$, but also monovalent cations, for example, $Na^+$ or $K^+$. Therefore, assays for determining changes in the transport of monovalent cation can also be performed to measure the conductivity of a TRPM8 channel. $Na^+$- and $K^+$-sensitive dyes are known in the art and commercially available from, for example, Molecular Probes (Eugene, Oreg.).

The conductivity of a TRPM8 channel can also be measured by electrophysiologic techniques such as patch-clamp. Patch-clamp techniques are routinely used for studying electrical activities in cells, cell membranes, and isolated tissues. It involves forming an electrically tight, high-resistance seal between a micropipette and the plasma membrane. The current flowing through individual ion channels within the plasma membrane can then be measured. Different variants on the techniques allow different surfaces of the plasma membrane to be exposed to the bathing medium. The four most common variants include on-cell patch, inside-out patch, outside-out patch, and whole-cell clamp.

A patch-clamp method is commonly used with a voltage clamp that controls the voltage across the membrane and measures current flow. During the voltage clamp process, a microelectrode is inserted into a cell and current injected through the electrode so as to hold the cell membrane potential at some predefined level. A patch-clamp method can also be used with current-clamp methods, in which the current is controlled and the voltage is measured.

In another embodiment, the test compound can be further evaluated by administering it to a live animal. This can be useful to establish toxicity and other pharmacological parameters important for establishing dosing regimens. For example, the compound can be administered to a dog to examine various pharmacological aspects of the compound in the dog. The dog testing can be particularly advantageous for identifying and establishing dosing regimens in humans, because dogs, particularly large breeds, are closer in weight to humans as compared to rats or mice and therefore provide a more suitable animal model for estimating human dosing.

The compound can also be administered to animals to assess the ability of the compound to alter nociceptive processes. Various animal models of pain exist, for example, the spinal nerve ligation (SNL) model of nerve injury, which is a neuropathic pain model in rats developed by Kim and Chung (Pain, 50:355-363, 1992).

Other suitable animal models of pain can be utilized in connection with the teachings herein. Commonly studied rodent models of neuropathic pain include the chronic constriction injury (CCI) or Bennett model; neuroma or axotomy model; and the partial sciatic transection or Seltzer model (Shir et al., *Neurosci. Lett.*, 115:62-67, 1990). Exemplary neuropathic pain models include several traumatic nerve injury preparations (Bennett et al., *Pain* 33: 87-107, 1988; Decosterd et al., *Pain* 87: 149-58, 2000; Kim et al., *Pain* 50: 355-363, 1992; Shir et al., *Neurosci Lett* 115: 62-7, 1990), neuroinflammation models (Chacur et al., *Pain* 94: 231-44, 2001; Milligan et al., *Brain Res* 861: 105-16, 2000) diabetic neuropathy (Calcutt et al., *Br J Pharmacol* 122: 1478-82, 1997), virus-induced neuropathy (Fleetwood-Walker et al., *J Gen Virol* 80: 2433-6, 1999), vincristine neuropathy (Aley et al., *Neuroscience* 73: 259-65, 1996; Nozaki-Taguchi et al., *Pain* 93: 69-76, 2001), and paclitaxel neuropathy (Cavaletti et al., *Exp Neurol* 133: 64-72, 1995), as well as acute nociceptive tests models and inflammatory models (Brennan, T. J. et al. *Pain* 64:493, 1996; D'Amour, F. E. and Smith, D. L. *J Pharmacol* 72: 74-79, 1941; Eddy, N. B. et al. *J Pharmacol Exp Ther* 98:121, 1950; Haffner, F. *Dtsch Med Wochenschr* 55:731, 1929; Hargreaves, K. et al. *Pain* 32: 77-88, 1988; Hunskaar, S. et al. *J Neurosci Meth* 14:69, 1985; Randall, L. O. and Selitto, J. J. *Arch. Int. Pharmacodyn* 111: 409-419, 1957; Siegmund, E. et al. *Proc Soc Exp Bio Med* 95:729, 1957).

In addition, once test compounds are selected that are capable of modulating the interaction of CaM and TRPM8 in a protein complex, a data set including data defining the identity or characteristics of the test compounds can be generated. The data set may include information relating to the properties of a selected test compound, e.g., chemical structure, chirality, molecular weight, melting point, etc. Alternatively, the data set may simply include assigned identification numbers understood by the researchers conducting the screening assay and/or researchers receiving the data set as representing specific test compounds. The data or information can be cast in a transmittable form that can be communicated or transmitted to other researchers, particularly researchers in a different country. Such a transmittable form can vary and can be tangible or intangible. For example, the data set defining one or more selected test compounds can be embodied in texts, tables, diagrams, molecular structures, photographs, charts, images or any other visual forms. The data or information can be recorded on a tangible media such as paper or embodied in computer-readable forms (e.g., electronic, electromagnetic, optical or other signals). The data in a computer-readable form can be stored in a computer usable storage medium (e.g., floppy disks, magnetic tapes, optical disks, and the like) or transmitted directly through a communication infrastructure. In particular, the data embodied in electronic signals can be transmitted in the form of email or posted on a website on the Internet or Intranet. In addition, the information or data on a selected test compound can also be recorded in an audio form and transmitted through any suitable media, e.g., analog or digital cable lines, fiber optic cables, etc., via telephone, facsimile, wireless mobile phone, Internet phone and the like.

Thus, the information and data on a test compound selected in a screening assay described above or by virtual screening as discussed below can be produced anywhere in the world and transmitted to a different location. For example, when a screening assay is conducted offshore, the information and data on a selected test compound can be generated and cast in a transmittable form as described above. The data and information in a transmittable form thus can be imported into the U.S. or transmitted to any other countries, where the data and information may be used in further testing the selected test compound and/or in modifying and optimizing the selected test compound to develop lead compounds for testing in clinical trials.

Compounds can also be selected based on structural models of the target protein or protein complex and/or test compounds. In addition, once an effective compound is identified, structural analogs or mimetics thereof can be produced based on rational drug design with the aim of improving drug efficacy and stability, and reducing side effects. Methods known in the art for rational drug design can be used in the present invention. See, e.g., Hodgson et al., *Bio/Technology*, 9:19-21 (1991); U.S. Pat. Nos. 5,800,998 and 5,891,628, all of which are incorporated herein by reference.

In this respect, structural information on the target protein or protein complex is obtained. Preferably, atomic coordinates defining a three-dimensional structure of the protein complex can be obtained. For example, the interacting TRPM8-CaM complex can be studied using various biophysical techniques including, e. g., X-ray crystallography, NMR, computer modeling, mass spectrometry, and the like. Likewise, structural information can also be obtained from protein complexes formed by interacting proteins and a compound that initiates or stabilizes the interaction of the proteins. Methods for obtaining such atomic coordinates by X-ray crystallography, NMR, and the like are known in the art and the application thereof to the target protein or protein complex of the present invention should be apparent to skilled persons in the art of structural biology. See Smyth and Martin, *Mol. Pathol.*, 53:8-14 (2000); Oakley and Wilce, *Clin. Exp. Pharmacol. Physiol.*, 27(3):145-151 (2000); Ferentz and Wagner, Q. *Rev. Biophys.*, 33:29-65 (2000); Hicks, *Curr. Med. Chem.*, 8(6):627-650 (2001); and Roberts, *Curr. Opin. Biotechnol.*, 10:42-47 (1999).

In addition, understanding of the interaction between the protein complex in the presence or absence of a modulator can also be derived by mutagenic analysis using a yeast two-hybrid system or other methods for detecting protein-protein interactions. In this respect, various mutations can be introduced into the interacting proteins and the effect of the mutations on protein-protein interaction examined by a suitable method such as the yeast two-hybrid system. Various mutations including amino acid substitutions, deletions and insertions can be introduced into a protein sequence using conventional recombinant DNA technologies. Generally, it is particularly desirable to decipher the protein binding sites. Thus, it is important that the mutations introduced only affect protein-protein interactions and cause minimal structural disturbances. Mutations are preferably designed based on knowledge of the three-dimensional structure of the interacting proteins. Preferably, mutations are introduced to alter charged amino acids or hydrophobic amino acids exposed on the surface of the proteins, since ionic interactions and hydrophobic interactions are often involved in protein-protein interactions. Alternatively, the "alanine scanning mutagenesis" technique is used. See Wells, et al., *Methods Enzymol.*, 202:301-306 (1991); Bass et al., *Proc. Natl. Acad. Sci. USA*, 88:4498-4502 (1991); Bennet et al., *J. Biol. Chem.*, 266: 5191-5201 (1991); Diamond et al., *J. Virol.*, 68:863-876 (1994). Using this technique, charged or hydrophobic amino acid residues of the interacting proteins are replaced by alanine, and the effect on the interaction between the proteins is analyzed using e.g., the yeast two-hybrid system. For example, the entire protein sequence can be scanned in a window of five amino acids. When two or more charged or hydrophobic amino acids appear in a window, the charged or hydrophobic amino acids are changed to alanine using standard recombinant DNA techniques. The thus-mutated proteins are used as "test proteins" in the above-described two-hybrid assays to examine the effect of the mutations on protein-protein interaction. Preferably, the mutational analyses are conducted both in the presence and in the absence of an identified modulator compound. In this manner, the domains or residues of the proteins important to protein-protein interaction and/or the interaction between the modulator compound and the interacting proteins can be identified.

Based on the information obtained, structural relationships between the interacting proteins, as well as between the identified modulators and the interacting proteins are elucidated. For example, for the identified modulators (i.e., lead compounds), the three-dimensional structure and chemical moieties critical to their modulating effect on the interacting proteins are revealed. Using this information and various techniques known in the art of molecular modeling (i.e., simulated annealing), medicinal chemists can then design analog compounds that might be more effective modulators of the protein-protein interactions of the present invention. For example, the analog compounds might show more specific or tighter binding to their targets, and thereby might exhibit fewer side effects, or might have more desirable pharmacological characteristics (e.g., greater solubility).

In addition, if the lead compound is a peptide, it can also be analyzed by the alanine scanning technique and/or the two-hybrid assay to determine the domains or residues of the peptide important to its modulating effect on particular protein-protein interactions. The peptide compound can be used as a lead molecule for rational design of small organic molecules or peptide mimetics. See Huber et al., *Curr. Med. Chem.*, 1: 13-34 (1994).

The domains, residues or moieties critical to the modulating effect of the identified compound constitute the active region of the compound known as its "pharmacophore." Once the pharmacophore has been elucidated, a structural model can be established by a modeling process that may incorporate data from NMR analysis, X-ray diffraction data, alanine scanning, spectroscopic techniques and the like. Various techniques including computational analysis (e.g., molecular modeling and simulated annealing), similarity mapping and the like can all be used in this modeling process. See e.g., Perry et al., in *OSAR: Quantitative Structure-Activity Relationships in Drug Design*, pp. 189-193, Alan R. Liss, Inc., 1989; Rotivinen et al., *Acta Pharmaceutical Fennica*, 97:159-166 (1988); Lewis et al., *Proc. R. Soc. Lond.*, 236:125-140 (1989); McKinaly et al., *Annu. Rev. Pharmacol. Toxiciol.*, 29:111-122 (1989). Commercial molecular modeling systems available from Polygen Corporation, Waltham, Mass., include the CHARMm program, which performs energy minimization and molecular dynamics functions, and QUANTA program, which performs construction, graphic modeling and analysis of molecular structure. Such programs allow interactive construction, modification, and visualization of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. In addition, in the case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved efficacy and reduced side effects can be developed. The compounds identified in accordance with the present invention can be incorporated into a pharmaceutical formulation suitable for administration to an individual.

In addition, the structural models or atomic coordinates defining a three-dimensional structure of the target protein or protein complex can also be used in virtual screen to select compounds capable of modulating the target protein or protein complex. Various methods of computer-based virtual screen using atomic coordinates are generally known in the art. For example, U.S. Pat. No. 5,798,247 (which is incorporated herein by reference) discloses a method of identifying a compound (specifically, an interleukin converting enzyme inhibitor) by determining binding interactions between an organic compound and binding sites of a binding cavity within the target protein. The binding sites are defined by atomic coordinates.

The compounds designed or selected based on rational drug design or virtual screen can be tested for their ability to modulate (interfere with or strengthen) the interaction between the interacting partners within the protein complexes of the present invention. In addition, the compounds can further be tested in the TRPM8 channel conductivity assay or the animal models as described supra.

Following the selection of desirable compounds according to the methods disclosed above, the methods of the present invention further provide for the manufacture of the selected compounds. The compounds can be manufactured for further experimental studies, or for therapeutic use. The compounds identified in the screening methods of the present invention can be made into therapeutically or prophylactically effective drugs for preventing or ameliorating diseases, disorders or symptoms caused by or associated with the CaM-TRPM8 protein complex or an interacting member thereof, such as pain, inflammation and skin disorders.

EXAMPLES

Protein Construction and Production

In order to pinpoint CaM binding site on TRPM8, fragments of the rat TRPM8 cDNA were subcloned into a pAGA3 or pGEX-4T1N expression vector for $^{35}$S-methionine labeling protein by in vitro translation or for expressing GST fusion protein in bacteria, respectively. These subclones encode various rat TRPM8 fragments with some overlapping (see Table 1).

TABLE 1

Rat TRPM8 constructs and their binding activity to calmodulin

| Constructs | Residues | Length | Protein size (aax110) | Binding |
|---|---|---|---|---|
| TRPM8-1/pAGA3: | M1-K432 | 432 aa | 48 kDa | + |
| TRPM8-2/pAGA3: | M353-T690 | 337 aa | 37 kDa | − |
| TRPM8-4/pAGA3: | I609-K1104 (end) | 495 aa | 54 kDa | − |
| TRPM8-6/pAGA3: | M63-S352 | 289 aa | 32 kDa | + |
| TRPM8-7/pAGA3: | V145-S352 | 207 aa | 23 kDa | + |
| TRPM8-8/pAGA3: | M219-S352 | 133 aa | 15 kDa | − |
| TRPM8-9/pAGA3: | A172-S352 | 180 aa | 20 kDa | − |
| TRPM8-10/pAGA3: | D198-S352 | 154 aa | 17 kDa | − |
| TRPM8-11/pGEX4T-1N: | V145-W217 | 73 aa | GST fusion | + |

TABLE 1-continued

Rat TRPM8 constructs and their binding activity to calmodulin

| Constructs | Residues | Length | Protein size (aax110) | Binding |
|---|---|---|---|---|
| TRPM8-12/pGEX4T-1N: | V145-D198 | 53 aa | GST fusion | + |

Constructs TRPM8-1/pAGA3 and TRPM8-4/pAGA3 were constructed by conventional restriction digestion and ligation techniques. To obtain TRPM8-1/pAGA3, the TRPM8/pAGA3 carrying the full-length rat TRPM8 cDNA was digested with HindIII to remove the cDNA fragment encoding the carboxyl terminal of the rat TRPM8. The remaining portion of the plasmid carrying the cDNA fragment encoding the amino-terminal of the rat TRPM8 was religated to create TRPM8-1/pAGA3. For the construction of TRPM8-4/pAGA3, a 1.5 kb DNA fragment encoding the carboxyl terminal of the rat TRPM8 was isolated from TRPM8/pAGA3 after the TRPM8/pAGA3 was digested with EcoRV and XbaI. The 1.5 kb fragment was subsequently subcloned into pAGA3 at its EcoRV and XbaI sites to generate TRPM8-4/pAGA3.

The other constructs were constructed by PCR amplification of the rat TRPM8 cDNA fragments (Table 2) followed by subcloning into appropriate expression vectors. The PCR conditions were: 30 cycles of 94° C. for 30 sec (denaturation), 55° C. for 30 sec (annealing), and 72° C. for 2 min (extension) with Advantage™-HF2 DNA polymerase (Clontech). Appropriate restriction digestion sites, such as SalI or NcoI, were included in the PCR primers to facilitate the subsequent subcloning steps (Table 3). The PCR amplified rTRPM8 cDNA fragments were gel purified, digested with appropriate restriction enzymes, and cloned into either pAGA3 (for rTRPM8-2 and rTRPM8-6 to rTRPM8-10) or pGEX-4T-1N (for rTRPM8-11 and rTRPM8-12) expression vectors following standard molecular cloning techniques.

TABLE 2

The rTRPM8 cDNA fragments and the primers used for their PCR amplification.

| | Forward prime | Reverse primer |
|---|---|---|
| rTRPM8-2 | TRPM8-9 | rTRPM8-10 |
| rTRPM8-6 | rTRPM8-1 | rTRPM8-13 |
| rTRPM8-7 | rTRPM8-14 | rTRPM8-13 |
| rTRPM8-8 | rTRPM8-15 | rTRPM8-13 |
| rTRPM8-9 | rTRPM8-17 | rTRPM8-13 |
| rTRPM8-10 | rTRPM8-18 | rTRPM8-13 |
| rTRPM8-11 | rTRPM8-14 | rTRPM8-20 |
| rTRPM8-12 | rTRPM8-14 | rTRPM8-21 |

TABLE 3

PCR primers

| Primer | Sequence | Direction | Restriction Enzyme site |
|---|---|---|---|
| rTRPM8-1 (SEQ ID NO: 14) | Atcgatatgtccttcgagggagccaggctcagca | Forward | |
| TRPM8-9 (SEQ ID NO: 15) | Attggcatagcagcttgg | Forward | |
| rTRPM8-10 (SEQ ID NO: 16) | Tctaga gtcgaccgtgtctcgggaaatctctccata | Reverse | SalI |

TABLE 3-continued

PCR primers

| Primer | Sequence | Direction | Restriction Enzyme site |
|---|---|---|---|
| rTRPM8-13 (SEQ ID NO: 17) | Tctaga<u>gtcgac</u>ggaagaggttaaaacatcctc | Reverse | SalI |
| RTRPM8-14 (SEQ ID NO: 18) | Cccaa<u>ccatgg</u>tcatctcagtg | Forward | NcoI |
| rTRPM8-15 (SEQ ID NO: 19) | Ggg<u>ccatgg</u>tctccaacagggac | Forward | NcoI |
| rTRPM8-17 (SEQ ID NO: 20) | Atcaat<u>ccatgg</u>ctcagtctaaagggcatgg | Forward | NcoI |
| rTRPM8-18 (SEQ ID NO: 21) | Atcaat<u>ccatgg</u>ataacaccatcagcaggaac | Forward | NcoI |
| rTRPM8-20 (SEQ ID NO: 22) | Tctaga<u>gtcgac</u>ttaccaggccgctatgccaat | Reverse | SalI |
| rTRPM8-21 (SEQ ID NO: 23) | tctaga<u>gtcgac</u>ttactacctcaccacttcacctat | Reverse | SalI |

$^{35}$S-methionine labelled TRPM8 fragments were synthesized using TnT® T7 Quick Coupled Transcription/Translation System (Promega) following the vendor recommended protocol. Briefly, 10 µl of 0.1 µg/µl pAGA3 based TRPM8 construct (listed in Table 1) was added to 90 µl of TNT Quick Master Mix with 2 µl of [$^{35}$S]-methionine (1000 Ci/mmmol at 10 mCi/ml). The reaction mixture was incubated at 30° C. for 90 min. Aliquots of the incubation mixtures were used directly either for analysis by SDS/PAGE to confirm synthesis of proteins of the desired size or for the ability to bind to GST or GST-CaM.

The GST-CaM fusion plasmid was based on pGEX-4T-1 (Amersham Pharmacia). The CaM was fused to the C-terminus of GST. After transformation into Escherichia coli BL21, a single colony was picked and grown in brow medium to OD of 1.0 at 600 nm. The synthesis of the fusion protein was induced with 0.2 mM isopropyl β-D-thiogalactoside (IPTG). After growing 2-3 hours in the presence of IPTG at 27° C., the cells were collected by centrifugation, resuspended in NETN lysis buffer (0.5% Nonidet P-40/1 mM EDTA/20 mM Tris-HCl, pH8.0/100 mM NaCl; 1 ml of buffer per 20 ml of culture), and lysed by sonication. The cell lysate was separated from the cell debris by centrifugation at 10,000 g for 10 min at 4° C. GST-CaM in the cell lysate was adsorbed for 30 min at room temperature to agarose-glutathione (GSH) beads (Amersham Pharmacia) (1 vol. of lysates/1 vol of 50% (vol/vol) slurry of Agarose-GSH beads in NETN). The beads were washed with binding buffer (20 mM Tris-HCl, pH7.5/100 mM NaCl/2 mM CaCl$_2$/0.5% Tween20).

Similar to the procedure described supra for the GST-CaM fusion, the TRPM8 fragment TRPM8-11 or TRPM8-12 was fused to the C-terminus of GST, and was expressed and purified from the transformed Escherichia coli BL21.

Protein-Protein Interaction

Agarose-GSH beads (50% (vol./vol.)) bound with about 1 µg of GST or GST-CaM were incubated with 10 µl of $^{35}$S-labelled TRPM8 fragment for 30 min at room temperature in a final volume of 200 µl of binding buffer. At the end of the incubation, the beads were washed three times with 1.0 ml of binding buffer and resuspended in 20 µl of 2× laemmli's sample loading buffer. Protein(s) bound to the beads, including the GST-CaM fusion protein, and possibly the $^{35}$S-labelled TRPM8 fragment that interact with the GST-CaM fusion protein, were separated by SDS/PAGE followed by autoradiography.

Figure 2:
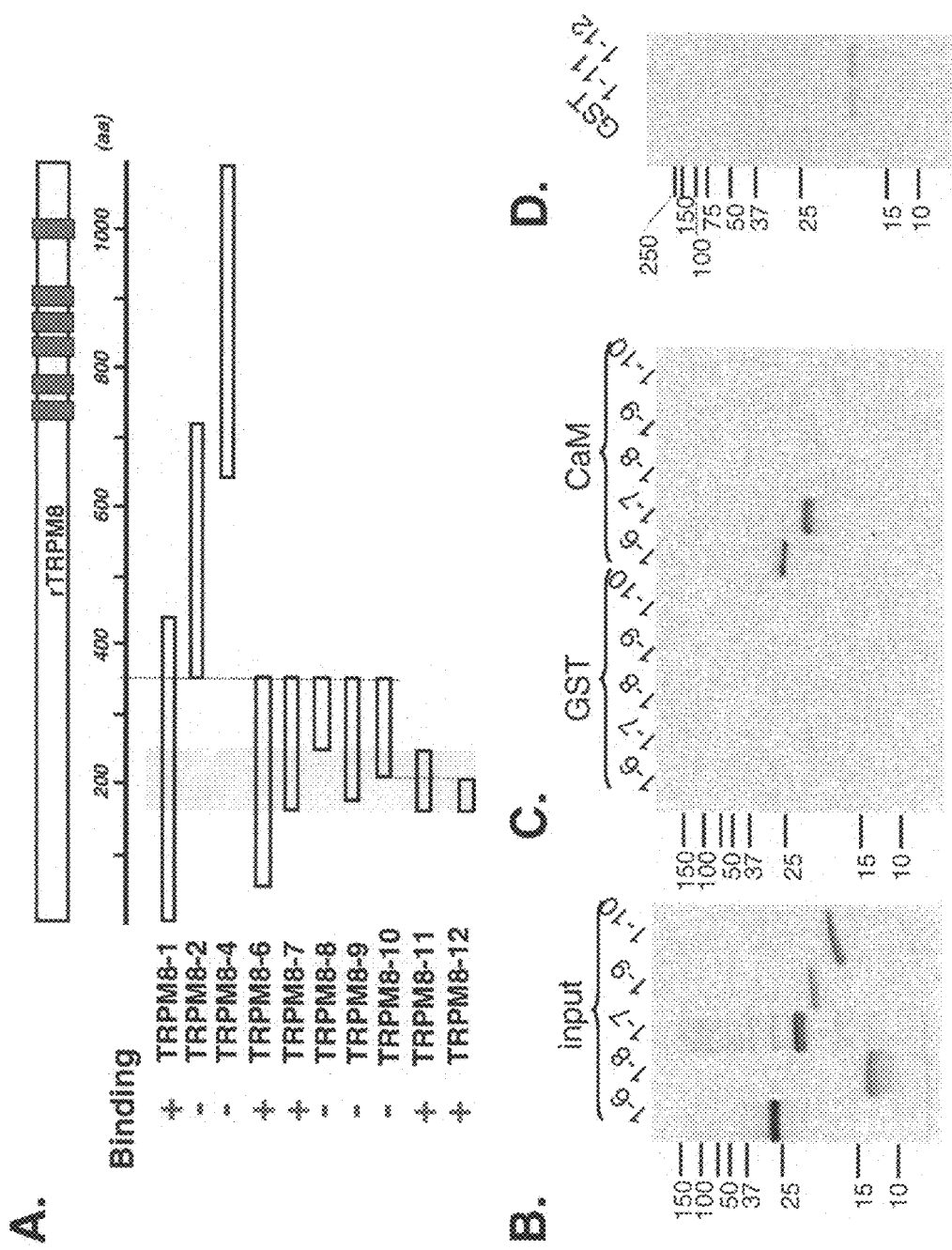
FIG. 2 illustrates the results of a pull-down assay detecting smaller N-terminal TRPM8 fragments that bound to CaM. (A) A linear diagram representation of the TRPM8 fragments and their binding to CaM: (+) binding was detected; (−) no binding was detected. (B) A picture of autoradiograph showing the radio-labeled TRPM8 fragments tested in an assay involving GST-CaM. (C) A picture of autoradiograph showing the radio-labeled TRPM8 fragment. GST: no TRPM8 fragment was found to interact with the GST; CaM: some TRPM8 fragments were found to interact with the GST-CaM fusion protein. (D) A picture of autoradiograph showing the radio-labeled CaM in a reciprocal binding assay involving fusions of GST-TRPM8 fragments: GST-TRPM8-11 and GST-TRPM8-12, was also found to interact with $^{35}$S-methionine labeled CaM.

As shown in FIG. 1, the TRPM8-1 fragment consisting the N-terminal 432 amino acid residues of the rat TRPM8 was found to bind to CaM, not the TRPM8-2 and TRPM8-4 fragments. Smaller TRPM8 fragments with the N-terminal 432 amino acid residues were further tested for their ability to bind to CaM. As shown in FIG. 2, TRPM8-6, TRPM8-7, TRPM8-11, and TRPM8-12, were found to bind CaM. Based on the results, the CaM interaction domain is likely to reside in TRPM8-12, which has the amino acid sequence of SEQ ID NO:9.

What is claimed is:

1. An isolated polypeptide complex comprising 1) a polypeptide comprising TRPM8 or an active fragment of TRPM8 comprising SEQ ID NO: 9 interacting with 2) calmodulin or an active fragment of calmodulin comprising SEQ ID NO: 1.

2. The polypeptide complex of claim 1, wherein the TRPM8 is associated with an isolated membrane.

3. The polypeptide complex of claim 1, wherein said polypeptide comprises the amino acid sequence of SEQ ID NO: 2, SEQ ID NO: 3, or SEQ ID NO: 4.

4. The polypeptide complex of claim 1, wherein said polypeptide comprises the amino acid sequence of SEQ ID NO: 5, SEQ ID NO: 6, SEQ ID NO: 7, or SEQ ID NO: 8.

5. The polypeptide complex of claim 1, wherein said calmodulin comprises the amino acid sequence of SEQ ID NO: 1.

6. A method of producing a polypeptide complex of claim 1, comprising the steps of:
   a. contacting 1) a polypeptide comprising TRPM8 or an active fragment of TRPM8 comprising SEQ ID NO: 9 with 2) calmodulin or an active fragment of calmodulin comprising SEQ ID NO: 1 under a condition that allows the formation of a polypeptide complex comprising said protein of 1) interacting with said protein of 2), wherein at least one of said proteins of 1) and 2) is in isolated form or is recombinantly expressed; and
   b. isolating said polypeptide complex.

7. The method of claim 6, wherein said TRPM8 is associated with an isolated cell membrane.

8. The method of claim 6, wherein the TRPM8 or the active fragment of TRPM8 is present in a cell.

9. The method of claim 8, wherein the cell is a cultured neuron.

10. The method of claim 8, wherein the cell recombinantly expresses the TRPM8 or the active fragment of TRPM8.

11. The method of claim 10, wherein the cell comprises an expression vector having a nucleotide sequence encoding the amino acid sequence of SEQ ID NO: 9.

12. The method of claim 6, wherein the TRPM8 or the active fragment of TRPM8 is in isolated form.

13. The method of claim 6, wherein the calmodulin is in isolated form.

14. The method of claim 6, wherein the calmodulin is present in a cell.

15. The method of claim 14, wherein the cell recombinantly expresses the calmodulin.

16. The method of claim 15, wherein the cell comprises an expression vector having a nucleotide sequence encoding the amino acid sequence of SEQ ID NO: 1.

17. An isolated active fragment of TRPM8 consisting of the amino acid sequence of SEQ ID NO: 9.

18. The polypeptide complex of claim 3, wherein said polypeptide comprises the amino acid sequence of SEQ ID NO: 2.

19. The polypeptide complex of claim 18, wherein said polypeptide consists of the amino acid sequence of SEQ ID NO: 2.

20. The polypeptide complex of claim 3, wherein said polypeptide comprises the amino acid sequence of SEQ ID NO: 3.

21. The polypeptide complex of claim 20, wherein said polypeptide consists of the amino acid sequence of SEQ ID NO: 3.

22. The polypeptide complex of claim 3, wherein said polypeptide comprises the amino acid sequence of SEQ ID NO: 4.

23. The polypeptide complex of claim 22, wherein said polypeptide consists of the amino acid sequence of SEQ ID NO: 4.

24. The polypeptide complex of claim 1, wherein said polypeptide consists of the amino acid sequence of SEQ ID NO: 9.

25. The polypeptide complex of claim 4, wherein said polypeptide comprises the amino acid sequence of SEQ ID NO: 8.

26. The polypeptide complex of claim 25, wherein said polypeptide consists of the amino acid sequence of SEQ ID NO: 8.

27. The polypeptide complex of claim 4, wherein said polypeptide comprises the amino acid sequence of SEQ ID NO: 7.

28. The polypeptide complex of claim 27, wherein said polypeptide consists of the amino acid sequence of SEQ ID NO: 7.

29. The polypeptide complex of claim 4, wherein said polypeptide comprises the amino acid sequence of SEQ ID NO: 6.

30. The polypeptide complex of claim 29, wherein said polypeptide consists of the amino acid sequence of SEQ ID NO: 6.

31. The polypeptide complex of claim 4, wherein said polypeptide comprises the amino acid sequence of SEQ ID NO: 5.

32. The polypeptide complex of claim 31, wherein said polypeptide consists of the amino acid sequence of SEQ ID NO: 5.

* * * * *

SEQUENCE LISTING

<160> NUMBER OF SEQ ID NOS: 23

<210> SEQ ID NO 1
<211> LENGTH: 149
<212> TYPE: PRT
<213> ORGANISM: rat

<400> SEQUENCE: 1

Met Ala Asp Gln Leu Thr Glu Glu Gln Ile Ala Glu Phe Lys Glu Ala

```
                1               5                  10                 15
Phe Ser Leu Phe Asp Lys Asp Gly Asp Gly Thr Ile Thr Lys Glu
                20                 25                 30

Leu Gly Thr Val Met Arg Ser Leu Gly Gln Asn Pro Thr Glu Ala Glu
                35                 40                 45

Leu Gln Asp Met Ile Asn Glu Val Asp Ala Asp Gly Asn Gly Thr Ile
 50                 55                 60

Asp Phe Pro Glu Phe Leu Thr Met Met Ala Arg Lys Met Lys Asp Thr
 65                 70                 75                 80

Asp Ser Glu Glu Glu Ile Arg Glu Ala Phe Arg Val Phe Asp Lys Asp
                85                 90                 95

Gly Asn Gly Tyr Ile Ser Ala Ala Glu Leu Arg His Val Met Thr Asn
                100                105                110

Leu Gly Glu Lys Leu Thr Asp Glu Glu Val Asp Glu Met Ile Arg Glu
                115                120                125

Ala Asp Ile Asp Gly Asp Gly Gln Val Asn Tyr Glu Glu Phe Val Gln
                130                135                140

Met Met Thr Ala Lys
145

<210> SEQ ID NO 2
<211> LENGTH: 1104
<212> TYPE: PRT
<213> ORGANISM: Homo sapiens

<400> SEQUENCE: 2

Met Ser Phe Arg Ala Ala Arg Leu Ser Met Arg Asn Arg Arg Asn Asp
 1               5                  10                 15

Thr Leu Asp Ser Thr Arg Thr Leu Tyr Ser Ser Ala Ser Arg Ser Thr
                20                 25                 30

Asp Leu Ser Tyr Ser Glu Ser Asp Leu Val Asn Phe Ile Gln Ala Asn
                35                 40                 45

Phe Lys Lys Arg Glu Cys Val Phe Phe Ile Lys Asp Ser Lys Ala Thr
 50                 55                 60

Glu Asn Val Cys Lys Cys Gly Tyr Ala Gln Ser Gln His Met Glu Gly
 65                 70                 75                 80

Thr Gln Ile Asn Gln Ser Glu Lys Trp Asn Tyr Lys Lys His Thr Lys
                85                 90                 95

Glu Phe Pro Thr Asp Ala Phe Gly Asp Ile Gln Phe Glu Thr Leu Gly
                100                105                110

Lys Lys Gly Lys Tyr Ile Arg Leu Ser Cys Asp Thr Asp Ala Glu Ile
                115                120                125

Leu Tyr Glu Leu Leu Thr Gln His Trp His Leu Lys Thr Pro Asn Leu
 130                135                140

Val Ile Ser Val Thr Gly Gly Ala Lys Asn Phe Ala Leu Lys Pro Arg
145                 150                155                160

Met Arg Lys Ile Phe Ser Arg Leu Ile Tyr Ile Ala Gln Ser Lys Gly
                165                170                175

Ala Trp Ile Leu Thr Gly Gly Thr His Tyr Gly Leu Met Lys Tyr Ile
                180                185                190

Gly Glu Val Val Arg Asp Asn Thr Ile Ser Arg Ser Ser Glu Glu Asn
                195                200                205

Ile Val Ala Ile Gly Ile Ala Ala Trp Gly Met Val Ser Asn Arg Asp
                210                215                220

Thr Leu Ile Arg Asn Cys Asp Ala Glu Gly Tyr Phe Leu Ala Gln Tyr
```

-continued

```
                225                 230                 235                 240
Leu Met Asp Asp Phe Thr Arg Asp Pro Leu Tyr Ile Leu Asp Asn Asn
                    245                 250                 255

His Thr His Leu Leu Val Asp Asn Gly Cys His Gly His Pro Thr
                260                 265                 270

Val Glu Ala Lys Leu Arg Asn Gln Leu Glu Lys Tyr Ile Ser Glu Arg
                275                 280                 285

Thr Ile Gln Asp Ser Asn Tyr Gly Gly Lys Ile Pro Ile Val Cys Phe
        290                 295                 300

Ala Gln Gly Gly Gly Lys Glu Thr Leu Lys Ala Ile Asn Thr Ser Ile
305                 310                 315                 320

Lys Asn Lys Ile Pro Cys Val Val Glu Gly Ser Gly Gln Ile Ala
                325                 330                 335

Asp Val Ile Ala Ser Leu Val Glu Val Glu Asp Ala Leu Thr Ser Ser
                340                 345                 350

Ala Val Lys Glu Lys Leu Val Arg Phe Leu Pro Arg Thr Val Ser Arg
                355                 360                 365

Leu Pro Glu Glu Glu Thr Glu Ser Trp Ile Lys Trp Leu Lys Glu Ile
        370                 375                 380

Leu Glu Cys Ser His Leu Leu Thr Val Ile Lys Met Glu Glu Ala Gly
385                 390                 395                 400

Asp Glu Ile Val Ser Asn Ala Ile Ser Tyr Ala Leu Tyr Lys Ala Phe
                405                 410                 415

Ser Thr Ser Glu Gln Asp Lys Asp Asn Trp Asn Gly Gln Leu Lys Leu
                420                 425                 430

Leu Leu Glu Trp Asn Gln Leu Asp Leu Ala Asn Asp Glu Ile Phe Thr
        435                 440                 445

Asn Asp Arg Arg Trp Glu Ser Ala Asp Leu Gln Glu Val Met Phe Thr
        450                 455                 460

Ala Leu Ile Lys Asp Arg Pro Lys Phe Val Arg Leu Phe Leu Glu Asn
465                 470                 475                 480

Gly Leu Asn Leu Arg Lys Phe Leu Thr His Asp Val Leu Thr Glu Leu
                485                 490                 495

Phe Ser Asn His Phe Ser Thr Leu Val Tyr Arg Asn Leu Gln Ile Ala
                500                 505                 510

Lys Asn Ser Tyr Asn Asp Ala Leu Leu Thr Phe Val Trp Lys Leu Val
                515                 520                 525

Ala Asn Phe Arg Arg Gly Phe Arg Lys Glu Asp Arg Asn Gly Arg Asp
                530                 535                 540

Glu Met Asp Ile Glu Leu His Asp Val Ser Pro Ile Thr Arg His Pro
545                 550                 555                 560

Leu Gln Ala Leu Phe Ile Trp Ala Ile Leu Gln Asn Lys Lys Glu Leu
                565                 570                 575

Ser Lys Val Ile Trp Glu Gln Thr Arg Gly Cys Thr Leu Ala Ala Leu
                580                 585                 590

Gly Ala Ser Lys Leu Leu Lys Thr Leu Ala Lys Val Lys Asn Asp Ile
                595                 600                 605

Asn Ala Ala Gly Glu Ser Glu Glu Leu Ala Asn Glu Tyr Glu Thr Arg
                610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                645                 650                 655
```

-continued

Leu Glu Leu Ala Val Glu Ala Thr Asp Gln His Phe Ile Ala Gln Pro
        660                 665                 670

Gly Val Gln Asn Phe Leu Ser Lys Gln Trp Tyr Gly Glu Ile Ser Arg
        675                 680                 685

Asp Thr Lys Asn Trp Lys Ile Ile Leu Cys Leu Phe Ile Ile Pro Leu
690                 695                 700

Val Gly Cys Gly Phe Val Ser Phe Arg Lys Lys Pro Val Asp Lys His
705                 710                 715                 720

Lys Lys Leu Leu Trp Tyr Tyr Val Ala Phe Phe Thr Ser Pro Phe Val
                725                 730                 735

Val Phe Ser Trp Asn Val Val Phe Tyr Ile Ala Phe Leu Leu Leu Phe
            740                 745                 750

Ala Tyr Val Leu Leu Met Asp Phe His Ser Val Pro His Pro Pro Glu
        755                 760                 765

Leu Val Leu Tyr Ser Leu Val Phe Val Leu Phe Cys Asp Glu Val Arg
        770                 775                 780

Gln Trp Tyr Val Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
            805                 810                 815

Leu His Ser Ser Asn Lys Ser Ser Leu Tyr Ser Gly Arg Val Ile Phe
        820                 825                 830

Cys Leu Asp Tyr Ile Ile Phe Thr Leu Arg Leu Ile His Ile Phe Thr
        835                 840                 845

Val Ser Arg Asn Leu Gly Pro Lys Ile Ile Met Leu Gln Arg Met Leu
        850                 855                 860

Ile Asp Val Phe Phe Phe Leu Phe Leu Phe Ala Val Trp Met Val Ala
865                 870                 875                 880

Phe Gly Val Ala Arg Gln Gly Ile Leu Arg Gln Asn Glu Gln Arg Trp
            885                 890                 895

Arg Trp Ile Phe Arg Ser Val Ile Tyr Glu Pro Tyr Leu Ala Met Phe
            900                 905                 910

Gly Gln Val Pro Ser Asp Val Asp Gly Thr Thr Tyr Asp Phe Ala His
        915                 920                 925

Cys Thr Phe Thr Gly Asn Glu Ser Lys Pro Leu Cys Val Glu Leu Asp
        930                 935                 940

Glu His Asn Leu Pro Arg Phe Pro Glu Trp Ile Thr Ile Pro Leu Val
945                 950                 955                 960

Cys Ile Tyr Met Leu Ser Thr Asn Ile Leu Leu Val Asn Leu Leu Val
            965                 970                 975

Ala Met Phe Gly Tyr Thr Val Gly Thr Val Gln Glu Asn Asn Asp Gln
            980                 985                 990

Val Trp Lys Phe Gln Arg Tyr Phe Leu Val Gln Glu Tyr Cys Ser Arg
        995                 1000                1005

Leu Asn Ile Pro Phe Pro Phe Ile Val Phe Ala Tyr Phe Tyr Met
        1010                1015                1020

Val Val Lys Lys Cys Phe Lys Cys Cys Cys Lys Glu Lys Asn Met
        1025                1030                1035

Glu Ser Ser Val Cys Cys Phe Lys Asn Glu Asp Asn Glu Thr Leu
        1040                1045                1050

Ala Trp Glu Gly Val Met Lys Glu Asn Tyr Leu Val Lys Ile Asn
        1055                1060                1065

Thr Lys Ala Asn Asp Thr Ser Glu Glu Met Arg His Arg Phe Arg
        1070                1075                1080

-continued

```
Gln Leu  Asp Thr Lys Leu Asn  Asp Leu Lys Gly Leu  Leu Lys Glu
    1085             1090             1095

Ile Ala  Asn Lys Ile Lys
    1100

<210> SEQ ID NO 3
<211> LENGTH: 1104
<212> TYPE: PRT
<213> ORGANISM: rat

<400> SEQUENCE: 3

Met Ser Phe Glu Gly Ala Arg Leu Ser Met Arg Ser Arg Arg Asn Gly
1               5                   10                  15

Thr Leu Gly Ser Thr Arg Thr Leu Tyr Ser Ser Val Ser Arg Ser Thr
            20                  25                  30

Asp Val Ser Tyr Ser Glu Ser Asp Leu Val Asn Phe Ile Gln Ala Asn
        35                  40                  45

Phe Lys Lys Arg Glu Cys Val Phe Phe Thr Arg Asp Ser Lys Ala Met
    50                  55                  60

Glu Ser Ile Cys Lys Cys Gly Tyr Ala Gln Ser Gln His Ile Glu Gly
65                  70                  75                  80

Thr Gln Ile Asn Gln Asn Glu Lys Trp Asn Tyr Lys Lys His Thr Lys
                85                  90                  95

Glu Phe Pro Thr Asp Ala Phe Gly Asp Ile Gln Phe Glu Thr Leu Gly
            100                 105                 110

Lys Lys Gly Lys Tyr Leu Arg Leu Ser Cys Asp Thr Asp Ser Glu Thr
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Asn Ser Glu Glu Asn
        195                 200                 205

Ile Val Ala Ile Gly Ile Ala Ala Trp Gly Met Val Ser Asn Arg Asp
    210                 215                 220

Thr Leu Ile Arg Asn Cys Asp Asp Glu Gly His Phe Ser Ala Gln Tyr
225                 230                 235                 240

Ile Met Asp Asp Phe Met Arg Asp Pro Leu Tyr Ile Leu Asp Asn Asn
                245                 250                 255

His Thr His Leu Leu Val Asp Asn Gly Cys His Gly His Pro Thr
            260                 265                 270

Val Glu Ala Lys Leu Arg Asn Gln Leu Glu Lys Tyr Ile Ser Glu Arg
        275                 280                 285

Thr Ser Gln Asp Ser Asn Tyr Gly Gly Lys Ile Pro Ile Val Cys Phe
    290                 295                 300

Ala Gln Gly Gly Gly Arg Glu Thr Leu Lys Ala Ile Asn Thr Ser Val
305                 310                 315                 320

Lys Ser Lys Ile Pro Cys Val Val Glu Gly Ser Gly Gln Ile Ala
                325                 330                 335

Asp Val Ile Ala Ser Leu Val Glu Val Glu Asp Val Leu Thr Ser Ser
            340                 345                 350
```

```
Met Val Lys Glu Lys Leu Val Arg Phe Leu Pro Arg Thr Val Ser Arg
            355                 360                 365

Leu Pro Glu Glu Glu Ile Glu Ser Trp Ile Lys Trp Leu Lys Glu Ile
    370                 375                 380

Leu Glu Ser Pro His Leu Leu Thr Val Ile Lys Met Glu Glu Ala Gly
385                 390                 395                 400

Asp Glu Val Val Ser Ser Ala Ile Ser Tyr Ala Leu Tyr Lys Ala Phe
                405                 410                 415

Ser Thr Asn Glu Gln Asp Lys Asp Asn Trp Asn Gly Gln Leu Lys Leu
            420                 425                 430

Leu Leu Glu Trp Asn Gln Leu Asp Leu Ala Ser Asp Glu Ile Phe Thr
        435                 440                 445

Asn Asp Arg Arg Trp Glu Ser Ala Asp Leu Gln Glu Val Met Phe Thr
    450                 455                 460

Ala Leu Ile Lys Asp Arg Pro Lys Phe Val Arg Leu Phe Leu Glu Asn
465                 470                 475                 480

Gly Leu Asn Leu Gln Lys Phe Leu Thr Asn Glu Val Leu Thr Glu Leu
                485                 490                 495

Phe Ser Thr His Phe Ser Thr Leu Val Tyr Arg Asn Leu Gln Ile Ala
            500                 505                 510

Lys Asn Ser Tyr Asn Asp Ala Leu Leu Thr Phe Val Trp Lys Leu Val
        515                 520                 525

Ala Asn Phe Arg Arg Ser Phe Trp Lys Glu Asp Arg Ser Ser Arg Glu
    530                 535                 540

Asp Leu Asp Val Glu Leu His Asp Ala Ser Leu Thr Thr Arg His Pro
545                 550                 555                 560

Leu Gln Ala Leu Phe Ile Trp Ala Ile Leu Gln Asn Lys Lys Glu Leu
                565                 570                 575

Ser Lys Val Ile Trp Glu Gln Thr Lys Gly Cys Thr Leu Ala Ala Leu
            580                 585                 590

Gly Ala Ser Lys Leu Leu Lys Thr Leu Ala Lys Val Lys Asn Asp Ile
        595                 600                 605

Asn Ala Ala Gly Glu Ser Glu Glu Leu Ala Asn Glu Tyr Glu Thr Arg
    610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                645                 650                 655

Leu Glu Leu Ala Val Glu Ala Thr Asp Gln His Phe Ile Ala Gln Pro
            660                 665                 670

Gly Val Gln Asn Phe Leu Ser Lys Gln Trp Tyr Gly Glu Ile Ser Arg
        675                 680                 685

Asp Thr Lys Asn Trp Lys Ile Ile Leu Cys Leu Phe Ile Ile Pro Leu
    690                 695                 700

Val Gly Cys Gly Leu Val Ser Phe Arg Lys Lys Pro Ile Asp Lys His
705                 710                 715                 720

Lys Lys Leu Leu Trp Tyr Tyr Val Ala Phe Phe Thr Ser Pro Phe Val
                725                 730                 735

Val Phe Ser Trp Asn Val Val Phe Tyr Ile Ala Phe Leu Leu Leu Phe
            740                 745                 750

Ala Tyr Val Leu Leu Met Asp Phe His Ser Val Pro His Thr Pro Glu
        755                 760                 765

Leu Ile Leu Tyr Ala Leu Val Phe Val Leu Phe Cys Asp Glu Val Arg
```

```
                770              775              780
Gln Trp Tyr Met Asn Gly Val Asn Tyr Phe Thr Asp Leu Trp Asn Val
785              790              795              800

Met Asp Thr Leu Gly Leu Phe Tyr Phe Ile Ala Gly Ile Val Phe Arg
                805              810              815

Leu His Ser Ser Asn Lys Ser Ser Leu Tyr Ser Gly Arg Val Ile Phe
                820              825              830

Cys Leu Asp Tyr Ile Ile Phe Thr Leu Arg Leu His Ile Phe Thr
                835              840              845

Val Ser Arg Asn Leu Gly Pro Lys Ile Ile Met Leu Gln Arg Met Leu
850              855              860

Ile Asp Val Phe Phe Phe Leu Phe Leu Phe Ala Val Trp Met Val Ala
865              870              875              880

Phe Gly Val Ala Arg Gln Gly Ile Leu Arg Gln Asn Glu Gln Arg Trp
                885              890              895

Arg Trp Ile Phe Arg Ser Val Ile Tyr Glu Pro Tyr Leu Ala Met Phe
                900              905              910

Gly Gln Val Pro Ser Asp Val Asp Ser Thr Thr Tyr Asp Phe Ser His
                915              920              925

Cys Thr Phe Ser Gly Asn Glu Ser Lys Pro Leu Cys Val Glu Leu Asp
930              935              940

Glu Tyr Asn Leu Pro Arg Phe Pro Glu Trp Ile Thr Ile Pro Leu Val
945              950              955              960

Cys Ile Tyr Met Leu Ser Thr Asn Ile Leu Leu Val Asn Leu Leu Val
                965              970              975

Ala Met Phe Gly Tyr Thr Val Gly Ile Val Gln Glu Asn Asn Asp Gln
                980              985              990

Val Trp Lys Phe Gln Arg Tyr Phe Leu Val Gln Glu Tyr Cys Asn Arg
                995             1000             1005

Leu Asn Ile Pro Phe Pro Val Val Phe Ala Tyr Phe Tyr Met
   1010             1015             1020

Val Val Lys Lys Cys Phe Lys Cys Cys Cys Lys Glu Lys Asn Thr
   1025             1030             1035

Glu Ser Ser Ala Cys Cys Phe Arg Asn Glu Asp Asn Glu Thr Leu
   1040             1045             1050

Ala Trp Glu Gly Val Met Lys Glu Asn Tyr Leu Val Lys Ile Asn
   1055             1060             1065

Thr Lys Ala Asn Asp Asn Ala Glu Glu Met Arg His Arg Phe Arg
   1070             1075             1080

Gln Leu Asp Thr Lys Leu Asn Asp Leu Lys Gly Leu Leu Lys Glu
   1085             1090             1095

Ile Ala Asn Lys Ile Lys
   1100

<210> SEQ ID NO 4
<211> LENGTH: 1104
<212> TYPE: PRT
<213> ORGANISM: mouse

<400> SEQUENCE: 4

Met Ser Phe Glu Gly Ala Arg Leu Ser Met Arg Ser Arg Arg Asn Gly
1               5              10              15

Thr Met Gly Ser Thr Arg Thr Leu Tyr Ser Ser Val Ser Arg Ser Thr
                20              25              30

Asp Val Ser Tyr Ser Asp Ser Asp Leu Val Asn Phe Ile Gln Ala Asn
```

```
                35                  40                  45
Phe Lys Lys Arg Glu Cys Val Phe Phe Thr Arg Asp Ser Lys Ala Met
 50                  55                  60
Glu Asn Ile Cys Lys Cys Gly Tyr Ala Gln Ser Gln His Ile Glu Gly
 65                  70                  75                  80
Thr Gln Ile Asn Gln Asn Glu Lys Trp Asn Tyr Lys Lys His Thr Lys
                 85                  90                  95
Glu Phe Pro Thr Asp Ala Phe Gly Asp Ile Gln Phe Glu Thr Leu Gly
                100                 105                 110
Lys Lys Gly Lys Tyr Leu Arg Leu Ser Cys Asp Thr Asp Ser Glu Thr
            115                 120                 125
Leu Tyr Glu Leu Leu Thr Gln His Trp His Leu Lys Thr Pro Asn Leu
            130                 135                 140
Val Ile Ser Val Thr Gly Gly Ala Lys Asn Phe Ala Leu Lys Pro Arg
145                 150                 155                 160
Met Arg Lys Ile Phe Ser Arg Leu Ile Tyr Ile Ala Gln Ser Lys Gly
                165                 170                 175
Ala Trp Ile Leu Thr Gly Gly Thr His Tyr Gly Leu Met Lys Tyr Ile
            180                 185                 190
Gly Glu Val Val Arg Asp Asn Thr Ile Ser Arg Asn Ser Glu Glu Asn
            195                 200                 205
Ile Val Ala Ile Gly Ile Ala Ala Trp Gly Met Val Ser Asn Arg Asp
210                 215                 220
Thr Leu Ile Arg Ser Cys Asp Asp Glu Gly His Phe Ser Ala Gln Tyr
225                 230                 235                 240
Ile Met Asp Asp Phe Thr Arg Asp Pro Leu Tyr Ile Leu Asp Asn Asn
                245                 250                 255
His Thr His Leu Leu Leu Val Asp Asn Gly Cys His Gly His Pro Thr
            260                 265                 270
Val Glu Ala Lys Leu Arg Asn Gln Leu Glu Lys Tyr Ile Ser Glu Arg
            275                 280                 285
Thr Ser Gln Asp Ser Asn Tyr Gly Gly Lys Ile Pro Ile Val Cys Phe
290                 295                 300
Ala Gln Gly Gly Gly Arg Glu Thr Leu Lys Ala Ile Asn Thr Ser Val
305                 310                 315                 320
Lys Ser Lys Ile Pro Cys Val Val Val Glu Gly Ser Gly Gln Ile Ala
                325                 330                 335
Asp Val Ile Ala Ser Leu Val Glu Val Glu Asp Val Leu Thr Ser Ser
            340                 345                 350
Met Val Lys Glu Lys Leu Val Arg Phe Leu Pro Arg Thr Val Ser Arg
            355                 360                 365
Leu Pro Glu Glu Glu Ile Glu Ser Trp Ile Lys Trp Leu Lys Glu Ile
370                 375                 380
Leu Glu Ser Ser His Leu Leu Thr Val Ile Lys Met Glu Glu Ala Gly
385                 390                 395                 400
Asp Glu Ile Val Ser Asn Ala Ile Ser Tyr Ala Leu Tyr Lys Ala Phe
                405                 410                 415
Ser Thr Asn Glu Gln Asp Lys Asp Asn Trp Asn Gly Gln Leu Lys Leu
            420                 425                 430
Leu Leu Glu Trp Asn Gln Leu Asp Leu Ala Ser Asp Glu Ile Phe Thr
            435                 440                 445
Asn Asp Arg Arg Trp Glu Ser Ala Asp Leu Gln Glu Val Met Phe Thr
450                 455                 460
```

```
Ala Leu Ile Lys Asp Arg Pro Lys Phe Val Arg Leu Phe Leu Glu Asn
465                 470                 475                 480

Gly Leu Asn Leu Gln Lys Phe Leu Thr Asn Glu Val Leu Thr Glu Leu
                485                 490                 495

Phe Ser Thr His Phe Ser Thr Leu Val Tyr Arg Asn Leu Gln Ile Ala
            500                 505                 510

Lys Asn Ser Tyr Asn Asp Ala Leu Leu Thr Phe Val Trp Lys Leu Val
            515                 520                 525

Ala Asn Phe Arg Arg Ser Phe Trp Lys Glu Asp Arg Ser Ser Arg Glu
        530                 535                 540

Asp Leu Asp Val Glu Leu His Asp Ala Ser Leu Thr Thr Arg His Pro
545                 550                 555                 560

Leu Gln Ala Leu Phe Ile Trp Ala Ile Leu Gln Asn Lys Lys Glu Leu
                565                 570                 575

Ser Lys Val Ile Trp Glu Gln Thr Lys Gly Cys Thr Leu Ala Ala Leu
            580                 585                 590

Gly Ala Ser Lys Leu Leu Lys Thr Leu Ala Lys Val Lys Asn Asp Ile
        595                 600                 605

Asn Ala Ala Gly Glu Ser Glu Glu Leu Ala Asn Glu Tyr Glu Thr Arg
610                 615                 620

Ala Val Glu Leu Phe Thr Glu Cys Tyr Ser Asn Asp Glu Asp Leu Ala
625                 630                 635                 640

Glu Gln Leu Leu Val Tyr Ser Cys Glu Ala Trp Gly Gly Ser Asn Cys
                645                 650                 655

Leu Glu Leu Ala Val Glu Ala Thr Asp Gln His Phe Ile Ala Gln Pro
            660                 665                 670

Gly Val Gln Asn Phe Leu Ser Lys Gln Trp Tyr Gly Glu Ile Ser Arg
        675                 680                 685

Asp Thr Lys Asn Trp Lys Ile Ile Leu Cys Leu Phe Ile Ile Pro Leu
        690                 695                 700

Val Gly Cys Gly Leu Val Ser Phe Arg Lys Lys Pro Ile Asp Lys His
705                 710                 715                 720

Lys Lys Leu Leu Trp Tyr Tyr Val Ala Phe Phe Thr Ser Pro Phe Val
                725                 730                 735

Val Phe Ser Trp Asn Val Val Phe Tyr Ile Ala Phe Leu Leu Leu Phe
            740                 745                 750

Ala Tyr Val Leu Leu Met Asp Phe His Ser Val Pro His Thr Pro Glu
        755                 760                 765

Leu Ile Leu Tyr Ala Leu Val Phe Val Leu Phe Cys Asp Glu Val Arg
        770                 775                 780

Gln Trp Tyr Met Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
                805                 810                 815

Leu His Ser Ser Asn Lys Ser Ser Leu Tyr Ser Gly Arg Val Ile Phe
            820                 825                 830

Cys Leu Asp Tyr Ile Ile Phe Thr Leu Arg Leu Ile His Ile Phe Thr
        835                 840                 845

Val Ser Arg Asn Leu Gly Pro Lys Ile Ile Met Leu Gln Arg Met Leu
850                 855                 860

Ile Asp Val Phe Phe Phe Leu Phe Leu Phe Ala Val Trp Met Val Ala
865                 870                 875                 880

Phe Gly Val Ala Arg Gln Gly Ile Leu Arg Gln Asn Glu Gln Arg Trp
                885                 890                 895
```

-continued

```
Arg Trp Ile Phe Arg Ser Val Ile Tyr Glu Pro Tyr Leu Ala Met Phe
            900                 905                 910

Gly Gln Val Pro Ser Asp Val Asp Ser Thr Thr Tyr Asp Phe Ser His
            915                 920                 925

Cys Thr Phe Ser Gly Asn Glu Ser Lys Pro Leu Cys Val Glu Leu Asp
            930                 935                 940

Glu His Asn Leu Pro Arg Phe Pro Gly Trp Ile Thr Ile Pro Leu Val
945                 950                 955                 960

Cys Ile Tyr Met Leu Ser Thr Asn Ile Leu Leu Val Asn Leu Leu Val
            965                 970                 975

Ala Met Phe Gly Tyr Thr Val Gly Ile Val Gln Glu Asn Asn Asp Gln
            980                 985                 990

Val Trp Lys Phe Gln Arg Tyr Phe  Leu Val Gln Glu Tyr  Cys Asn Arg
            995                 1000                1005

Leu Asn  Ile Pro Phe Pro  Phe  Val Val Phe Ala Tyr  Phe Tyr Met
    1010                1015                1020

Val Val  Lys Lys Cys Phe Lys  Cys Cys Cys Lys Glu  Lys Asn Met
    1025                1030                1035

Glu Ser  Asn Ala Cys Cys Phe  Arg Asn Glu Asp Asn  Glu Thr Leu
    1040                1045                1050

Ala Trp  Glu Gly Val Met Lys  Glu Asn Tyr Leu Val  Lys Ile Asn
    1055                1060                1065

Thr Lys  Ala Asn Asp Asn Ser  Glu Glu Met Arg His  Arg Phe Arg
    1070                1075                1080

Gln Leu  Asp Ser Lys Leu Asn  Asp Leu Lys Ser Leu  Leu Lys Glu
    1085                1090                1095

Ile Ala  Asn Asn Ile Lys
    1100

<210> SEQ ID NO 5
<211> LENGTH: 431
<212> TYPE: PRT
<213> ORGANISM: rat

<400> SEQUENCE: 5

Met Ser Phe Glu Gly Ala Arg Leu Ser Met Arg Ser Arg Arg Asn Gly
1               5                   10                  15

Thr Leu Gly Ser Thr Arg Thr Leu Tyr Ser Ser Val Ser Arg Ser Thr
            20                  25                  30

Asp Val Ser Tyr Ser Glu Ser Asp Leu Val Asn Phe Ile Gln Ala Asn
            35                  40                  45

Phe Lys Lys Arg Glu Cys Val Phe Phe Thr Arg Asp Ser Lys Ala Met
        50                  55                  60

Glu Ser Ile Cys Lys Cys Gly Tyr Ala Gln Ser Gln His Ile Glu Gly
65              70                  75                  80

Thr Gln Ile Asn Gln Asn Glu Lys Trp Asn Tyr Lys Lys His Thr Lys
            85                  90                  95

Glu Phe Pro Thr Asp Ala Phe Gly Asp Ile Gln Phe Glu Thr Leu Gly
            100                 105                 110

Lys Lys Gly Lys Tyr Leu Arg Leu Ser Cys Asp Thr Asp Ser Glu Thr
            115                 120                 125

Leu Tyr Glu Leu Leu Thr Gln His Trp His Leu Lys Thr Pro Asn Leu
            130                 135                 140

Val Ile Ser Val Thr Gly Gly Ala Lys Asn Phe Ala Leu Lys Pro Arg
145                 150                 155                 160
```

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Asn Ser Glu Glu Asn
                195                 200                 205

Ile Val Ala Ile Gly Ile Ala Ala Trp Gly Met Val Ser Asn Arg Asp
210                 215                 220

Thr Leu Ile Arg Asn Cys Asp Asp Glu Gly His Phe Ser Ala Gln Tyr
225                 230                 235                 240

Ile Met Asp Asp Phe Met Arg Asp Pro Leu Tyr Ile Leu Asp Asn Asn
                245                 250                 255

His Thr His Leu Leu Val Asp Asn Gly Cys His Gly His Pro Thr
                260                 265                 270

Val Glu Ala Lys Leu Arg Asn Gln Leu Glu Lys Tyr Ile Ser Glu Arg
                275                 280                 285

Thr Ser Gln Asp Ser Asn Tyr Gly Gly Lys Ile Pro Ile Val Cys Phe
290                 295                 300

Ala Gln Gly Gly Gly Arg Glu Thr Leu Lys Ala Ile Asn Thr Ser Val
305                 310                 315                 320

Lys Ser Lys Ile Pro Cys Val Val Glu Gly Ser Gly Gln Ile Ala
                325                 330                 335

Asp Val Ile Ala Ser Leu Val Glu Val Glu Asp Val Leu Thr Ser Ser
                340                 345                 350

Met Val Lys Glu Lys Leu Val Arg Phe Leu Pro Arg Thr Val Ser Arg
                355                 360                 365

Leu Pro Glu Glu Glu Ile Glu Ser Trp Ile Lys Trp Leu Lys Glu Ile
                370                 375                 380

Leu Glu Ser Pro His Leu Leu Thr Val Ile Lys Met Glu Glu Ala Gly
385                 390                 395                 400

Asp Glu Val Val Ser Ser Ala Ile Ser Tyr Ala Leu Tyr Lys Ala Phe
                405                 410                 415

Ser Thr Asn Glu Gln Asp Lys Asp Asn Trp Asn Gly Gln Leu Lys
                420                 425                 430

<210> SEQ ID NO 6
<211> LENGTH: 289
<212> TYPE: PRT
<213> ORGANISM: rat

<400> SEQUENCE: 6

Met Glu Ser Ile Cys Lys Cys Gly Tyr Ala Gln Ser Gln His Ile Glu
1               5                   10                  15

Gly Thr Gln Ile Asn Gln Asn Glu Lys Trp Asn Tyr Lys Lys His Thr
                20                  25                  30

Lys Glu Phe Pro Thr Asp Ala Phe Gly Asp Ile Gln Phe Glu Thr Leu
            35                  40                  45

Gly Lys Lys Gly Lys Tyr Leu Arg Leu Ser Cys Asp Thr Asp Ser Glu
        50                  55                  60

Thr Leu Tyr Glu Leu Leu Thr Gln His Trp His Leu Lys Thr Pro Asn
65                  70                  75                  80

Leu Val Ile Ser Val Thr Gly Gly Ala Lys Asn Phe Ala Leu Lys Pro
                85                  90                  95

Arg Met Arg Lys Ile Phe Ser Arg Leu Ile Tyr Ile Ala Gln Ser Lys
                100                 105                 110

Gly Ala Trp Ile Leu Thr Gly Gly Thr His Tyr Gly Leu Met Lys Tyr
            115                 120                 125

Ile Gly Glu Val Val Arg Asp Asn Thr Ile Ser Arg Asn Ser Glu Glu
            130                 135                 140

Asn Ile Val Ala Ile Gly Ile Ala Ala Trp Gly Met Val Ser Asn Arg
145                 150                 155                 160

Asp Thr Leu Ile Arg Asn Cys Asp Asp Glu Gly His Phe Ser Ala Gln
                165                 170                 175

Tyr Ile Met Asp Asp Phe Met Arg Asp Pro Leu Tyr Ile Leu Asp Asn
            180                 185                 190

Asn His Thr His Leu Leu Val Asp Asn Gly Cys His Gly His Pro
            195                 200                 205

Thr Val Glu Ala Lys Leu Arg Asn Gln Leu Glu Lys Tyr Ile Ser Glu
            210                 215                 220

Arg Thr Ser Gln Asp Ser Asn Tyr Gly Gly Lys Ile Pro Ile Val Cys
225                 230                 235                 240

Phe Ala Gln Gly Gly Gly Arg Glu Thr Leu Lys Ala Ile Asn Thr Ser
                245                 250                 255

Val Lys Ser Lys Ile Pro Cys Val Val Glu Gly Ser Gly Gln Ile
            260                 265                 270

Ala Asp Val Ile Ala Ser Leu Val Glu Val Asp Val Leu Thr Ser
            275                 280                 285

Ser

<210> SEQ ID NO 7
<211> LENGTH: 208
<212> TYPE: PRT
<213> ORGANISM: rat

<400> SEQUENCE: 7

Val Ile Ser Val Thr Gly Gly Ala Lys Asn Phe Ala Leu Lys Pro Arg
1               5                   10                  15

Met Arg Lys Ile Phe Ser Arg Leu Ile Tyr Ile Ala Gln Ser Lys Gly
            20                  25                  30

Ala Trp Ile Leu Thr Gly Gly Thr His Tyr Gly Leu Met Lys Tyr Ile
            35                  40                  45

Gly Glu Val Val Arg Asp Asn Thr Ile Ser Arg Asn Ser Glu Glu Asn
            50                  55                  60

Ile Val Ala Ile Gly Ile Ala Ala Trp Gly Met Val Ser Asn Arg Asp
65                  70                  75                  80

Thr Leu Ile Arg Asn Cys Asp Asp Glu Gly His Phe Ser Ala Gln Tyr
                85                  90                  95

Ile Met Asp Asp Phe Met Arg Asp Pro Leu Tyr Ile Leu Asp Asn Asn
            100                 105                 110

His Thr His Leu Leu Val Asp Asn Gly Cys His Gly His Pro Thr
            115                 120                 125

Val Glu Ala Lys Leu Arg Asn Gln Leu Glu Lys Tyr Ile Ser Glu Arg
            130                 135                 140

Thr Ser Gln Asp Ser Asn Tyr Gly Gly Lys Ile Pro Ile Val Cys Phe
145                 150                 155                 160

Ala Gln Gly Gly Gly Arg Glu Thr Leu Lys Ala Ile Asn Thr Ser Val
                165                 170                 175

Lys Ser Lys Ile Pro Cys Val Val Glu Gly Ser Gly Gln Ile Ala
            180                 185                 190

Asp Val Ile Ala Ser Leu Val Glu Val Glu Asp Val Leu Thr Ser Ser
            195                 200                 205

<210> SEQ ID NO 8
<211> LENGTH: 73
<212> TYPE: PRT
<213> ORGANISM: rat

<400> SEQUENCE: 8

Val Ile Ser Val Thr Gly Gly Ala Lys Asn Phe Ala Leu Lys Pro Arg
1               5                   10                  15

Met Arg Lys Ile Phe Ser Arg Leu Ile Tyr Ile Ala Gln Ser Lys Gly
            20                  25                  30

Ala Trp Ile Leu Thr Gly Gly Thr His Tyr Gly Leu Met Lys Tyr Ile
        35                  40                  45

Gly Glu Val Val Arg Asp Asn Thr Ile Ser Arg Asn Ser Glu Glu Asn
    50                  55                  60

Ile Val Ala Ile Gly Ile Ala Ala Trp
65                  70

<210> SEQ ID NO 9
<211> LENGTH: 54
<212> TYPE: PRT
<213> ORGANISM: rat

<400> SEQUENCE: 9

Val Ile Ser Val Thr Gly Gly Ala Lys Asn Phe Ala Leu Lys Pro Arg
1               5                   10                  15

Met Arg Lys Ile Phe Ser Arg Leu Ile Tyr Ile Ala Gln Ser Lys Gly
            20                  25                  30

Ala Trp Ile Leu Thr Gly Gly Thr His Tyr Gly Leu Met Lys Tyr Ile
        35                  40                  45

Gly Glu Val Val Arg Asp
    50

<210> SEQ ID NO 10
<211> LENGTH: 1112
<212> TYPE: DNA
<213> ORGANISM: rat

<400> SEQUENCE: 10
ttagtccgag tggagcgagc gagtcgagtg gttgtctgtt ctggtctcgg aaaccggtag      60
cccttgcagc atggctgacc aactgactga agagcagatc gcagaattca agaagctttt    120
ctccctattt gacaaggacg gggatgggac aataacaacc aaggagctgg gacggtgat     180 gcggtctctg gggcagaacc ccacagaagc agagctgcag gacatgatca atgaagtaga    240
tgccgacggt aatggcacaa tcgacttccc tgaatttctg acaatgatgg caagaaaaat    300
gaaagacaca gacagtgaag aagaaattag agaagcgttc cgtgtgtttg ataaggacgg    360
caatggctac atcagtgcag cagagcttcg ccacgtgatg acaaaccttg agagaagtt     420 aacagatgaa gaggttgatg aaatgatcag ggaagcagac atcgatgggg atggtcaggt    480
aaactacgaa gagtttgtac aaatgatgac agcgaagtag agaccctgta cagaaggtgt    540
taaatttctt gtacagaact gttaatttgc cttttctctg tttgtaactt atctgtaaaa    600
ggttccccaa ttgtcagaac atgcatgtat agtaattagg attcattctt ccatgttttt    660
tccctatctt ctgtcattgt ccttcaacct tattttagaa aagtgatcaa gtaccatgtt    720
gcatgtggct tctctggata tatctaagcc ttctgcacat ctacacttag atggagttgg    780

| | |
|---|---|
| tcaaagggaa catctgggtt atgacctttt ttacagtagc ttttaggaac cgtcggcatg | 840 |
| ttgctgttga agtgtggagt tgtgagcgtg gactgtggca agtcgacagc gtgtactaag | 900 |
| agttgcacta ctgcaagcgg gtgttctgtc cggtactcac tcgtacacta ttttttttgta | 960 |
| ctgctggtat tgtaccagaa acattttctt ttattgttac ttgcttttta aactttgttt | 1020 |
| agccacttaa ggaagatctg cttatggcac aatttgcctc aaatccattc caagttgtat | 1080 |
| atttgttttc caataaaaaa aaatgacaat tt | 1112 |

<210> SEQ ID NO 11
<211> LENGTH: 3320
<212> TYPE: DNA
<213> ORGANISM: Homo sapiens

<400> SEQUENCE: 11

| | |
|---|---|
| atgtcctttc gggcagccag gctcagcatg aggaacagaa ggaatgacac tctggacagc | 60 |
| acccggaccc tgtactccag cgcgtctcgg agcacagact tgtcttacag tgaaagcgac | 120 |
| ttggtgaatt ttattcaagc aaatttttaag aaacgagaat gtgtcttctt tatcaaagat | 180 |
| tccaaggcca cggagaatgt gtgcaagtgt ggctatgccc agagccagca catggaaggc | 240 |
| acccagatca accaaagtga gaaatggaac tacaagaaac acaccaagga atttcctacc | 300 |
| gacgcctttg gggatattca gtttgagaca ctggggaaga agggaagta tatacgtctg | 360 |
| tcctgcgaca cggacgcgga aatcctttac gagctgctga cccagcactg gcacctgaaa | 420 |
| acacccaacc tggtcatttc tgtgaccggg ggcgccaaga acttcgccct gaagccgcgc | 480 |
| atgcgcaaga tcttcagccg gctcatctac atcgcgcagt ccaaaggtgc ttggattctc | 540 |
| acggaggca cccattatgg cctgatgaag tacatcgggg aggtggtgag agataacacc | 600 |
| atcagcagga gttcagagga gaatattgtg gccattggca tagcagcttg gggcatggtc | 660 |
| tccaaccggg acaccctcat caggaattgc gatgctgagg gctatttttt agcccagtac | 720 |
| cttatggatg acttcacaag agatccactg tatatcctgg acaacaacca cacacatttg | 780 |
| ctgctcgtgg acaatggctg tcatggacat cccactgtcg aagcaaagct ccggaatcag | 840 |
| ctagagaagt atatctctga gcgcactatt caagattcca actatggtgg caagatcccc | 900 |
| attgtgtgtt tgcccaagg aggtggaaaa gagactttga agccatcaa tacctccatc | 960 |
| aaaaataaaa ttccttgtgt ggtggtggaa ggctcgggcc agatcgctga tgtgatcgct | 1020 |
| agcctggtgg aggtggagga tgccctgaca tcttctgccg tcaaggagaa gctggtgcgc | 1080 |
| tttttacccc gcacggtgtc ccggctgcct gaggaggaga ctgagagttg gatcaaatgg | 1140 |
| ctcaaagaaa ttctcgaatg ttctcaccta ttaacagtta ttaaaatgga agaagctggg | 1200 |
| gatgaaattg tgagcaatgc catctcctac gctctataca aagccttcag caccagtgag | 1260 |
| caagacaagg ataactggaa tgggcagctg aagcttctgc tggagtggaa ccagctggac | 1320 |
| ttagccaatg atgagatttt caccaatgac cgccgatggg agtctgctga ccttcaagaa | 1380 |
| gtcatgttta cggctctcat aaaggacaga cccaagtttg tccgcctctt tctggagaat | 1440 |
| ggcttgaacc tacggaagtt ctcacccat gatgtcctca ctgaactctt ctccaaccac | 1500 |
| ttcagcacgc ttgtgtaccg gaatctgcag atcgccaaga attcctataa tgatgccctc | 1560 |
| ctcacgtttg tctggaaact ggttgcgaac ttccgaagag gcttccggaa ggaagacaga | 1620 |
| aatggccggg acgagatgga catagaactc cacgacgtgt ctcctattac tcggcacccc | 1680 |
| ctgcaagctc tcttcatctg gccattctt cagaataaga aggaactctc caaagtcatt | 1740 |
| tgggagcaga ccagggctg cactctggca gccctgggag ccagcaagct tctgaagact | 1800 |

-continued

| | |
|---|---|
| ctggccaaag tgaagaacga catcaatgct gctggggagt ccgaggagct ggctaatgag | 1860 |
| tacgagaccc gggctgttga gctgttcact gagtgttaca gcagcgatga agacttggca | 1920 |
| gaacagctgc tggtctattc ctgtgaagct tggggtggaa gcaactgtct ggagctggcg | 1980 |
| gtggaggcca cagaccagca tttcatcgcc cagcctgggg tccagaattt tctttctaag | 2040 |
| caatggtatg gagagatttc ccgagacacc aagaactgga agattatcct gtgtctgttt | 2100 |
| attatacccct tggtgggctg tggctttgta tcatttagga gaaacctgt cgacaagcac | 2160 |
| aagaagctgc tttggtacta tgtggcgttc ttcacctccc ccttcgtggt cttctcctgg | 2220 |
| aatgtggtct tctacatcgc cttcctcctg ctgtttgcct acgtgctgct catggatttc | 2280 |
| cattcggtgc cacaccccc cgagctggtc ctgtactcgc tggtctttgt cctcttctgt | 2340 |
| gatgaagtga cagtggta cgtaaatggg gtgaattatt ttactgacct gtggaatgtg | 2400 |
| atggacacgc tggggctttt ttacttcata gcaggaattg tatttcggct ccactcttct | 2460 |
| aataaaagct ctttgtattc tggacgagtc attttctgtc tggactacat tattttcact | 2520 |
| ctaagattga tccacatttt tactgtaagc agaaacttag acccaagat tataatgctg | 2580 |
| cagaggatgc tgatcgatgt gttcttcttc ctgttcctct ttgcggtgtg atggtggcc | 2640 |
| tttggcgtgg ccaggcaagg gatccttagg cagaatgagc agcgctggag gtggatattc | 2700 |
| cgttcggtca tctacgagcc ctacctggcc atgttcggcc aggtgcccag tgacgtggat | 2760 |
| ggtaccacgt atgactttgc ccactgcacc ttcactggga atgagtccaa gccactgtgt | 2820 |
| gtggagctgg atgagcacaa cctgcccgg ttccccgagt ggatcaccat ccccctggtg | 2880 |
| tgcatctaca tgttatccac caacatcctg ctggtcaacc tgctggtcgc catgtttggc | 2940 |
| tacacggtgg gcaccgtcca ggagaacaat gaccaggtct ggaagttcca gaggtacttc | 3000 |
| ctggtgcagg agtactgcag ccgcctcaat atccccttcc ccttcatcgt cttcgcttac | 3060 |
| ttctacatgg tggtgaagaa gtgcttcaag tgttgctgca aggagaaaaa catggagtct | 3120 |
| tctgtctgct gtttcaaaaa tgaagacaat gagactctgg catgggaggg tgtcatgaag | 3180 |
| gaaaactacc ttgtcaagat caacacaaaa gccaacgaca cctcagagga aatgaggcat | 3240 |
| cgatttagac aactggatac aaagcttaat gatctcaagg gtcttctgaa agagattgct | 3300 |
| aataaaatca aataaaatca | 3320 |

<210> SEQ ID NO 12
<211> LENGTH: 3315
<212> TYPE: DNA
<213> ORGANISM: mouse

<400> SEQUENCE: 12

| | |
|---|---|
| atgtccttcg agggagccag gctcagcatg aggagccgca gaaatggtac tatgggcagc | 60 |
| acccggaccc tgtactccag tgtatctcgg agcacagacg tgtcctacag tgacagtgat | 120 |
| ttggtgaatt ttattcaggc aaattttaaa aaacgagaat gtgtcttctt taccagagac | 180 |
| tccaaggcca tggagaacat atgcaagtgt ggttatgccc agagccagca catcgaaggc | 240 |
| acccagatca accaaaatga aagtggaac tacaaaaaac ataccaagga gtttccaaca | 300 |
| gacgccttcg gggacattca gtttgagact ctggggaaga aggcaagta cttacgcttg | 360 |
| tcctgtgaca ccgactctga aactctctac gaactgctga cccagcactg gcacctcaaa | 420 |
| acacccaacc tggtcatttc agtgacgggt ggagccaaaa actttgcttt gaagccacgc | 480 |
| atgcgcaaga tcttcagcag gctgattac atcgcacagt ctaaaggtgc gtggattctc | 540 |
| actggaggca ctcactacgg cctgatgaag tacataggcg aggtggtgag agacaacacc | 600 |

```
atcagcagga actcagaaga gaacatcgtg gccattggca tcgcagcatg gggcatggtc      660
tccaacaggg acaccctcat caggagctgt gatgatgagg acattttc agctcaatac       720 atcatggatg actttaccag agaccctcta tacatcctgg acaacaacca tacccacctg     780
ctgcttgtgg acaacggttg tcatggacac cccacagtgg aagccaagct ccggaatcag     840
ctggaaaagt acatctctga gcgcaccagt caagattcca actatggtgg taagatcccc    900
atcgtgtgtt ttgcccaagg aggtggaaga gagactctaa aagccatcaa cacctctgtc    960
aaaagcaaga tcccttgtgt ggtggtggaa ggctcggggc agattgctga tgtgatcgcc   1020
agcctggtgg aggtggagga tgttttaacc tcttccatgg tcaaagagaa gctggtacgc   1080
tttttaccac gcactgtgtc ccggctgcct gaagaggaaa ttgagagctg atcaaatgg    1140 ctcaaagaaa ttcttgagag ttctcaccta ctcacagtaa ttaagatgga agaggctgga   1200
gatgagattg tgagcaacgc catttcctat gcgctgtaca aagccttcag cactaatgag   1260
caagacaagg acaactggaa tggacagctg aagcttctgc tggagtggaa ccagttggac   1320
cttgccagtg atgagatctt caccaatgac cgccgctggg agtctgccga ccttcaggag   1380
gtcatgttca cggctctcat aaaggacaga cccaagtttg tccgcctctt tctggagaat   1440
ggcctgaatc tgcagaagtt tctcaccaat gaagtcctca cagagctctt ctccacccac   1500
ttcagcaccc tagtgtaccg gaacctgcag atcgccaaga actcctacaa tgacgcactc   1560
ctcacctttg tctggaagtt ggtggcaaac ttccgtcgaa gcttctggaa agaggacaga   1620
agcagcaggg aggacttgga tgtggaactc catgatgcat ctctcaccac ccggcacccg   1680
ctgcaagctc tcttcatctg gccattctt cagaacaaga aggaactctc caaggtcatt    1740
tgggagcaga ccaaaggctg tactctggca gccttggggg ccagcaagct tctgaagacc   1800
ctggccaaag ttaagaatga tatcaacgct gctggggaat cggaggaact ggccaatgaa   1860
tatgagaccc gagcagtgga gttgttcacc gagtgttaca gcaatgatga agacttggca   1920
gaacagctac tggtctactc ctgcgaagcc tggggtggga gcaactgtct ggagctggca   1980
gtggaggcta cagatcagca tttcatcgct cagcctgggg tccagaattt cctttctaag   2040
caatggtatg gagagatttc ccgagacacg aagaactgga gattatcct gtgtctattc    2100 attatcccct tagtgggctg tggcctcgta tcatttagga agaaaccat gacaagcac     2160 aagaagctgc tgtggtacta tgtggccttc ttcacgtcgc ccttcgtggt cttctcctgg   2220
aacgtggtct tctacatcgc cttcctcctg ctgtttgcct atgtgctgct catggacttc   2280
cactcagtgc cacacacccc cgagctgatc ctctacgccc tggtcttcgt cctcttctgt   2340
gatgaagtga ggcagtggta catgaacgga gtgaattatt tcaccgacct atggaacgtt   2400
atggacaccc tgggactctt ctacttcata gcgggtattg tattccggct ccactcttct   2460
aataaaagct cgttgtactc tgggcgcgtc attttctgtc tggattacat tatattcacg   2520
ctaaggctca tccacatttt caccgtcagc aggaacttgg acccaagat tataatgctg    2580 cagcggatgc tgatcgacgt ttcttcttc ctgttcctct ttgctgtgtg gatggtggcc    2640
tttggcgtgg ccagacaggg gatcctaagg caaaatgaac agcgctggag atggatcttc   2700
cgctctgtca tctatgagcc ctacctggcc atgtttggcc aggttccag tgacgtggat    2760 agtaccacat atgacttctc ccactgtacc ttctcgggaa atgagtccaa gccactgtgt   2820
gtggagctgg atgagcacaa cctgccccgc ttccctgagt ggatcaccat tccgctggtg   2880
tgcatctaca tgctctccac caatatcctt ctggtcaacc tcctggtcgc catgtttggc   2940
tacacggtag gcattgtaca ggagaacaac gaccaggtct ggaaattcca gcggtacttc   3000
```

```
ctggtgcagg agtactgcaa ccgcctaaac atcccttcc ccttcgttgt cttcgcttat    3060
ttctacatgg tggtgaagaa gtgtttcaaa tgctgctgta agagaagaa tatggagtct    3120 aatgcctgct gtttcagaaa tgaggacaat gagactttgg cgtgggaggg tgtcatgaag    3180
gagaattacc ttgtcaagat caacacgaaa gccaacgaca actcagagga gatgaggcat    3240
cggtttagac aactggactc aaagcttaac gacctcaaaa gtcttctgaa agagattgct    3300
aataacatca agtaa                                                     3315

<210> SEQ ID NO 13
<211> LENGTH: 3315
<212> TYPE: DNA
<213> ORGANISM: rat

<400> SEQUENCE: 13
atgtccttcg agggagccag gctcagcatg aggagccgca gaaatggaac tctgggcagc      60
acccggaccc tgtactccag cgtgtctcgg agcacagacg tgtcctacag tgaaagtgat     120
ttggtgaatt ttattcaggc aaattttaaa aaacgagaat gcgtcttctt taccagagac     180
tccaaggcca tggagagcat atgcaagtgt ggttatgccc agagccagca tatcgaaggc     240
acccagatca accaaaatga aagtggaac tacaaaaaac acaccaagga gtttccaaca     300
gacgcctttg gggacattca gtttgagact ctggggaaga aaggcaagta cttacgctta     360
tcctgtgaca cggactctga aaccctctac gaactgctga cccagcactg gcacctcaaa     420
acacccaacc tggtcatctc agtgacgggt ggagccaaaa actttgcttt gaagccacgc     480
atgcgcaaaa tcttcagtcg gctgatctac atcgctcagt ctaaaggggc atggattctt     540
accggaggca ctcattacgg tctgatgaag tacataggtg aagtggtgag ggataacacc     600
atcagcagga actcggaaga gaacatcgtg gccattggca tagcggcctg gggcatggtc     660
tccaacaggg acaccctcat caggaattgt gatgatgagg acatttttc agctcaatat     720 atcatggatg acttcatgag agatcctctc tacatcctgg acaacaatca tacccacctg     780
ctgcttgtgg acaacggttg tcatggacac cccacggtgg aagccaaact tcggaatcag     840
ctggagaagt acatctctga gcgcaccagt caagattcca actatggtgg taagatcccc     900
atcgtgtgtt tgcccagggg aggtggaaga gaaactttga agccatcaa cacctctgtc     960 aaaagtaaga tcccctgtgt ggtggtggaa ggctcgggc agattgccga tgtgattgcc    1020
agcctggtgg aggtagagga tgttttaacc tcttccatgg tcaaagagaa gctggtacgg    1080 ttttacccc gcactgtgtc ccggctgcct gaagaggaga ttgagagctg atcaaatgg    1140 ctcaaagaaa tcttgagag cccccacctc ctcacggtca tcaagatgga ggaggctgga    1200
gacgaggtcg tgagcagcgc catttcctac gcgctgtaca agccttcag cactaatgaa    1260 caagacaagg acaactggaa cggacagctg aagcttctgc tggagtggaa ccaactggac    1320
cttgccagtg atgagatctt caccaatgac cgccgctggg agtctgccga ccttcaggaa    1380
gtcatgttca cggccctcat aaaggacagg cccaagtttg tccgcctctt cctggagaat    1440
ggcctcaacc tgcagaagtt cctcaccaat gaagtcctca cggagctctt ctccaccca    1500 ttcagcaccc tagtgtaccg gaacctgcag atcgccaaga actcctacaa cgatgcactc    1560
cttacctttg tctggaagtt ggtggcaaac ttccgtagaa gcttctggaa agaggacaga    1620
agcagcaggg aggacttgga tgtggaactc catgatgcat ctctcaccac ccggcacccc    1680
ctgcaggctc ttttcatctg ggccattctt cagaacaaga ggaactctc caaggtcatc    1740 tgggagcaaa ccaaaggctg tactctggcc gccttggggg ccagcaaact tctgaagacc    1800
```

```
ctggccaaag ttaagaatga tatcaacgca gctggggaat ctgaggaact ggctaatgag   1860
tatgagaccc gagcagtgga gttgttcact gagtgttaca gcagtgatga ggacttggca   1920
gaacagctac tggtctactc ttgtgaagcc tggggtggga gcaactgtct ggagctggcg   1980
gtggaggcta cggaccagca tttcattgct cagcctgggg tccagaattt cctttctaag   2040
caatggtatg gagagatttc ccgagacacg aagaactgga agattatcct gtgtctgttc   2100
atcatccccc tggtgggctg tggcctcgta tcgtttagga agaagcccat tgacaagcac   2160
aagaagctgc tctggtacta cgtggccttc ttcacttcgc ccttcgtggt cttctcctgg   2220
aacgtggtct tctacatcgc cttcctcctg ctgtttgcgt atgtgctgct catggacttc   2280
cactcggtgc cacacacccc cgagctgatc ctctatgccc tggtcttcgt cctcttctgt   2340
gatgaagtga ggcagtggta catgaacgga gtgaattatt tcaccgacct atggaacgtt   2400
atggacacac tgggactttt ctacttcata gcgggtattg tattccggct tcactcttca   2460
aataaaagct ctttgtactc cgggcgagtc attttctgtc tggattacat tatattcact   2520
ctaaggctca tccacatttt caccgtgagc aggaacctgg acccaagat tataatgctg   2580 cagcggatgc tcatcgacgt tttcttcttc ttgtttctct ttgctgtgtg gatggtggcc   2640
ttcggcgtag ccagacaggg gatccttagg caaaatgaac agcgctggag gtggatcttc   2700
cgctctgtca tctatgagcc ctacctggcc atgtttggcc aggtgcccag tgatgtggac   2760
agtaccacat atgacttctc ccactgcacc ttctcgggaa atgagtccaa gccactgtgc   2820
gtggagctag atgaatacaa tctgccccgc ttccctgagt ggatcaccat cccactagtg   2880
tgcatctaca tgctctccac caacatcctt ctggtcaatc tcctggtcgc catgtttggc   2940
tacacggtgg gcattgtgca ggagaacaac gatcaggtct ggaagttcca gcggtacttc   3000
ctggtgcagg agtactgcaa ccgcctcaac atccccttcc ccttcgtcgt cttcgcttac   3060
ttctacatgg tggtcaagaa gtgtttcaaa tgctgctgta aagagaagaa cacggagtct   3120
tctgcctgct gtttcagaaa tgaggacaac gagactttgg cgtgggaggg cgtcatgaag   3180
gagaattacc ttgtcaagat caacacgaag gccaacgaca acgcagagga gatgaggcat   3240
cggttcagac aactgacaca aaagcttaat gatctcaaag tcttctctgaa agagattgct   3300 aataaaatca aataa                                                    3315
```

<210> SEQ ID NO 14
<211> LENGTH: 34
<212> TYPE: DNA
<213> ORGANISM: oligo

<400> SEQUENCE: 14

```
atcgatatgt ccttcgaggg agccaggctc agca                                 34
```

<210> SEQ ID NO 15
<211> LENGTH: 18
<212> TYPE: DNA
<213> ORGANISM: Oligo

<400> SEQUENCE: 15

```
attggcatag cagcttgg                                                   18
```

<210> SEQ ID NO 16
<211> LENGTH: 36
<212> TYPE: DNA
<213> ORGANISM: Oligo

<400> SEQUENCE: 16

```
tctagagtcg accgtgtctc gggaaatctc tccata                    36
```

<210> SEQ ID NO 17
<211> LENGTH: 33
<212> TYPE: DNA
<213> ORGANISM: Oligo

<400> SEQUENCE: 17

```
tctagagtcg acggaagagg ttaaaacatc ctc                       33
```

<210> SEQ ID NO 18
<211> LENGTH: 22
<212> TYPE: DNA
<213> ORGANISM: Oligo

<400> SEQUENCE: 18

```
cccaaccatg gtcatctcag tg                                   22
```

<210> SEQ ID NO 19
<211> LENGTH: 23
<212> TYPE: DNA
<213> ORGANISM: Oligo

<400> SEQUENCE: 19

```
gggccatggt ctccaacagg gac                                  23
```

<210> SEQ ID NO 20
<211> LENGTH: 32
<212> TYPE: DNA
<213> ORGANISM: Oligo

<400> SEQUENCE: 20

```
atcaatccat ggctcagtct aaagggggcat gg                       32
```

<210> SEQ ID NO 21
<211> LENGTH: 32
<212> TYPE: DNA
<213> ORGANISM: Oligo

<400> SEQUENCE: 21

```
atcaatccat ggataacacc atcagcagga ac                        32
```

<210> SEQ ID NO 22
<211> LENGTH: 33
<212> TYPE: DNA
<213> ORGANISM: Oligo

<400> SEQUENCE: 22

```
tctagagtcg acttaccagg ccgctatgcc aat                       33
```

<210> SEQ ID NO 23
<211> LENGTH: 36
<212> TYPE: DNA
<213> ORGANISM: Oligo

<400> SEQUENCE: 23

```
tctagagtcg acttactacc tcaccacttc acctat                    36
```